(12) United States Patent
Chen et al.

(10) Patent No.: US 9,758,538 B2
(45) Date of Patent: Sep. 12, 2017

(54) PYRIMIDINE DERIVATIVES

(71) Applicant: PFIZER INC., New York, NY (US)

(72) Inventors: Ping Chen, San Diego, CA (US); Hengmiao Cheng, San Diego, CA (US); Gary Michael Gallego, San Diego, CA (US); Mehran Jalaie, San Diego, CA (US); John Charles Kath, La Mesa, CA (US); Suvi Tuula Marjukka Orr, San Diego, CA (US); Mason Alan Pairish, San Diego, CA (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 15/209,574

(22) Filed: Jul. 13, 2016

(65) Prior Publication Data

US 2017/0015689 A1    Jan. 19, 2017

Related U.S. Application Data

(60) Provisional application No. 62/192,975, filed on Jul. 15, 2015.

(51) Int. Cl.

| | | |
|---|---|---|
| *C07F 9/6558* | (2006.01) | |
| *C07D 401/14* | (2006.01) | |
| *C07D 413/14* | (2006.01) | |
| *C07D 403/14* | (2006.01) | |
| *C07D 405/14* | (2006.01) | |
| *A61K 31/5377* | (2006.01) | |
| *C07D 401/04* | (2006.01) | |
| *C07D 403/04* | (2006.01) | |

(52) U.S. Cl.
CPC ...... *C07F 9/65583* (2013.01); *A61K 31/5377* (2013.01); *C07D 401/04* (2013.01); *C07D 401/14* (2013.01); *C07D 403/04* (2013.01); *C07D 403/14* (2013.01); *C07D 405/14* (2013.01); *C07D 413/14* (2013.01)

(58) Field of Classification Search
None
See application file for complete search history.

(56) References Cited

U.S. PATENT DOCUMENTS

| | | | |
|---|---|---|---|
| 6,849,660 | B1 | 2/2005 | Jefferson et al. |
| 8,217,035 | B2 | 7/2012 | Burger et al. |
| 8,563,549 | B2 * | 10/2013 | Burger ............... C07D 401/04 514/232.2 |
| 9,260,439 | B2 | 2/2016 | Chen et al. |
| 2004/0254236 | A1 | 12/2004 | Dong et al. |
| 2005/0032805 | A1 | 2/2005 | Jefferson et al. |
| 2006/0058308 | A1 | 3/2006 | Norman et al. |
| 2006/0287355 | A1 | 12/2006 | Hemmerling et al. |
| 2007/0043049 | A1 | 2/2007 | Bakthavatchalam et al. |
| 2009/0209586 | A1 | 8/2009 | Blumenfeld et al. |
| 2010/0004298 | A1 | 1/2010 | Dong et al. |
| 2010/0035907 | A1 | 2/2010 | Bouaboula et al. |
| 2010/0041637 | A1 | 2/2010 | Claremon et al. |
| 2010/0069417 | A1 | 3/2010 | Bouaboula et al. |
| 2010/0204230 | A1 | 8/2010 | Blurton et al. |
| 2010/0222353 | A1 | 9/2010 | Humphrey |

(Continued)

FOREIGN PATENT DOCUMENTS

| | | |
|---|---|---|
| WO | 9705130 A1 | 2/1997 |
| WO | 9705131 A1 | 2/1997 |

(Continued)

OTHER PUBLICATIONS

Stark et al., PI3K inhibitors in inflammation, autoimmunity and cancer. Current Opinion in Pharmacology, 2015, 23, 82-91.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*

(Continued)

*Primary Examiner* — Matthew Coughlin
*Assistant Examiner* — Po-Chih Chen
(74) *Attorney, Agent, or Firm* — Suzanne M. Bates; Stephen D. Prodnuk

(57) ABSTRACT

The present invention relates to compounds of formula (I)

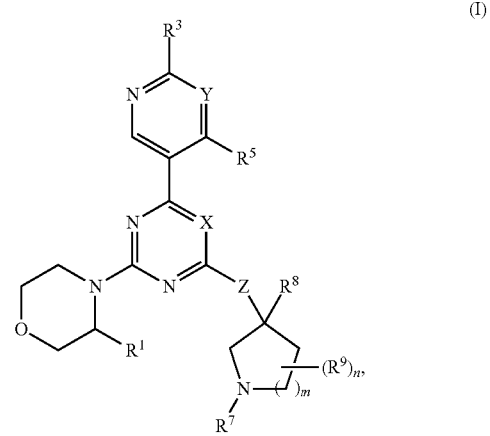

(I)

or pharmaceutically acceptable salts thereof, wherein X, Y, Z, $R^1$-$R^{11}$, m, n, and p are defined herein. The novel pyrimidine derivatives are useful in the treatment of abnormal cell growth, such as cancer, in mammals. Additional embodiments relate to pharmaceutical compositions containing the compounds and to methods of using the compounds and compositions in the treatment of abnormal cell growth in mammals.

30 Claims, No Drawings

(56) References Cited

U.S. PATENT DOCUMENTS

| | | |
|---|---|---|
| 2011/0306587 A1 | 12/2011 | Allen et al. |
| 2011/0306588 A1 | 12/2011 | Allen et al. |
| 2012/0094999 A1 | 4/2012 | Gray et al. |
| 2012/0178926 A1 | 7/2012 | Charrier et al. |
| 2012/0196905 A1 | 8/2012 | Cashman |
| 2012/0202776 A1 | 8/2012 | Wang et al. |
| 2012/0220633 A1 | 8/2012 | Blumenfeld et al. |
| 2013/0225527 A1 | 8/2013 | Wang et al. |
| 2013/0225528 A1 | 8/2013 | Wang et al. |
| 2013/0253186 A1 | 9/2013 | Allen et al. |
| 2014/0066406 A1 | 3/2014 | Wang et al. |
| 2014/0187774 A1 | 7/2014 | Charrier et al. |
| 2014/0213572 A1 | 7/2014 | Allen et al. |
| 2014/0213583 A1 | 7/2014 | De Giovanni et al. |
| 2015/0141426 A1 | 5/2015 | Hirawat et al. |
| 2015/0225436 A1 | 8/2015 | Wang et al. |
| 2015/0232596 A1 | 8/2015 | Fornof et al. |
| 2016/0102075 A1 | 4/2016 | Allen et al. |
| 2016/0376297 A1 | 12/2016 | Wang et al. |

FOREIGN PATENT DOCUMENTS

| | | |
|---|---|---|
| WO | 0209648 A2 | 2/2002 |
| WO | 2004048365 A1 | 6/2004 |
| WO | 2005000298 A2 | 1/2005 |
| WO | 2007084786 A1 | 7/2007 |
| WO | 2009066084 A1 | 5/2009 |
| WO | 2012101654 A2 | 8/2012 |
| WO | WO2014016849 * | 1/2014 |
| WO | 2016001789 A1 | 1/2016 |

OTHER PUBLICATIONS

Burger, M., et al., "Identification of NVP-BKM120 as a Potent, Selective, Orally Bioavailable Class I PI3 Kinase Inhibitor for Treating Cancer," 2011, ACS Medicinal Chemistry Letters, 774-779, vol. 2.

Burger, M., et al., "Synthesis and in Vitro and in Vivo Evaluation of Phosphoinositide-3-kinase Inhibitors," 2011, ACS Medicinal Chemistry Letters, 34-38, vol. 2.

International Search Report for International Appln. No. PCT/IB2016/054085 completed on Aug. 5, 2016; Mailing Date of Aug. 16, 2016.

Pecchi, S., et al., "Identification and structure-activity relationship of 2-morpholino 6-(3-hydroxyphenyl) pyrimidines, a class of potent and selective PI3 kinase inhibitors," 2010, Bioorganic & Medicinal Chemistry Letters, 6895-6898, vol. 20.

Written Opinion for International Appln. No. PCT/IB2016/054085 completed on Aug. 5, 2016; Mailing Date of Aug. 16, 2016.

* cited by examiner

PYRIMIDINE DERIVATIVES

CROSS-REFERENCE TO RELATED APPLICATIONS

This patent application claims the benefit of priority to U.S. Provisional Patent Application Ser. No. 62/192,975, filed Jul. 15, 2015, the contents of which are hereby incorporated by reference in their entireties.

FIELD OF THE INVENTION

The present invention relates to novel pyrimidine derivatives that are useful in the treatment of abnormal cell growth, such as cancer, in mammals. The present invention also relates to pharmaceutical compositions containing the compounds and to methods of using the compounds and compositions in the treatment of abnormal cell growth in mammals.

BACKGROUND OF THE INVENTION

Phosphoinositide 3-kinases ("PI3Ks") comprise a family of lipid kinases that catalyze the synthesis of the phosphatidylinositol ("PI") second messengers PI(3)P ("PIP"), PI(3, 4)P$_2$ ("PIP$_2$"), and PI(3,4,5)P$_3$ ("PIP$_3$"). (Fruman et al., "Phosphoinositide kinases", *Annu. Rev. Biochem.* 67 (1998), pp. 481-507; Knight et al., "A Pharmacological Map of the PI3-K Family Defines a Role for p110a in Insulin Signaling", *Cell* 125 (2006), pp. 733-747.) In the appropriate cellular context, these lipids mediate diverse physiological processes including cell growth, survival, differentiation, and chemotaxis. (Katso et al., "Cellular function of phosphoinositide 3-kinases: implications for development, homeostasis, and cancer", *Annu. Rev. Cell Dev. Biol.* 17 (2001), pp. 615-675.) The PI3K family comprises at least 15 different lipid and serine/threonine kinases, sub-classified by structural homology, with distinct substrate specificities, expression patterns, and mode of regulation. Class I PI3Kα is the main PI3-kinase isoform in cancer, and consists of catalytic (p110α) and adapter (p85) subunits. (Stirdivant et al., "Cloning and mutagenesis of the p110α subunit of human phosphoinositide 3'-hydroxykinase", *Bioorg. Med. Chem.* 5 (1997), pp. 65-74.)

The 3-phosphorylated phospholipid, PIP$_3$, acts as a second messenger recruiting kinases with lipid binding domains (including plekstrin homology ("PH") regions), such as Akt, the product of the human homologue of the viral oncogene v-Akt, and phosphoinositide-dependent kinase-1 ("PDK1"). (Vivanco & Sawyers, "The Phosphatidylinositol 3-Kinase-Akt Pathway In Human Cancer", *Nature Reviews Cancer* 2 (2002), pp. 489-501.) Binding of Akt to PIP$_3$ induces Akt to translocate to the plasma membrane, bringing Akt into contact with PDK1, which activates Akt. The tumor-suppressor phosphatase, PTEN, dephosphorylates PIP$_3$, and therefore acts as a negative regulator of Akt activation. The PI3Ks, Akt and PDK1 are important in the regulation of many cellular processes including cell cycle regulation, proliferation, survival, apoptosis and motility and are significant components of the molecular mechanisms of diseases such as cancer, diabetes and immune inflammation. Functional loss of PTEN (the most commonly mutated tumor-suppressor gene in cancer after p53), oncogenic mutations in the PIK3CA gene encoding PI3Kα, amplification of the PIK3CA gene and overexpression of Akt have been established in many malignancies (see, for example, Samuels, et al., "High frequency of mutations of the PIK3CA gene in human cancers", *Science* 304 (2004), p. 554; Broderick et al., "Mutations in PIK3CA in anaplastic oligodendrogliomas, high-grade astrocytomas, and medulloblastomas", *Cancer Research* 64 (2004), pp. 5048-5050). Therefore, the deregulation of PI3k and the upstream and downstream components of this signaling pathway is one of the most common deregulations associated with human cancers and proliferative diseases. (Parsons et al., *Nature*, 436 (2005), p. 792; Hennessey et al., *Nature Rev. Drug Disc.* 4 (2005) 988-1004.)

PI3Kα is thus an attractive target for cancer drug development because PI3Kα inhibitors would be expected to inhibit proliferation and summon resistance to cytotoxic agents in cancer cells.

SUMMARY OF THE INVENTION

Each of the embodiments described below can be combined with any other embodiment described herein not inconsistent with the embodiment with which it is combined. Furthermore, each of the embodiments described herein envisions within its scope the pharmaceutically acceptable salts of the compounds described herein. Accordingly, the phrase "or a pharmaceutically acceptable salt thereof" is implicit in the description of all compounds described herein.

Embodiments described herein relate to a compound of formula (I)

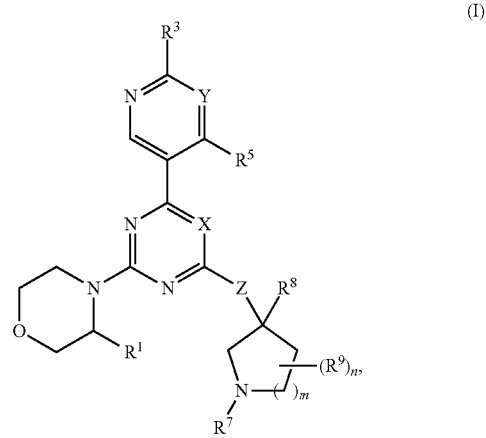

(I)

or a pharmaceutically acceptable salt thereof,
wherein
X is N or CR$^2$;
R$^1$ is hydrogen or methyl;
R$^2$ is hydrogen, fluorine, or chlorine;
R$^3$ is methyl or NH$_2$;
Y is N or CR$^4$;
R$^4$ is hydrogen, cyano, or fluorine;
R$^5$ is hydrogen, methyl, or CF$_3$;
Z is NR$^6$ or O;
R$^6$ is hydrogen or C$_1$-C$_3$ alkyl;
R$^7$ is hydrogen,
C$_1$-C$_4$ alkyl, optionally substituted by one, two, or three substituents selected from the group consisting of fluorine, hydroxy, and NH$_2$,
—CH$_2$—(C$_3$-C$_4$ cycloalkyl),
—C(O)—(C$_1$-C$_6$ alkyl), optionally substituted by one, two, or three substituents selected from the group consisting of fluorine, NH$_2$, hydroxy, methoxy, and phenyl, —C(O)—(C$_3$-C$_4$ cycloalkyl), optionally substituted by one or two substituents selected from the group consisting of fluorine and C$_1$-C$_4$ alkyl, —[(CH$_2$)]$_p$—C(O)-(4-5 membered heterocycloalkyl), optionally substituted by one or two substituents selected from the group consisting of fluorine and C$_1$-C$_4$ alkyl, —C(O)-(5-6 membered heteroaryl), optionally substituted by one or two substituents selected from the group consisting of fluorine and C$_1$-C$_4$ alkyl, —[(CH$_2$)]$_p$—C(O)—[N(R$^{10}$)(R$^{11}$)], —C(O)O—(C$_1$-C$_4$ alkyl), optionally substituted by one, two, or three substituents selected from the group consisting of fluorine, NH$_2$, hydroxy, methoxy, and phenyl, —C(O)O—(C$_3$-C$_4$ cycloalkyl), optionally substituted by one or two substituents selected from the group consisting of fluorine and C$_1$-C$_4$ alkyl, —S(O)$_2$—(C$_1$-C$_4$ alkyl), 4-6 membered heterocycloalkyl, optionally substituted by one or two substituents selected from the group consisting of oxo and C$_1$-C$_4$ alkyl or 5-6 membered heteroaryl, optionally substituted by one or two substituents selected from the group consisting of oxo and C$_1$-C$_4$ alkyl;

R$^8$ is hydrogen, cyano, C$_1$-C$_3$ alkyl, CH$_2$F, CHF$_2$, CF$_3$, or CH$_2$—O—C(O)—(C$_1$-C$_3$ alkyl), wherein the C$_1$-C$_3$ alkyl is optionally substituted by hydroxy, methoxy, or —O—P(O)(OH)$_2$;

R$^9$ is fluorine or methyl;

R$^{10}$ is hydrogen or methyl;

R$^{11}$ is C$_1$-C$_4$ alkyl, optionally substituted by one, two, or three fluorine atoms, provided that R$^{10}$ and R$^{11}$ may form a 4-6 membered heterocycloalkyl ring, when p is 0;

m is 0, 1, or 2;

n is 0, 1, or 2; and p is 0 or 1.

Embodiments relate to a compound of formula (I), or a pharmaceutically acceptable salt thereof, wherein X is N.

Embodiments relate to a compound of formula (I), or a pharmaceutically acceptable salt thereof, wherein X is CR$^2$.

Embodiments relate to a compound of formula (I), or a pharmaceutically acceptable salt thereof, wherein R$^2$ is hydrogen.

Embodiments relate to a compound of formula (I), or a pharmaceutically acceptable salt thereof, wherein R$^2$ is fluorine.

Embodiments relate to a compound of formula (I), or a pharmaceutically acceptable salt thereof, wherein R$^1$ is hydrogen.

Embodiments relate to a compound of formula (I), or a pharmaceutically acceptable salt thereof, wherein R$^1$ is methyl.

Embodiments relate to a compound of formula (I), or a pharmaceutically acceptable salt thereof, wherein R$^3$ is methyl.

Embodiments relate to a compound of formula (I), or a pharmaceutically acceptable salt thereof, wherein R$^3$ is NH$_2$.

Embodiments relate to a compound of formula (I), or a pharmaceutically acceptable salt thereof, wherein Y is N.

Embodiments relate to a compound of formula (I), or a pharmaceutically acceptable salt thereof, wherein Y is CR$^4$.

Embodiments relate to a compound of formula (I), or a pharmaceutically acceptable salt thereof, wherein Y is N and R$^3$ is methyl.

Embodiments relate to a compound of formula (I), or a pharmaceutically acceptable salt thereof, wherein R$^4$ is hydrogen.

Embodiments relate to a compound of formula (I), or a pharmaceutically acceptable salt thereof, wherein R$^5$ is hydrogen.

Embodiments relate to a compound of formula (I), or a pharmaceutically acceptable salt thereof, wherein X is CR$^2$, R$^2$ is hydrogen, R$^3$ is methyl, Y is CR$^4$, and R$^5$ is hydrogen.

Embodiments relate to a compound of formula (I), or a pharmaceutically acceptable salt thereof, wherein X is CR$^2$, R$^3$ is NH$_2$ and Y is N.

Embodiments relate to a compound of formula (I), or a pharmaceutically acceptable salt thereof, wherein Z is NR$^6$.

Embodiments relate to a compound of formula (I), or a pharmaceutically acceptable salt thereof, wherein Z is O.

Embodiments relate to a compound of formula (I), or a pharmaceutically acceptable salt thereof, wherein R$^6$ is hydrogen.

Embodiments relate to a compound of formula (I), or a pharmaceutically acceptable salt thereof, wherein R$^6$ is methyl.

Embodiments relate to a compound of formula (I), or a pharmaceutically acceptable salt thereof, wherein R$^7$ is hydrogen.

Embodiments relate to a compound of formula (I), or a pharmaceutically acceptable salt thereof, wherein R$^7$ is C$_1$-C$_4$ alkyl, optionally substituted by one or two fluorine atoms.

Embodiments relate to a compound of formula (I), or a pharmaceutically acceptable salt thereof, wherein R$^7$ is —CH$_2$—(C$_3$-C$_4$ cycloalkyl).

Embodiments relate to a compound of formula (I), or a pharmaceutically acceptable salt thereof, wherein R$^7$ is —C(O)—(C$_1$-C$_6$ alkyl), optionally substituted by one or two substituents selected from the group consisting of fluorine, NH$_2$, hydroxy, methoxy, and phenyl.

Embodiments relate to a compound of formula (I), or a pharmaceutically acceptable salt thereof, wherein R$^7$ is —C(O)—(C$_3$-C$_4$ cycloalkyl), optionally substituted by one or two fluorine atoms.

Embodiments relate to a compound of formula (I), or a pharmaceutically acceptable salt thereof, wherein R$^7$ is —C(O)-cyclopropyl, optionally substituted by fluorine.

Embodiments relate to a compound of formula (I), or a pharmaceutically acceptable salt thereof, wherein R$^7$ is —C(O)O—(C$_1$-C$_4$ alkyl), optionally substituted by one, two, or three substituents selected from the group consisting of fluorine, hydroxy, and NH$_2$.

Embodiments relate to a compound of formula (I), or a pharmaceutically acceptable salt thereof, wherein R$^7$ is —C(O)O—(C$_3$-C$_4$ cycloalkyl), optionally substituted by fluorine or methyl.

Embodiments relate to a compound of formula (I), or a pharmaceutically acceptable salt thereof, wherein R$^7$ is —C(O)O-cyclopropyl, optionally substituted by fluorine.

Embodiments relate to a compound of formula (I), or a pharmaceutically acceptable salt thereof, wherein R$^8$ is CH$_2$OH.

Embodiments relate to a compound of formula (I), or a pharmaceutically acceptable salt thereof, wherein R$^8$ is CH$_2$—O—P(O)(OH)$_2$.

Embodiments relate to a compound of formula (I), or a pharmaceutically acceptable salt thereof, wherein m is 0.

Embodiments relate to a compound of formula (I), or a pharmaceutically acceptable salt thereof, wherein m is 1.

Embodiments relate to a compound of formula (I), or a pharmaceutically acceptable salt thereof, wherein m is 2.

Embodiments relate to a compound of formula (I), or a pharmaceutically acceptable salt thereof, wherein n is 0.

Embodiments relate to a compound of formula (I), or a pharmaceutically acceptable salt thereof, wherein X is $CR^2$ and m is 0.

Embodiments described herein relate to a compound of formula (I), having formula (II)

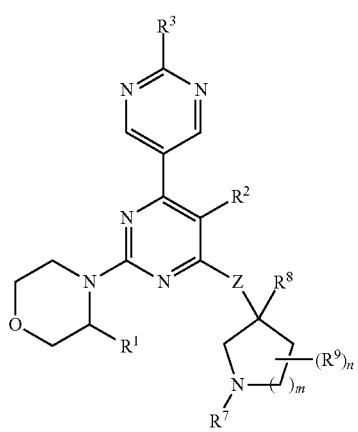

(II)

or a pharmaceutically acceptable salt thereof,
wherein
m is 1 or 2.

Embodiments relate to a compound of formula (II), or a pharmaceutically acceptable salt thereof, wherein $R^2$ is hydrogen.

Embodiments relate to a compound of formula (II), or a pharmaceutically acceptable salt thereof, wherein $R^2$ is fluorine.

Embodiments relate to a compound of formula (II), or a pharmaceutically acceptable salt thereof, wherein $R^1$ is hydrogen.

Embodiments relate to a compound of formula (II), or a pharmaceutically acceptable salt thereof, wherein $R^1$ is methyl.

Embodiments relate to a compound of formula (II), or a pharmaceutically acceptable salt thereof, wherein $R^3$ is methyl.

Embodiments relate to a compound of formula (II), or a pharmaceutically acceptable salt thereof, wherein $R^3$ is $NH_2$.

Embodiments relate to a compound of formula (II), or a pharmaceutically acceptable salt thereof, wherein Z is $NR^6$.

Embodiments relate to a compound of formula (II), or a pharmaceutically acceptable salt thereof, wherein Z is O.

Embodiments relate to a compound of formula (II), or a pharmaceutically acceptable salt thereof, wherein $R^6$ is hydrogen.

Embodiments relate to a compound of formula (II), or a pharmaceutically acceptable salt thereof, wherein $R^6$ is methyl.

Embodiments relate to a compound of formula (II), or a pharmaceutically acceptable salt thereof, wherein $R^7$ is hydrogen.

Embodiments relate to a compound of formula (II), or a pharmaceutically acceptable salt thereof, wherein $R^7$ is $C_1$-$C_4$ alkyl, optionally substituted by one or two fluorine atoms.

Embodiments relate to a compound of formula (II), or a pharmaceutically acceptable salt thereof, wherein $R^7$ is $-CH_2-(C_3$-$C_4$ cycloalkyl).

Embodiments relate to a compound of formula (II), or a pharmaceutically acceptable salt thereof, wherein $R^7$ is $-C(O)-(C_1$-$C_6$ alkyl), optionally substituted by one or two substituents selected from the group consisting of fluorine, $NH_2$, hydroxy, methoxy, and phenyl.

Embodiments relate to a compound of formula (II), or a pharmaceutically acceptable salt thereof, wherein $R^7$ is $-C(O)-(C_3$-$C_4$ cycloalkyl), optionally substituted by one or two fluorine atoms.

Embodiments relate to a compound of formula (II), or a pharmaceutically acceptable salt thereof, wherein $R^7$ is $-C(O)$-cyclopropyl, optionally substituted by fluorine.

Embodiments relate to a compound of formula (II), or a pharmaceutically acceptable salt thereof, wherein $R^7$ is $-C(O)O-(C_1$-$C_4$ alkyl), optionally substituted by one, two, or three substituents selected from the group consisting of fluorine, hydroxy, and $NH_2$.

Embodiments relate to a compound of formula (II), or a pharmaceutically acceptable salt thereof, wherein $R^7$ is $-C(O)O-(C_3$-$C_4$ cycloalkyl), optionally substituted by fluorine or methyl.

Embodiments relate to a compound of formula (II), or a pharmaceutically acceptable salt thereof, wherein $R^7$ is $-C(O)O$-cyclopropyl, optionally substituted by fluorine.

Embodiments relate to a compound of formula (II), or a pharmaceutically acceptable salt thereof, wherein $R^8$ is $CH_2OH$.

Embodiments relate to a compound of formula (II), or a pharmaceutically acceptable salt thereof, wherein $R^8$ is $CH_2-O-P(O)(OH)_2$.

Embodiments relate to a compound of formula (II), or a pharmaceutically acceptable salt thereof, wherein m is 1.

Embodiments relate to a compound of formula (II), or a pharmaceutically acceptable salt thereof, wherein m is 2.

Embodiments relate to a compound of formula (II), or a pharmaceutically acceptable salt thereof, wherein n is 0.

Embodiments described herein relate to a compound of formula (I), having having formula (III)

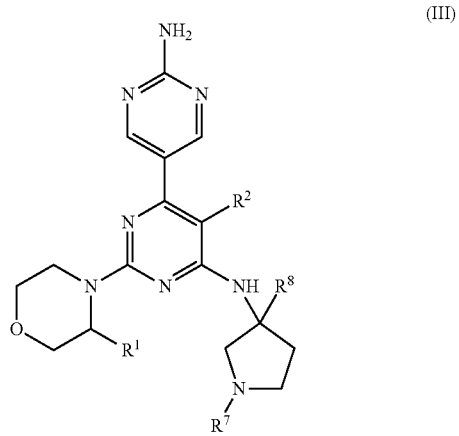

(III)

or a pharmaceutically acceptable salt thereof.

Embodiments relate to a compound of formula (III), or a pharmaceutically acceptable salt thereof, wherein $R^2$ is hydrogen.

Embodiments relate to a compound of formula (III), or a pharmaceutically acceptable salt thereof, wherein $R^2$ is fluorine.

Embodiments relate to a compound of formula (III), or a pharmaceutically acceptable salt thereof, wherein $R^1$ is hydrogen.

Embodiments relate to a compound of formula (III), or a pharmaceutically acceptable salt thereof, wherein $R^1$ is methyl.

Embodiments relate to a compound of formula (III), or a pharmaceutically acceptable salt thereof, wherein $R^7$ is hydrogen.

Embodiments relate to a compound of formula (III), or a pharmaceutically acceptable salt thereof, wherein $R^7$ is $C_1$-$C_4$ alkyl, optionally substituted by one or two fluorine atoms.

Embodiments relate to a compound of formula (III), or a pharmaceutically acceptable salt thereof, wherein $R^7$ is —$CH_2$—($C_3$-$C_4$ cycloalkyl).

Embodiments relate to a compound of formula (III), or a pharmaceutically acceptable salt thereof, wherein $R^7$ is —C(O)—($C_1$-$C_6$ alkyl), optionally substituted by one or two substituents selected from the group consisting of fluorine, $NH_2$, hydroxy, methoxy, and phenyl.

Embodiments relate to a compound of formula (III), or a pharmaceutically acceptable salt thereof, wherein $R^7$ is —C(O)—($C_3$-$C_4$ cycloalkyl), optionally substituted by one or two fluorine atoms.

Embodiments relate to a compound of formula (III), or a pharmaceutically acceptable salt thereof, wherein $R^7$ is —C(O)-cyclopropyl, optionally substituted by fluorine.

Embodiments relate to a compound of formula (III), or a pharmaceutically acceptable salt thereof, wherein $R^7$ is —C(O)O—($C_1$-$C_4$ alkyl), optionally substituted by one, two, or three substituents selected from the group consisting of fluorine, hydroxy, and $NH_2$.

Embodiments relate to a compound of formula (III), or a pharmaceutically acceptable salt thereof, wherein $R^7$ is —C(O)O—($C_3$-$C_4$ cycloalkyl), optionally substituted by fluorine or methyl.

Embodiments relate to a compound of formula (III), or a pharmaceutically acceptable salt thereof, wherein $R^7$ is —C(O)O-cyclopropyl, optionally substituted by fluorine.

Embodiments relate to a compound of formula (III), or a pharmaceutically acceptable salt thereof, wherein $R^8$ is $CH_2OH$.

Embodiments relate to a compound of formula (III), or a pharmaceutically acceptable salt thereof, wherein $R^8$ is $CH_2$—O—$P(O)(OH)_2$.

Embodiments described herein relate to a compound of formula (I), having formula (IV)

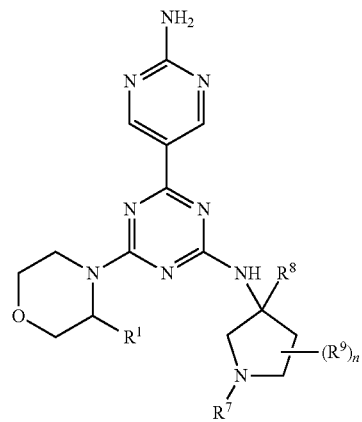

(IV)

or a pharmaceutically acceptable salt thereof.

Embodiments relate to a compound of formula (IV), or a pharmaceutically acceptable salt thereof, wherein $R^1$ is hydrogen.

Embodiments relate to a compound of formula (IV), or a pharmaceutically acceptable salt thereof, wherein $R^1$ is methyl.

Embodiments relate to a compound of formula (IV), or a pharmaceutically acceptable salt thereof, wherein $R^7$ is —C(O)O—($C_1$-$C_4$ alkyl) or —C(O)O—($C_3$-$C_4$ cycloalkyl), further wherein the —C(O)O—($C_1$-$C_4$ alkyl) and the —C(O)O—($C_3$-$C_4$ cycloalkyl) are independently optionally substituted by one or two fluorine atoms.

Embodiments relate to a compound of formula (IV), or a pharmaceutically acceptable salt thereof, wherein $R^8$ is $CH_2OH$.

Embodiments relate to a compound of formula (IV), or a pharmaceutically acceptable salt thereof, wherein $R^8$ is $CH_2$—O—$P(O)(OH)_2$.

Embodiments relate to a compound of formula (IV), or a pharmaceutically acceptable salt thereof, wherein n is 0.

In certain embodiments, the compound is selected from:
[(3S)-3-{[2'-amino-5-fluoro-2-(morpholin-4-yl)-4,5'-bipyrimidin-6-yl]amino}-3-(hydroxymethyl)pyrrolidin-1-yl](1-fluorocyclopropyl)methanone;
2,2-difluoroethyl (3S)-3-{[2'-amino-5-fluoro-2-(morpholin-4-yl)-4,5'-bipyrimidin-6-yl]amino}-3-(hydroxymethyl)pyrrolidine-1-carboxylate;
2,2-difluoroethyl (3S)-3-{[2'-amino-5-fluoro-2-(morpholin-4-yl)-4,5'-bipyrimidin-6-yl]amino}-3-[(phosphonooxy)methyl]pyrrolidine-1-carboxylate;
methyl 3-{[2'-amino-2-(morpholin-4-yl)-4,5'-bipyrimidin-6-yl]amino}-3-(hydroxymethyl)piperidine-1-carboxylate;
methyl (3S)-3-{[2'-amino-2-(morpholin-4-yl)-4,5'-bipyrimidin-6-yl]amino}-3-(hydroxymethyl)piperidine-1-carboxylate;
methyl (3R)-3-{[2'-amino-2-(morpholin-4-yl)-4,5'-bipyrimidin-6-yl]amino}-3-(hydroxymethyl)piperidine-1-carboxylate;
tert-butyl 3-{[2'-amino-2-(morpholin-4-yl)-4,5'-bipyrimidin-6-yl]oxy}-3-(hydroxymethyl)pyrrolidine-1-carboxylate;
tert-butyl 3-{[2'-amino-2-(morpholin-4-yl)-4,5'-bipyrimidin-6-yl]oxy}-3-(hydroxymethyl)pyrrolidine-1-carboxylate;

tert-butyl 3-{[2'-amino-2-(morpholin-4-yl)-4,5'-bipyrimidin-6-yl]oxy}-3-(hydroxymethyl)pyrrolidine-1-carboxylate;
tert-butyl (3S)-3-{[2'-amino-2-(morpholin-4-yl)-4,5'-bipyrimidin-6-yl]amino}-3-(1-hydroxyethyl)pyrrolidine-1-carboxylate;
methyl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate;
N~6~-[(3R)-3-methyl-1-(methylsulfonyl)pyrrolidin-3-yl]-2-(morpholin-4-yl)-4,5'-bipyrimidine-2',6-diamine;
N~6~-methyl-N~6~-[(3S)-3-methyl-1-(methylsulfonyl)pyrrolidin-3-yl]-2-(morpholin-4-yl)-4,5'-bipyrimidine-2',6-diamine;
tert-butyl (3R)-3-[{2'-amino-2-[(3S)-3-methylmorpholin-4-yl]-4,5'-bipyrimidin-6-yl}(methyl)amino]-3-methylpyrrolidine-1-carboxylate;
tert-butyl (3R)-3-({2'-amino-2-[(3S)-3-methylmorpholin-4-yl]-4,5'-bipyrimidin-6-yl}amino)-3-methylpyrrolidine-1-carboxylate;
1-{(3R)-3-[{2'-amino-2-[(3S)-3-methylmorpholin-4-yl]-4,5'-bipyrimidin-6-yl}(methyl)amino]-3-methylpyrrolidin-1-yl}ethanone;
1-[(3R)-3-({2'-amino-2-[(3S)-3-methylmorpholin-4-yl]-4,5'-bipyrimidin-6-yl}amino)-3-methylpyrrolidin-1-yl]ethanone;
tert-butyl (3S)-3-[{2'-amino-2-[(3S)-3-methylmorpholin-4-yl]-4,5'-bipyrimidin-6-yl}(methyl)amino]-3-methylpyrrolidine-1-carboxylate;
tert-butyl (3S)-3-({2'-amino-2-[(3S)-3-methylmorpholin-4-yl]-4,5'-bipyrimidin-6-yl}amino)-3-methylpyrrolidine-1-carboxylate;
1-{(3S)-3-[{2'-amino-2-[(3S)-3-methylmorpholin-4-yl]-4,5'-bipyrimidin-6-yl}(methyl)amino]-3-methylpyrrolidin-1-yl}ethanone;
1-[(3S)-3-({2'-amino-2-[(3S)-3-methylmorpholin-4-yl]-4,5'-bipyrimidin-6-yl}amino)-3-methylpyrrolidin-1-yl]ethanone;
tert-butyl 3-{[2'-amino-2-(morpholin-4-yl)-4,5'-bipyrimidin-6-yl]amino}-3-(hydroxymethyl)pyrrolidine-1-carboxylate;
tert-butyl (3R)-3-{[2'-amino-2-(morpholin-4-yl)-4,5'-bipyrimidin-6-yl]amino}-3-(hydroxymethyl)pyrrolidine-1-carboxylate;
tert-butyl (3S)-3-{[2'-amino-2-(morpholin-4-yl)-4,5'-bipyrimidin-6-yl]amino}-3-(hydroxymethyl)pyrrolidine-1-carboxylate;
tert-butyl 3-{[2'-amino-2-(morpholin-4-yl)-4,5'-bipyrimidin-6-yl](methyl)amino}-3-(hydroxymethyl)pyrrolidine-1-carboxylate;
tert-butyl 3-{[2'-amino-2-(morpholin-4-yl)-4,5'-bipyrimidin-6-yl](methyl)amino}-3-(hydroxymethyl)pyrrolidine-1-carboxylate;
tert-butyl 3-{[2'-amino-2-(morpholin-4-yl)-4,5'-bipyrimidin-6-yl](methyl)amino}-3-(hydroxymethyl)pyrrolidine-1-carboxylate;
tert-butyl 3-{[2'-amino-2-(morpholin-4-yl)-4,5'-bipyrimidin-6-yl]amino}-3-ethylpyrrolidine-1-carboxylate;
[(3S)-3-{[2'-amino-2-(morpholin-4-yl)-4,5'-bipyrimidin-6-yl]amino}pyrrolidin-3-yl]methanol;
[(3R)-3-{[2'-amino-2-(morpholin-4-yl)-4,5'-bipyrimidin-6-yl]amino}pyrrolidin-3-yl]methanol;
1-[(3R)-3-{[2'-amino-2-(morpholin-4-yl)-4,5'-bipyrimidin-6-yl]amino}-3-(hydroxymethyl)pyrrolidin-1-yl]ethanone;
1-[(3S)-3-{[2'-amino-2-(morpholin-4-yl)-4,5'-bipyrimidin-6-yl]amino}-3-(hydroxymethyl)pyrrolidin-1-yl]ethanone;
[(3S)-3-{[2'-amino-2-(morpholin-4-yl)-4,5'-bipyrimidin-6-yl]amino}-1-(methylsulfonyl)pyrrolidin-3-yl]methanol;
methyl (3S)-3-{[2'-amino-2-(morpholin-4-yl)-4,5'-bipyrimidin-6-yl]amino}-3-(hydroxymethyl)pyrrolidine-1-carboxylate;
1-[(3S)-3-{[2'-amino-2-(morpholin-4-yl)-4,5'-bipyrimidin-6-yl]amino}-3-(hydroxymethyl)pyrrolidin-1-yl]-2-methylpropan-1-one;
tert-butyl (3S)-3-({2'-amino-2-[(3S)-3-methylmorpholin-4-yl]-4,5'-bipyrimidin-6-yl}amino)-3-(hydroxymethyl)pyrrolidine-1-carboxylate;
tert-butyl (3R)-3-{[2'-amino-2-(morpholin-4-yl)-4,5'-bipyrimidin-6-yl]amino}-3-ethylpyrrolidine-1-carboxylate;
tert-butyl (3S)-3-{[2'-amino-5-fluoro-2-(morpholin-4-yl)-4,5'-bipyrimidin-6-yl]amino}-3-(hydroxymethyl)pyrrolidine-1-carboxylate;
tert-butyl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate;
tert-butyl (3S)-3-{[2'-amino-2-(morpholin-4-yl)-4,5'-bipyrimidin-6-yl]amino}-3-methylpyrrolidine-1-carboxylate;
tert-butyl 3-{[2'-amino-2-(morpholin-4-yl)-4,5'-bipyrimidin-6-yl]amino}-3-(hydroxymethyl)azetidine-1-carboxylate;
1-[3-{[2'-amino-2-(morpholin-4-yl)-4,5'-bipyrimidin-6-yl]amino}-3-(hydroxymethyl)azetidin-1-yl]ethanone;
(3-{[2'-amino-2-(morpholin-4-yl)-4,5'-bipyrimidin-6-yl]amino}azetidin-3-yl)methanol;
propan-2-yl (3S)-3-{[2'-amino-2-(morpholin-4-yl)-4,5'-bipyrimidin-6-yl]amino}-3-(hydroxymethyl)pyrrolidine-1-carboxylate;
ethyl (3S)-3-{[2'-amino-2-(morpholin-4-yl)-4,5'-bipyrimidin-6-yl]amino}-3-(hydroxymethyl)pyrrolidine-1-carboxylate;
[(3S)-3-{[2'-amino-2-(morpholin-4-yl)-4,5'-bipyrimidin-6-yl]amino}-3-(hydroxymethyl)pyrrolidin-1-yl][(1S)-2,2-difluorocyclopropyl]methanone;
1-methylcyclopropyl (3S)-3-{[2'-amino-2-(morpholin-4-yl)-4,5'-bipyrimidin-6-yl]amino}-3-(hydroxymethyl)pyrrolidine-1-carboxylate;
(3S)-3-{[2'-amino-2-(morpholin-4-yl)-4,5'-bipyrimidin-6-yl]amino}-N-tert-butyl-3-(hydroxymethyl)pyrrolidine-1-carboxamide;
tert-butyl 3-({2'-amino-2-[(3S)-3-methylmorpholin-4-yl]-4,5-bipyrimidin-6-yl}amino)-3-(hydroxymethyl)azetidine-1-carboxylate;
(2R)-2-amino-1-[(3S)-3-{[2'-amino-2-(morpholin-4-yl)-4,5'-bipyrimidin-6-yl]amino}-3-(hydroxymethyl)pyrrolidin-1-yl]-3-methylbutan-1-one;
(2S)-2-amino-1-[(3S)-3-{[2'-amino-2-(morpholin-4-yl)-4,5'-bipyrimidin-6-yl]amino}-3-(hydroxymethyl)pyrrolidin-1-yl]-3-methylbutan-1-one;
[(3S)-3-{[2'-amino-2-(morpholin-4-yl)-4,5'-bipyrimidin-6-yl]amino}-1-(propan-2-ylsulfonyl)pyrrolidin-3-yl]methanol;
1-[3-({[2'-amino-2-[(3S)-3-methylmorpholin-4-yl]-4,5'-bipyrimidin-6-yl]amino})-3-(hydroxymethyl)azetidin-1-yl]ethanone;
[3-({2'-amino-2-[(3S)-3-methylmorpholin-4-yl]-4,5'-bipyrimidin-6-yl}amino)azetidin-3-yl]methanol;
(2R)-1-[(3S)-3-{[2'-amino-2-(morpholin-4-yl)-4,5'-bipyrimidin-6-yl]amino}-3-(hydroxymethyl)pyrrolidin-1-yl]-2-hydroxy-2-phenylethanone;

[(3S)-3-{[2'-amino-2-(morpholin-4-yl)-4,5'-bipyrimidin-6-yl]amino}-3-(hydroxymethyl)pyrrolidin-1-yl]-fluorocyclopropyl)methanone;
1-[(3S)-3-{[2'-amino-2-(morpholin-4-yl)-4,5'-bipyrimidin-6-yl]amino}-3-(hydroxymethyl)pyrrolidin-1-yl]-3-methylbutan-1-one;
methyl (3S)-3-{[2'-amino-2-(morpholin-4-yl)-4'-(trifluoromethyl)-4,5'-bipyrimidin-6-yl]amino}-3-(hydroxymethyl)pyrrolidine-1-carboxylate;
methyl (3S)-3-{[2'-amino-4'-methyl-2-(morpholin-4-yl)-4,5'-bipyrimidin-6-yl]amino}-3-(hydroxymethyl)pyrrolidine-1-carboxylate;
(2S)-1-[(3S)-3-{[2'-amino-2-(morpholin-4-yl)-4,5'-bipyrimidin-6-yl]amino}-3-(hydroxymethyl)pyrrolidin-1-yl]-2-hydroxy-2-phenylethanone;
1-[(3S)-3-{[2'-amino-2-(morpholin-4-yl)-4,5'-bipyrimidin-6-yl]amino}-3-(hydroxymethyl)pyrrolidin-1-yl]-3,3-dimethylbutan-1-one;
tert-butyl 3-{[2'-amino-2-(morpholin-4-yl)-4,5'-bipyrimidin-6-yl]amino}-3-(trifluoromethyl)pyrrolidine-1-carboxylate;
[(3S)-3-{[2'-amino-2-(morpholin-4-yl)-4,5'-bipyrimidin-6-yl]amino}-3-(hydroxymethyl)pyrrolidin-1-yl]pyridin-2-yl)methanone;
ethyl (3S)-3-({2'-amino-2-[(3S)-3-methylmorpholin-4-yl]-4,5'-bipyrimidin-6-yl}amino)-3-(hydroxymethyl)pyrrolidine-1-carboxylate;
methyl (3S)-3-({2'-amino-2-[(3S)-3-methylmorpholin-4-yl]-4,5'-bipyrimidin-6-yl}amino)-3-(hydroxymethyl)pyrrolidine-1-carboxylate;
propan-2-yl (3S)-3-({2'-amino-2-[(3S)-3-methylmorpholin-4-yl]-4,5'-bipyrimidin-6-yl}amino)-3-(hydroxymethyl)pyrrolidine-1-carboxylate;
[(3S)-3-{[2'-amino-2-(morpholin-4-yl)-4,5'-bipyrimidin-6-yl]amino}-1-(2,2-difluoroethyl)pyrrolidin-3-yl]methanol;
1-[(3S)-3-{[2'-amino-2-(morpholin-4-yl)-4,5'-bipyrimidin-6-yl]amino}-3-(hydroxymethyl)pyrrolidin-1-yl]-2-fluoro-2-methylpropan-1-one;
ethyl (3S)-3-{[2'-amino-5-fluoro-2-(morpholin-4-yl)-4,5'-bipyrimidin-6-yl]amino}-3-(hydroxymethyl)pyrrolidine-1-carboxylate;
propan-2-yl (3S)-3-{[2'-amino-5-fluoro-2-(morpholin-4-yl)-4,5'-bipyrimidin-6-yl]amino}-3-(hydroxymethyl)pyrrolidine-1-carboxylate;
[(3S)-3-{[2'-amino-2-(morpholin-4-yl)-4,5'-bipyrimidin-6-yl]amino}-1-(cyclopropylmethyl)pyrrolidin-3-yl]methanol;
methyl (3S)-3-{[2'-amino-5-fluoro-2-(morpholin-4-yl)-4,5'-bipyrimidin-6-yl]amino}-3-(hydroxymethyl)pyrrolidine-1-carboxylate;
[(3S)-3-{[2'-amino-2-(morpholin-4-yl)-4,5'-bipyrimidin-6-yl]amino}-3-(hydroxymethyl)pyrrolidin-1-yl](1-methyl-1H-imidazol-2-yl)methanone;
[(3S)-3-{[2'-amino-2-(morpholin-4-yl)-4,5'-bipyrimidin-6-yl]amino}-3-(hydroxymethyl)pyrrolidin-1-yl][(1R,2S)-2-fluorocyclopropyl]methanone;
[(3S)-3-{[2'-amino-2-(morpholin-4-yl)-4,5'-bipyrimidin-6-yl]amino}-3-(hydroxymethyl)pyrrolidin-1-yl][(1R,2R)-2-fluorocyclopropyl]methanone;
(3S)-3-{[2'-amino-2-(morpholin-4-yl)-4,5'-bipyrimidin-6-yl]amino}-3-(hydroxymethyl)-1'-methyl-1,3'-bipyrrolidin-2'-one;
propyl (3S)-3-{[2'-amino-2-(morpholin-4-yl)-4,5'-bipyrimidin-6-yl]amino}-3-(hydroxymethyl)pyrrolidine-1-carboxylate;
[(3S)-3-{[2'-amino-2-(morpholin-4-yl)-4,5'-bipyrimidin-6-yl]amino}-3-(hydroxymethyl)pyrrolidin-1-yl](pyrrolidin-1-yl)methanone;
2,2-difluoroethyl (3S)-3-{[2'-amino-2-(morpholin-4-yl)-4,5'-bipyrimidin-6-yl]amino}-3-(hydroxymethyl)pyrrolidine-1-carboxylate;
(3S)-3-{[2'-amino-2-(morpholin-4-yl)-4,5'-bipyrimidin-6-yl]amino}-3-(hydroxymethyl)-1,3'-bipyrrolidin-2'-one;
[(3S)-3-{[2'-amino-2-(morpholin-4-yl)-4,5'-bipyrimidin-6-yl]amino}-3-(hydroxymethyl)pyrrolidin-1-yl](1-methyl-1H-pyrazol-4-yl)methanone;
ethyl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate;
propan-2-yl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate;
3-[(3S)-3-{[2'-amino-2-(morpholin-4-yl)-4,5'-bipyrimidin-6-yl]amino}-3-(hydroxymethyl)pyrrolidin-1-yl]-1-methylpiperidin-2-one;
[(3S)-3-{[2'-amino-2-(morpholin-4-yl)-4,5'-bipyrimidin-6-yl]amino}-1-(pyridin-2-yl)pyrrolidin-3-yl]methanol;
[(3S)-3-{[2'-amino-2-(morpholin-4-yl)-4,5'-bipyrimidin-6-yl]amino}-3-(hydroxymethyl)pyrrolidin-1-yl](1H-imidazol-2-yl)methanone;
[(3S)-3-{[2'-amino-2-(morpholin-4-yl)-4,5'-bipyrimidin-6-yl]amino}-3-(hydroxymethyl)pyrrolidin-1-yl]pyrimidin-2-yl)methanone;
3-[(3S)-3-{[2'-amino-2-(morpholin-4-yl)-4,5'-bipyrimidin-6-yl]amino}-3-(hydroxymethyl)pyrrolidin-1-yl]piperidin-2-one;
[(3S)-3-{[2'-amino-2-(morpholin-4-yl)-4,5'-bipyrimidin-6-yl]amino}-3-(hydroxymethyl)pyrrolidin-1-yl]azetidin-1-yl)methanone;
[(3S)-3-{[2'-amino-2-(morpholin-4-yl)-4,5'-bipyrimidin-6-yl]amino}-3-(hydroxymethyl)pyrrolidin-1-yl](1H-pyrazol-4-yl)methanone;
[(3S)-3-{[4-(2-aminopyrimidin-5-yl)-6-(morpholin-4-yl)-1,3,5-triazin-2-yl]amino}-3-(hydroxymethyl)pyrrolidin-1-yl](1-fluorocyclopropyl)methanone;
[(3S)-3-{[2'-amino-2-(morpholin-4-yl)-4,5'-bipyrimidin-6-yl]amino}-3-(hydroxymethyl)pyrrolidin-1-yl](cyclopropyl)methanone;
cyclopropyl (3S)-3-{[2'-amino-2-(morpholin-4-yl)-4,5'-bipyrimidin-6-yl]amino}-3-(hydroxymethyl)pyrrolidine-1-carboxylate;
[(3R)-3-{[2'-amino-2-(morpholin-4-yl)-4,5'-bipyrimidin-6-yl]amino}-3-ethylpyrrolidin-1-yl](1-fluorocyclopropyl)methanone;
ethyl (3R)-3-{[2'-amino-2-(morpholin-4-yl)-4,5'-bipyrimidin-6-yl]amino}-3-ethylpyrrolidine-1-carboxylate;
[(3S)-3-({2'-amino-2-[(3S)-3-methylmorpholin-4-yl]-4,5'-bipyrimidin-6-yl}amino)-3-(hydroxymethyl)pyrrolidin-1-yl](cyclopropyl)methanone;
[(3S)-3-{[2'-amino-2-(morpholin-4-yl)-4,5'-bipyrimidin-6-yl]amino}-3-(hydroxymethyl)pyrrolidin-1-yl](3-fluoroazetidin-3-yl)methanone;
2-[(3S)-3-{[2'-amino-2-(morpholin-4-yl)-4,5'-bipyrimidin-6-yl]amino}-3-(hydroxymethyl)pyrrolidin-1-yl]-1-(azetidin-1-yl)ethanone;
2,2-difluoroethyl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate;
2-[(3S)-3-{[2'-amino-2-(morpholin-4-yl)-4,5'-bipyrimidin-6-yl]amino}-3-(hydroxymethyl)pyrrolidin-1-yl]-N,N-dimethylacetamide;

cyclopropyl (3S)-3-{[2'-amino-5-fluoro-2-(morpholin-4-yl)-4,5'-bipyrimidin-6-yl]amino}-3-(hydroxymethyl)pyrrolidine-1-carboxylate;
cyclopropyl (3S)-3-({2'-amino-2-[(3S)-3-methylmorpholin-4-yl]-4,5'-bipyrimidin-6-yl}amino)-3-(hydroxymethyl)pyrrolidine-1-carboxylate;
cyclopropyl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate;
[(3S)-3-({2'-amino-2-[(3S)-3-methylmorpholin-4-yl]-4,5'-bipyrimidin-6-yl}amino)-3-(hydroxymethyl)pyrrolidin-1-yl](oxetan-3-yl)methanone;
benzyl 3-{[2'-amino-2-(morpholin-4-yl)-4,5'-bipyrimidin-6-yl]amino}-3-(fluoromethyl)pyrrolidine-1-carboxylate;
1-[(3S)-3-{[2'-amino-5-fluoro-2-(morpholin-4-yl)-4,5'-bipyrimidin-6-yl]amino}-3-methylpyrrolidin-1-yl]ethanone;
1-[(3S)-3-{[2'-amino-5-fluoro-2-(morpholin-4-yl)-4,5'-bipyrimidin-6-yl]amino}-3-methylpyrrolidin-1-yl]-2-methylpropan-1-one;
tert-butyl (3S)-3-{[2'-amino-5-fluoro-2-(morpholin-4-yl)-4,5'-bipyrimidin-6-yl]amino}-3-methylpyrrolidine-1-carboxylate;
2-amino-1-[(3S)-3-{[2'-amino-5-fluoro-2-(morpholin-4-yl)-4,5'-bipyrimidin-6-yl]amino}-3-methylpyrrolidin-1-yl]-2-methylpropan-1-one;
tert-butyl 3-{[2'-amino-2-(morpholin-4-yl)-4,5'-bipyrimidin-6-yl]amino}-3-(fluoromethyl)pyrrolidine-1-carboxylate;
tert-butyl (3S)-3-({2'-amino-5-fluoro-2-[(3S)-3-methylmorpholin-4-yl]-4,5'-bipyrimidin-6-yl}amino)-3-(hydroxymethyl)pyrrolidine-1-carboxylate;
[(3S)-3-({2'-amino-5-fluoro-2-[(3S)-3-methylmorpholin-4-yl]-4,5'-bipyrimidin-6-yl}amino)pyrrolidin-3-yl]methanol;
ethyl (3S)-3-[(acetyloxy)methyl]-3-{[2'-amino-2-(morpholin-4-yl)-4,5'-bipyrimidin-6-yl]amino}pyrrolidine-1-carboxylate;
methyl (3S)-3-({2'-amino-5-fluoro-2-[(3S)-3-methylmorpholin-4-yl]-4,5'-bipyrimidin-6-yl}amino)-3-(hydroxymethyl)pyrrolidine-1-carboxylate;
[(3S)-3-{[2'-amino-5-fluoro-2-(morpholin-4-yl)-4,5'-bipyrimidin-6-yl]amino}-3-(hydroxymethyl)pyrrolidin-1-yl](1-fluorocyclobutyl)methanone;
[(3S)-3-({2'-amino-5-fluoro-2-[(3S)-3-methylmorpholin-4-yl]-4,5'-bipyrimidin-6-yl}amino)-3-(hydroxymethyl)pyrrolidin-1-yl](1-fluorocyclopropyl)methanone;
cyclopropyl (3S)-3-({2'-amino-5-fluoro-2-[(3S)-3-methylmorpholin-4-yl]-4,5'-bipyrimidin-6-yl}amino)-3-(hydroxymethyl)pyrrolidine-1-carboxylate;
ethyl (3S)-3-({4-(2-aminopyrimidin-5-yl)-6-[(3S)-3-methylmorpholin-4-yl]-1,3,5-triazin-2-yl}amino)-3-(hydroxymethyl)pyrrolidine-1-carboxylate;
2,2-difluoroethyl (3S)-3-({2'-amino-5-fluoro-2-[(3S)-3-methylmorpholin-4-yl]-4,5'-bipyrimidin-6-yl}amino)-3-(hydroxymethyl)pyrrolidine-1-carboxylate;
[(3S)-3-({2'-amino-5-fluoro-2-[(3S)-3-methylmorpholin-4-yl]-4,5'-bipyrimidin-6-yl}amino)-3-(hydroxymethyl)pyrrolidin-1-yl](cyclopropyl)methanone;
ethyl (3S)-3-{[2'-amino-2-(morpholin-4-yl)-4,5'-bipyrimidin-6-yl]amino}-3-(methoxymethyl)pyrrolidine-1-carboxylate;
N~6~-[(3S)-3-(methoxymethyl)pyrrolidin-3-yl]-2-(morpholin-4-yl)-4,5'-bipyrimidine-2',6-diamine;
tert-butyl 3-{[2'-amino-2-(morpholin-4-yl)-4,5'-bipyrimidin-6-yl]amino}-3-(hydroxymethyl)piperidine-1-carboxylate;
tert-butyl (3S)-3-({2'-amino-2-[(3S)-3-methylmorpholin-4-yl]-4,5'-bipyrimidin-6-yl}amino)-3-(fluoromethyl)pyrrolidine-1-carboxylate;
tert-butyl (3S)-3-{[6-(5-cyano-6-methylpyridin-3-yl)-2-(morpholin-4-yl)pyrimidin-4-yl]amino}-3-(hydroxymethyl)pyrrolidine-1-carboxylate;
tert-butyl (3S)-3-(hydroxymethyl)-3-{[2'-methyl-2-(morpholin-4-yl)-4,5'-bipyrimidin-6-yl]amino}pyrrolidine-1-carboxylate;
tert-butyl (3S)-3-{[6-(5-fluoro-6-methylpyridin-3-yl)-2-(morpholin-4-yl)pyrimidin-4-yl]amino}-3-(hydroxymethyl)pyrrolidine-1-carboxylate;
ethyl (3S)-3-{[6-(5-cyano-6-methylpyridin-3-yl)-2-(morpholin-4-yl)pyrimidin-4-yl]amino}-3-(hydroxymethyl)pyrrolidine-1-carboxylate;
ethyl (3S)-3-{[6-(5-fluoro-6-methylpyridin-3-yl)-2-(morpholin-4-yl)pyrimidin-4-yl]amino}-3-(hydroxymethyl)pyrrolidine-1-carboxylate;
ethyl (3S)-3-(hydroxymethyl)-3-{[2'-methyl-2-(morpholin-4-yl)-4,5'-bipyrimidin-6-yl]amino}pyrrolidine-1-carboxylate;
(3S)-3-{[2'-amino-2-(morpholin-4-yl)-4,5'-bipyrimidin-6-yl]amino}-N-(2,2-difluoroethyl)-3-(hydroxymethyl)pyrrolidine-1-carboxamide;
(3S)-3-{[2'-amino-5-fluoro-2-(morpholin-4-yl)-4,5'-bipyrimidin-6-yl]amino}-N-(2,2-difluoroethyl)-3-(hydroxymethyl)pyrrolidine-1-carboxamide;
(3S)-3-{[2'-amino-2-(morpholin-4-yl)-4,5'-bipyrimidin-6-yl]amino}-3-(hydroxymethyl)-N-(2,2,2-trifluoroethyl)pyrrolidine-1-carboxamide;
(3-{[2'-amino-2-(morpholin-4-yl)-4,5'-bipyrimidin-6-yl]amino}piperidin-3-yl)methanol;
(3S)-3-{[2'-amino-5-fluoro-2-(morpholin-4-yl)-4,5'-bipyrimidin-6-yl]amino}-3-(hydroxymethyl)-N-(2,2,2-trifluoroethyl)pyrrolidine-1-carboxamide;
(1-fluorocyclopropyl)[(3S)-3-(hydroxymethyl)-3-{[2'-methyl-2-(morpholin-4-yl)-4,5'-bipyrimidin-6-yl]amino}pyrrolidin-1-yl]methanone;
[(3S)-3-{[2'-amino-5-fluoro-2-(morpholin-4-yl)-4,5'-bipyrimidin-6-yl]amino}pyrrolidin-3-yl]methanol;
2,2-difluoroethyl (3S)-3-(hydroxymethyl)-3-{[2'-methyl-2-(morpholin-4-yl)-4,5'-bipyrimidin-6-yl]amino}pyrrolidine-1-carboxylate;
2-fluoroethyl (3S)-3-{[2'-amino-5-fluoro-2-(morpholin-4-yl)-4,5'-bipyrimidin-6-yl]amino}-3-(hydroxymethyl)pyrrolidine-1-carboxylate;
2,2,2-trifluoroethyl (3S)-3-{[2'-amino-5-fluoro-2-(morpholin-4-yl)-4,5'-bipyrimidin-6-yl]amino}-3-(hydroxymethyl)pyrrolidine-1-carboxylate;
2,2-difluoroethyl (3S)-3-{[2'-amino-2-(morpholin-4-yl)-4,5'-bipyrimidin-6-yl]amino}-3-(hydroxymethyl)piperidine-1-carboxylate;
tert-butyl (3R)-3-{[2'-amino-5-fluoro-2-(morpholin-4-yl)-4,5'-bipyrimidin-6-yl]amino}-3-(hydroxymethyl)piperidine-1-carboxylate;
tert-butyl (3S)-3-{[2'-amino-5-fluoro-2-(morpholin-4-yl)-4,5'-bipyrimidin-6-yl]amino}-3-(hydroxymethyl)piperidine-1-carboxylate;
[(3R)-3-{[2'-amino-5-fluoro-2-(morpholin-4-yl)-4,5'-bipyrimidin-6-yl]amino}piperidin-3-yl]methanol;
[(3S)-3-{[2'-amino-5-fluoro-2-(morpholin-4-yl)-4,5'-bipyrimidin-6-yl]amino}piperidin-3-yl]methanol;
1-[(3S)-3-{[2'-amino-5-fluoro-2-(morpholin-4-yl)-4,5'-bipyrimidin-6-yl]amino}-3-(hydroxymethyl)piperidin-1-yl]propan-1-one;

1-[(3R)-3-{[2'-amino-5-fluoro-2-(morpholin-4-yl)-4,5'-bipyrimidin-6-yl]amino}-3-(hydroxymethyl)piperidin-1-yl]propan-1-one;

2,2-difluoroethyl (3R)-3-{[2'-amino-5-fluoro-2-(morpholin-4-yl)-4,5'-bipyrimidin-6-yl]amino}-3-(hydroxymethyl)piperidine-1-carboxylate;

2,2-difluoroethyl (3S)-3-{[2'-amino-5-fluoro-2-(morpholin-4-yl)-4,5'-bipyrimidin-6-yl]amino}-3-(hydroxymethyl)piperidine-1-carboxylate;

1-[(3S)-3-{[2'-amino-5-fluoro-2-(morpholin-4-yl)-4,5'-bipyrimidin-6-yl]amino}-3-(hydroxymethyl)piperidin-1-yl]-2-methoxyethanone;

1-[(3R)-3-{[2'-amino-5-fluoro-2-(morpholin-4-yl)-4,5'-bipyrimidin-6-yl]amino}-3-(hydroxymethyl)piperidin-1-yl]-2-methoxyethanone;

1-[(3R)-3-{[2'-amino-5-fluoro-2-(morpholin-4-yl)-4,5'-bipyrimidin-6-yl]amino}-3-(hydroxymethyl)piperidin-1-yl]ethanone;

1-[(3S)-3-{[2'-amino-5-fluoro-2-(morpholin-4-yl)-4,5'-bipyrimidin-6-yl]amino}-3-(hydroxymethyl)piperidin-1-yl]ethanone;

methyl (3S)-3-{[2'-amino-5-fluoro-2-(morpholin-4-yl)-4,5'-bipyrimidin-6-yl]amino}-3-(hydroxymethyl)piperidine-1-carboxylate;

methyl (3R)-3-{[2'-amino-5-fluoro-2-(morpholin-4-yl)-4,5'-bipyrimidin-6-yl]amino}-3-(hydroxymethyl)piperidine-1-carboxylate;

[(3S)-3-{[2'-amino-5-fluoro-2-(morpholin-4-yl)-4,5'-bipyrimidin-6-yl]amino}-3-(hydroxymethyl)piperidin-1-yl](cyclopropyl)methanone;

[(3R)-3-{[2'-amino-5-fluoro-2-(morpholin-4-yl)-4,5'-bipyrimidin-6-yl]amino}-3-(hydroxymethyl)piperidin-1-yl](cyclopropyl)methanone;

[(3R)-3-{[2'-amino-5-fluoro-2-(morpholin-4-yl)-4,5'-bipyrimidin-6-yl]amino}-3-(hydroxymethyl)piperidin-1-yl](1-fluorocyclopropyl)methanone; and

[(3S)-3-{[2'-amino-5-fluoro-2-(morpholin-4-yl)-4,5'-bipyrimidin-6-yl]amino}-3-(hydroxymethyl)piperidin-1-yl](1-fluorocyclopropyl)methanone, or a pharmaceutically acceptable salt thereof.

Embodiments relate to a pharmaceutical composition comprising a compound of any of the embodiments of the compounds of formula (I), formula (II), formula (III), or formula (IV), or a pharmaceutically acceptable salt thereof, and a pharmaceutically acceptable carrier or diluent.

Embodiments relate to a combination of a compound of any of the embodiments of the compounds of formula (I), formula (II), formula (III), or formula (IV), or a pharmaceutically acceptable salt thereof, with an anti-tumor agent or with radiation therapy, for the treatment of cancer.

Embodiments relate to a combination of a compound of any of the embodiments of the compounds of formula (I), formula (II), formula (III), or formula (IV), or a pharmaceutically acceptable salt thereof, with an anti-tumor agent, for the treatment of cancer.

Embodiments relate to a method of treating abnormal cell growth in a mammal comprising administering to the mammal an amount of a compound of any of the embodiments of the compounds of formula (I), formula (II), formula (III), or formula (IV), or a pharmaceutically acceptable salt thereof, that is effective in treating abnormal cell growth.

Embodiments relate to the method of treating abnormal cell growth, wherein the abnormal cell growth is cancer.

Embodiments relate to the method of treating cancer, wherein the cancer is selected from the group consisting of basal cell cancer, medulloblastoma cancer, liver cancer, rhabdomyosarcoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system, primary central nervous system lymphoma, spinal axis tumors, brain stem glioma and pituitary adenoma, or a combination of one or more of the foregoing cancers.

Embodiments relate to the method of treating cancer, wherein the cancer is selected from the group consisting of lung cancer, cancer of the head or neck, colon cancer, breast cancer, and ovarian cancer, or a combination of one or more of the foregoing cancers.

DETAILED DESCRIPTION OF THE INVENTION

The following abbreviations may be used herein: AcOH (acetic acid); BOC (tert-butyloxycarbonyl); CDI (1,1'-carbonyldiimidazole); DCM (dichloromethane); DIPEA (N,N-diisopropylethylamine); DMF (N,N-dimethylformamide); DMSO (dimethylsulfoxide); dppf (1,1'-bis(diphenylphosphanyl)ferrocene); DTT ((2S,3S)-1,4-bis(sulfanyl)butane-2,3-diol); EDCI (1-Ethyl-3-(3-dimethylaminopropyl)carbodiimide); EDTA (2-({2-[bis(carboxymethyl)amino]ethyl}(carboxymethyl)amino)acetic acid); Et (ethyl); EtOH (ethanol); EtOAc (ethyl acetate); h (hour or hours); HATU (2-(7-aza-1H-benzotriazole-1-yl)-1,1,3,3-tetramethyluronium hexafluorophosphate); HEPES (2-[4-(2-hydroxyethyl)piperazin-1-yl]ethanesulfonic acid); hetAr (heteroaryl); HOBt (hydroxybenzotriazole); HPLC (high-performance liquid chromatography); iPrOH (isopropyl alcohol); KHMDS (potassium bis(trimethylsilyl)amide); LCMS (liquid chromatography-mass spectrometry); LiHMDS (lithium bis(trimethylsilyl)amide); Me (methyl); MeCN (acetonitrile); MeOH (methanol); min (minute or minutes); NaHMDS (sodium bis(trimethylsilyl)amide); N (normal); N/D (not determined); NMP (n-methylpyrrolidone); SEC (size exclusion chromatography); SFC (supercritical fluid chromatography); TBAF (tetrabutylammonium fluoride); TCEP (tris(2-carboxyethyl)phosphine); TEA (triethylamine); TFA (trifluoroacedic acid); THF (tetrahydrofuran); TMAF (tetramethyl ammonium fluoride); TMS-Cl (trimethylsilyl chloride); and Tris (tris(hydroxymethyl)aminomethane).

The term "halogen", as used herein, refers to a fluorine, chlorine, bromine, or iodine atom or fluoro, chloro, bromo, or iodo. Additionally, the term "halogen" refers to F, Cl, Br, or I. The terms fluorine, fluoro and F, for example, are understood to be equivalent herein.

The term "alkyl", as used herein, refers to saturated monovalent hydrocarbon radicals containing, in certain embodiments, from one to six, or from one to three carbon atoms, having straight or branched moieties. The term "$C_1$-$C_6$ alkyl" refers to an alkyl radical containing from one to six carbon atoms, having straight or branched moieties. The term "$C_1$-$C_6$ alkyl" includes within its definition the terms "$C_1$-$C_3$ alkyl" and "$C_1$-$C_4$ alkyl". Examples of alkyl groups include, but are not limited to, methyl, ethyl, propyl, isopropyl, butyl, isobutyl, sec-butyl, tert-butyl, pentyl, 2-pentyl, 3-pentyl, isopentyl, neopentyl, (R)-2-methylbutyl, (S)-2-methylbutyl, 3-methylbutyl, 2,3-dimethylpropyl, 2,3-dimethylbutyl, hexyl, and the like. Optional substitutions, unless otherwise specified, occur off any available carbon of the alkyl moiety.

The term "cycloalkyl", as used herein, refers to a monocyclic carbocyclic ring group containing, in certain embodiments, from three to four carbon atoms. Cycloalkyl groups include cyclopropyl, cyclobutyl.

The term "heterocycloalkyl", as used herein, refers to a non-aromatic, monocyclic ring group containing, in certain embodiments, a total of four to six ring atoms, in which one to two ring atoms are heteroatoms independently selected from nitrogen, oxygen, and sulfur, the remaining ring atoms being carbon, with the proviso that such ring systems may not contain two adjacent oxygen atoms or two adjacent sulfur atoms. Furthermore, such groups may be bonded to the remainder of the compounds of embodiments disclosed herein through either a carbon atom or a heteroatom, if possible. The terms "4-6 membered heterocycloalkyl" and "5-6 membered heterocycloalkyl", contains from four to six atoms and from five to six atoms, respectively. Examples of saturated heterocycloalkyl groups include, but are not limited to:

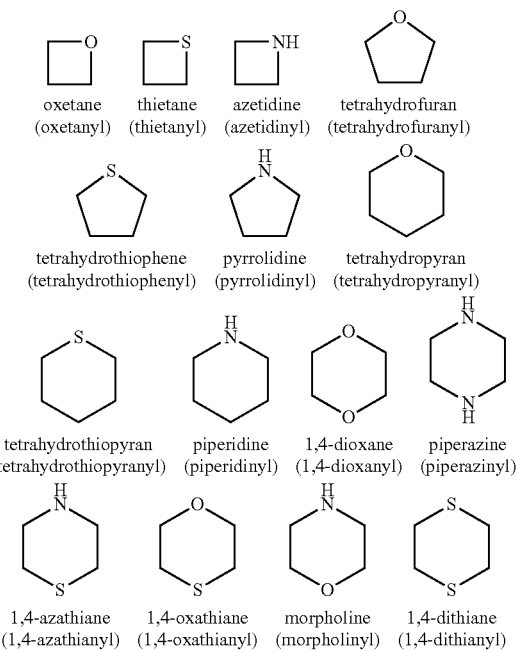

The term "heteroaryl, as used herein, refers to an aromatic monocyclic heterocyclic group having a total of 5 to 6 atoms in its ring, and containing from 2 to 5 carbon atoms and from one to three heteroatoms each independently selected from nitrogen, oxygen, and sulfur, with the proviso that the ring of said group does not contain two adjacent oxygen atoms or two adjacent sulfur atoms. The term "5-6 membered heteroaryl" contains from five to six ring atoms. Examples of heteroaryl groups include, but are not limited to, pyrrolyl, furyl, thienyl, imidazolyl, pyrazolyl, oxazolyl, isoxazolyl, isothiazolyl, triazolyl, oxadiazolyl, furazanyl, thiadiazolyl, thiazolyl, tetrazolyl, pyridinyl, pyrazinyl, pyrimidinyl, pyridazinyl, triazinyl, and the like.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

As used herein, an "effective" amount refers to an amount of a substance, agent, compound, or composition that is of sufficient quantity to result in a decrease in severity of disease symptoms, an increase in frequency and duration of disease symptom-free periods, or a prevention of impairment or disability due to the disease affliction—either as a single dose or according to a multiple dose regimen, alone or in combination with other agents or substances. One of ordinary skill in the art would be able to determine such amounts based on such factors as the subject's size, the severity of the subject's symptoms, and the particular composition or route of administration selected. The subject may be a human or non-human mammal (e.g. rabbit, rat, mouse, monkey or other lower-order primate).

Embodiments disclosed herein include isotopically-labeled compounds, which are identical to those recited in formula (I), formula (II), formula (III), or formula (IV) but for the fact that one or more atoms are replaced by an atom having an atomic mass or mass number different from the atomic mass or mass number usually found in nature. Examples of isotopes that can be incorporated into compounds of the embodiments disclosed herein include isotopes of hydrogen, carbon, nitrogen, oxygen, phosphorous, sulfur, fluorine and chlorine, such as but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein and pharmaceutically acceptable salts of said compounds which contain the aforementioned isotopes and/or other isotopes of other atoms are within the scope of the present embodiments. Certain isotopically-labeled compounds of the embodiments disclosed herein, for example, those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example, increased in vivo half-life or reduced dosage requirements and, hence, may be preferred in some circumstances. Isotopically-labeled compounds of embodiments disclosed herein can generally be prepared by carrying out the procedures disclosed in the Schemes and/or in the Examples and Preparations below, by substituting a readily available isotopically-labeled reagent for a non-isotopically-labeled reagent.

Some embodiments relate to the pharmaceutically acceptable salts of the compounds described herein. Pharmaceutically acceptable salts of the compounds described herein include the acid addition and base addition salts thereof.

Some embodiments also relate to the pharmaceutically acceptable acid addition salts of the compounds described herein. Suitable acid addition salts are formed from acids which form non-toxic salts. Non-limiting examples of suitable acid addition salts, i.e., salts containing pharmacologically acceptable anions, include, but are not limited to, the acetate, acid citrate, adipate, aspartate, benzoate, besylate, bicarbonate/carbonate, bisulphate/sulphate, bitartrate, borate, camsylate, citrate, cyclamate, edisylate, esylate, ethanesulfonate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methanesulfonate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, p-toluenesulfonate, tosylate, trifluoroacetate and xinofoate salts.

Additional embodiments relate to base addition salts of the compounds described herein. Suitable base addition salts are formed from bases which form non-toxic salts. Non-limiting examples of suitable base salts include the aluminium, arginine, benzathine, calcium, choline, diethylamine, diolamine, glycine, lysine, magnesium, meglumine, olamine, potassium, sodium, tromethamine and zinc salts.

The compounds described herein that are basic in nature are capable of forming a wide variety of salts with various inorganic and organic acids. The acids that may be used to prepare pharmaceutically acceptable acid addition salts of such basic compounds described herein are those that form non-toxic acid addition salts, e.g., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds described herein that include a basic moiety, such as an amino group, may form pharmaceutically acceptable salts with various amino acids, in addition to the acids mentioned above.

The chemical bases that may be used as reagents to prepare pharmaceutically acceptable base salts of those compounds of the compounds described herein that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of the embodiments described herein include all stereoisomers (e.g., cis and trans isomers) and all optical isomers of compounds described herein (e.g., R and S enantiomers), as well as racemic, diastereomeric and other mixtures of such isomers. While all stereoisomers are encompassed within the scope of our claims, one skilled in the art will recognize that particular stereoisomers may be preferred.

In some embodiments, the compounds described herein can exist in several tautomeric forms, including the enol and imine form, and the keto and enamine form and geometric isomers and mixtures thereof. All such tautomeric forms are included within the scope of the present embodiments. Tautomers exist as mixtures of a tautomeric set in solution. In solid form, usually one tautomer predominates. Even though one tautomer may be described, the present embodiments include all tautomers of the present compounds.

The present embodiments also include atropisomers of the compounds described herein. Atropisomers refer to compounds that can be separated into rotationally restricted isomers.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds described herein are known to one of skill in the art.

The term "solvate" is used herein to describe a molecular complex comprising a compound described herein and one or more pharmaceutically acceptable solvent molecules, for example, ethanol.

The compounds described herein may also exist in unsolvated and solvated forms. Accordingly, some embodiments relate to the hydrates and solvates of the compounds described herein.

Compounds described herein containing one or more asymmetric carbon atoms can exist as two or more stereoisomers. Where a compound described herein contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds described herein containing, for example, an imino, keto, or oxime group, or so-called valence tautomerism in compounds which contain an aromatic moiety. A single compound may exhibit more than one type of isomerism.

Included within the scope of the present embodiments are all stereoisomers, geometric isomers and tautomeric forms of the compounds described herein, including compounds exhibiting more than one type of isomerism, and mixtures of one or more thereof. Also included are acid addition or base salts wherein the counterion is optically active, for example, d-lactate or 1-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC) or SFC.

Alternatively, the racemate (or a racemic precursor) may be reacted with a suitable optically active compound, for example, an alcohol, or, in the case where a compound described herein contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; (5) benign and malignant cells of other proliferative diseases in which aberrant serine/threonine kinase activation occurs; (6) any tumors that proliferate by aberrant signaling, metabolic, epigenetic and transcriptional mechanism; and (7) benign and malignant cells of other proliferative diseases in which aberrant signaling, metabolic, epigenetic and transcriptional mechanism.

Further embodiments relate to methods of treating abnormal cell growth in a mammal. Additional embodiments relate to a method of treating abnormal cell growth in a mammal comprising administering to the mammal an amount of a compound described herein that is effective in treating abnormal cell growth.

In other embodiments, the abnormal cell growth is cancer.

In some embodiments, the cancer is selected from the group consisting of lung cancer, mesothelioma, bone cancer, pancreatic cancer, skin cancer, cancer of the head or neck, cutaneous or intraocular melanoma, uterine cancer, ovarian cancer, rectal cancer, cancer of the anal region, stomach cancer, hepatic carcinoma, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, hematology malignancy, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, glioblastoma, brain stem glioma, pituitary adenoma, or a combination of two or more of the foregoing cancers.

Additional embodiments relate to methods of treating cancer solid tumors in a mammal. Some embodiments relate to the treatment of cancer solid tumor in a mammal comprising administering to the mammal an amount of a compound described herein that is effective in treating said cancer solid tumor.

In other embodiments, the cancer solid tumor is breast, lung, colon, brain, prostate, stomach, pancreatic, ovarian, skin (melanoma), endocrine, uterine, testicular, or bladder.

Further embodiments relate to methods of treating abnormal cell growth in a mammal which comprises administering to said mammal an amount of a compound described herein that is effective in treating abnormal cell growth in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

More embodiments relate to pharmaceutical compositions for treating abnormal cell growth in a mammal comprising an amount of a compound described herein that is effective in treating abnormal cell growth, and a pharmaceutically acceptable carrier.

Additional embodiments relate to a method of treating abnormal cell growth in a mammal, including a human, comprising administering to the mammal an amount of a compound described herein, or a pharmaceutically acceptable salt, solvate, hydrate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In one embodiment the method comprises comprising administering to a mammal an amount of a compound described herein that is effective in treating said cancer solid tumor. In one preferred embodiment the solid tumor is breast, lung, colon, brain, prostate, stomach, pancreatic, ovarian, skin (melanoma), endocrine, uterine, testicular, and bladder cancer.

In another embodiment of said method, said abnormal cell growth is a benign proliferative disease, including, but not limited to, psoriasis, benign prostatic hypertrophy or restinosis.

Some embodiments relate to a method of treating abnormal cell growth in a mammal which comprises administering to said mammal an amount of a compound described herein, or a pharmaceutically acceptable salt, solvate, hydrate or prodrug thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

Additional embodiments relate to a pharmaceutical composition for treating abnormal cell growth in a mammal, including a human, comprising an amount of a compound described herein, or a pharmaceutically acceptable salt, solvate, hydrate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

Further embodiments relate to a method of treating abnormal cell growth in a mammal which comprises administering to said mammal an amount of a compound described herein, or a pharmaceutically acceptable salt, solvate, or hydrate thereof, that is effective in treating abnormal cell growth in combination with another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. Some embodiments contemplate a pharmaceutical composition for treating abnormal cell growth wherein the composition includes a compound described herein, or a pharmaceutically acceptable salt, solvate, or hydrate thereof, that is effective in treating abnormal cell growth, and another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

Yet more embodiments relate to a method of treating a disorder associated with angiogenesis in a mammal, including a human, comprising administering to said mammal an amount of a compound described herein, as defined above, or a pharmaceutically acceptable salt, solvate, hydrate or prodrug thereof, that is effective in treating said disorder in combination with one or more anti-tumor agents listed above. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus*.

Some embodiments relate to a method of (and to a pharmaceutical composition for) treating abnormal cell growth in a mammal which comprise an amount of a compound described herein, or a pharmaceutically acceptable salt, solvate, or hydrate thereof, in combination with an amount of one or more substances selected from antiangiogenesis agents, signal transduction inhibitors inhibitor (e.g., inhibiting the means by which regulatory molecules that govern the fundamental processes of cell growth, differentiation, and survival communicated within the cell), and antiproliferative agents, which amounts are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound described herein in the methods and pharmaceutical compositions described herein. Examples of useful COX-II inhibitors include CELEBREX™ (celecoxib), Bextra (valdecoxib), paracoxib, Vioxx (rofecoxib), and Arcoxia (etoricoxib). Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds described herein are AG-3340, RO 32-3555, RS 13-0830, and the following compounds:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R,3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

3-[4-(4-chloro-phenoxy)-benzenesulfonylamino]-tetrahydro-pyran-3-carboxylic acid hydroxyamide;

(2R,3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and 3-[4-(4-fluoro-phenoxy)-benzenesulfonylamino]-tetrahydro-furan-3-carboxylic acid hydroxyamide;

and pharmaceutically acceptable salts and solvates of said compounds.

VEGF inhibitors, for example, sutent and axitinib, can also be combined with a compound described herein. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883, 113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are 1M862 (Cytran Inc. of Kirkland, Wash., USA); Avastin, an anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound described herein. Such erbB2 inhibitors include Herceptin, 2C4, and pertuzumab. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the embodiments described herein are also described in U.S. Provisional Application No. 60/117,341, filed Jan. 27, 1999, and in U.S. Provisional Application No. 60/117,346, filed Jan. 27, 1999, both of which are herein incorporated by reference in their entirety. Other erbb2 receptor inhibitors include TAK-165 (Takeda) and GW-572016 (Glaxo-Wellcome).

Various other compounds, such as styrene derivatives, have also been shown to possess tyrosine kinase inhibitory properties, and some of tyrosine kinase inhibitors have been identified as erbB2 receptor inhibitors. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Other patent applications that refer to anti-cancer compounds are World Patent Application WO00/44728 (published Aug. 3, 2000), EP 1029853A1 (published Aug. 23, 2000), and WO01/98277 (published Dec. 12, 2001) all of which are incorporated herein by reference in their entirety.

Epidermal growth factor receptor (EGFR) inhibitors may be administered in combination with a compound of the presentation invention. Such EGFR inhibitors include gefinitib, erlotinib, icotinib, afatinib, dacomitinib, AZD9291, C01868, EGF816, and PF-06747775. Monoclonal antibody inhibitors of EGFR, such as cetuximab, may also be combined with a compound of the present invention.

PI3K inhibitors, such as PI3K beta inhibitors, may be administered in combination with a compound of the presentation invention.

Mammalian target of rapamycin (mTOR) inhibitors may be administered in combination with a compound of the presentation invention. Such mTOR inhibitors include rapamycin analogs and ATP competitive inhibitors.

c-Met inhibitors may be administered in combination with a compound of the presentation invention. Such c-Met inhibitors include crizotinib and ARQ-197. Monoclonal antibody inhibitors of c-Met, such as METMab, may also be combined with a compound of the present invention.

CDK inhibitors may be administered in combination with a compound of the presentation invention. Such CDK inhibitors include palbociclib.

MEK inhibitors may be administered in combination with a compound of the presentation invention. Such MEK inhibitors include trametinib and PD-325901.

PARP inhibitors may be administered in combination with a compound of the presentation invention.

JAK inhibitors may be administered in combination with a compound of the presentation invention.

An antagonist of a Programmed Death 1 protein (PD-1) may be administered in combination with a compound of the presentation invention.

Other antiproliferative agents that may be used with the compounds described herein include inhibitors of the enzyme farnesyl protein transferase and inhibitors of the receptor tyrosine kinase PDGFr, including the compounds disclosed and claimed in the following U.S. patent application Ser. No. 09/221,946 (filed Dec. 28, 1998); Ser. No. 09/454,058 (filed Dec. 2, 1999); Ser. No. 09/501,163 (filed Feb. 9, 2000); Ser. No. 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following U.S. provisional patent applications: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200834 (filed May 1, 2000). Each of the foregoing patent applications and provisional patent applications is herein incorporated by reference in their entirety.

A compound described herein may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present embodiments include those described in U.S. Provisional Application 60/113,647 (filed Dec. 23, 1998) which is herein incorporated by reference in its entirety.

A compound described herein may be applied as a sole therapy or may involve one or more other anti-tumor substances, for example those selected from, for example, mitotic inhibitors, for example vinblastine; alkylating agents, for example cis-platin, oxaliplatin, carboplatin and cyclophosphamide; anti-metabolites, for example 5-fluorouracil, capecitabine, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex (tamoxifen) or, for example anti-androgens such as Casodex (4'-cyano-3-(4-fluorophenylsulphonyl)-2-hydroxy-2-methyl-3'-(trifluoromethyl)propionanilide).

The compounds described herein may be used alone or in combination with one or more of a variety of anti-cancer agents or supportive care agents. For example, the compounds described herein may be used with cytotoxic agents, e.g., one or more selected from the group consisting of a camptothecin, irinotecan HCl (Camptosar), edotecarin, SU-11248, epirubicin (Ellence), docetaxel (Taxotere), paclitaxel, rituximab (Rituxan) bevacizumab (Avastin), imatinib mesylate (Gleevac), Erbitux, gefitinib (Iressa), and combinations thereof. Some embodiments also contemplate the use of the compounds described herein together with hormonal therapy, e.g., exemestane (Aromasin), Lupron, anastrozole (Arimidex), tamoxifen citrate (Nolvadex), Trelstar, and combinations thereof. Further, some embodiments provide a compound described herein alone or in combination with one or more supportive care products, e.g., a product selected from the group consisting of Filgrastim (Neupogen), ondansetron (Zofran), Fragmin, Procrit, Aloxi, Emend, or combinations thereof. Such conjoint treatment may be achieved by way of the simultaneous, sequential or separate dosing of the individual components of the treatment.

The compounds described herein may be used with anti-tumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of secondary agents that may be used with the compounds described herein.

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, carboplatin, eptaplatin, lobaplatin, nedaplatin, oxaliplatin or satrplatin.

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, gemcitabine, fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred antimetabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid.

Antibiotics include but are not limited to: aclarubicin, actinomycin D, amrubicin, annamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin or zinostatin.

Hormonal therapy agents, e.g., exemestane (Aromasin), Lupron, anastrozole (Arimidex), doxercalciferol, fadrozole, formestane, anti-estrogens such as tamoxifen citrate (Nolvadex) and fulvestrant, Trelstar, toremifene, raloxifene, lasofoxifene, letrozole (Femara), or anti-androgens such as bicalutamide, flutamide, mifepristone, nilutamide, Casodex® (4'-cyano-3-(4-fluorophenylsulphonyl)-2-hydroxy-2-methyl-3'-(trifluoromethyl)propionanilide) and combinations thereof.

Plant derived anti-tumor substances include for example those selected from mitotic inhibitors, for example vinblastine, docetaxel (Taxotere) and paclitaxel.

Cytotoxic topoisomerase inhibiting agents include one or more agents selected from the group consisting of aclarubicn, amonafide, belotecan, camptothecin, 10-hydroxycamptothecin, 9-am inocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, taflupo-side, and topotecan, and combinations thereof.

Immunologicals include interferons and numerous other immune enhancing agents. Interferons include interferon alpha, interferon alpha-2a, interferon, alpha-2b, interferon beta, interferon gamma-1a or interferon gamma-n1. Other agents include PF3512676, filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonerm in, tecleukin, thymalasin, tositumomab, Virulizin, Z-100, epratuzumab, mitumomab, oregovomab, pemtumomab, Provenge.

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, or ubenimex.

Other anticancer agents include alitretinoin, ampligen, atrasentan bexarotene, bortezomib. Bosentan, calcitriol, exisulind, finasteride, fotemustine, ibandronic acid, miltefosine, mitoxantrone, 1-asparaginase, procarbazine, dacarbazine, hydroxycarbamide, pegaspargase, pentostatin, tazarotne, TLK-286, Velcade, Tarceva, or tretinoin.

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain and Vitaxin.

Platinum-coordinated compounds include but are not limited to, cisplatin, carboplatin, nedaplatin, or oxaliplatin.

Camptothecin derivatives include but are not limited to camptothecin, 10-hydroxycamptothecin, 9-am inocamptothecin, irinotecan, SN-38, edotecarin, and topotecan.

Tyrosine kinase inhibitors include, for example, Iressa and SU5416.

Antibodies include, for example, Herceptin, Erbitux, Avastin, and Rituximab.

Interferons include, for example, interferon alpha, interferon alpha-2a, interferon, alpha-2b, interferon beta, interferon gamma-1a and interferon gamma-n1.

Biological response modifiers include agents that modify defense mechanisms of living organisms or biological responses, such as survival, growth, or differentiation of tissue cells to direct them to have anti-tumor activity. Such agents include, for example, krestin, lentinan, sizofiran, picibanil, and ubenimex.

Other antitumor agents include, for example, mitoxantrone, 1-asparaginase, procarbazine, dacarbazine, hydroxycarbamide, pentostatin, and tretinoin. Additionally, RAS-targeted cancer treatments may be combined with the compounds described herein.

Some embodiments also relate to a pharmaceutical composition comprising a compound of formula (I), formula (II), formula (III), or formula (IV), or a pharmaceutically acceptable salt or solvate thereof, as hereinbefore defined in association with a pharmaceutically acceptable adjuvant, diluent or carrier.

Further embodiments relate to a pharmaceutical composition which comprises mixing a compound of formula (I), formula (II), formula (III), or formula (IV), or a pharmaceutically acceptable salt or solvate thereof, as hereinbefore defined with a pharmaceutically acceptable adjuvant, diluent or carrier.

For the above-mentioned therapeutic uses the dosage administered will, of course, vary with the compound employed, the mode of administration, the treatment desired and the disorder indicated. The daily dosage of the compound formula (I), formula (II), formula (III), or formula (IV), or pharmaceutically acceptable salt thereof, may be in the range from 1 mg to 1 gram, preferably 1 mg to 250 mg, more preferably 1 mg to 100 mg.

The present embodiments also encompass sustained release compositions.

Administration of the compounds described herein (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The active compound may be applied as a sole therapy or may involve one or more other anti-tumor substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex® (tamoxifen) or, for example anti-androgens such as Casodex® (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound described herein as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The examples and preparations provided below further illustrate and exemplify the compounds described herein and methods of preparing such compounds. The scope of the embodiments described herein is not limited in any way by the following examples and preparations. In the following examples, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

In the examples shown, salt forms were occasionally isolated as a consequence of the mobile phase additives during HPLC based chromatographic purification. In these cases, salts such as formate, trifluorooacetate and acetate were isolated and tested without further processing. It will be recognized that one of ordinary skill in the art will be able to realize the free base form by standard methodology (such as using ion exchange columns, or performing simple basic extractions using a mild aqueous base).

In general, the compounds described herein may be prepared by processes known in the chemical arts, particularly in light of the description contained herein. Certain processes for the manufacture of the compounds described herein are provided as further features of the embodiments and are illustrated in the reaction schemes provided below and in the experimental section.

Unless stated otherwise, the variables in Schemes A and B have the same meanings as defined herein.

Scheme A:

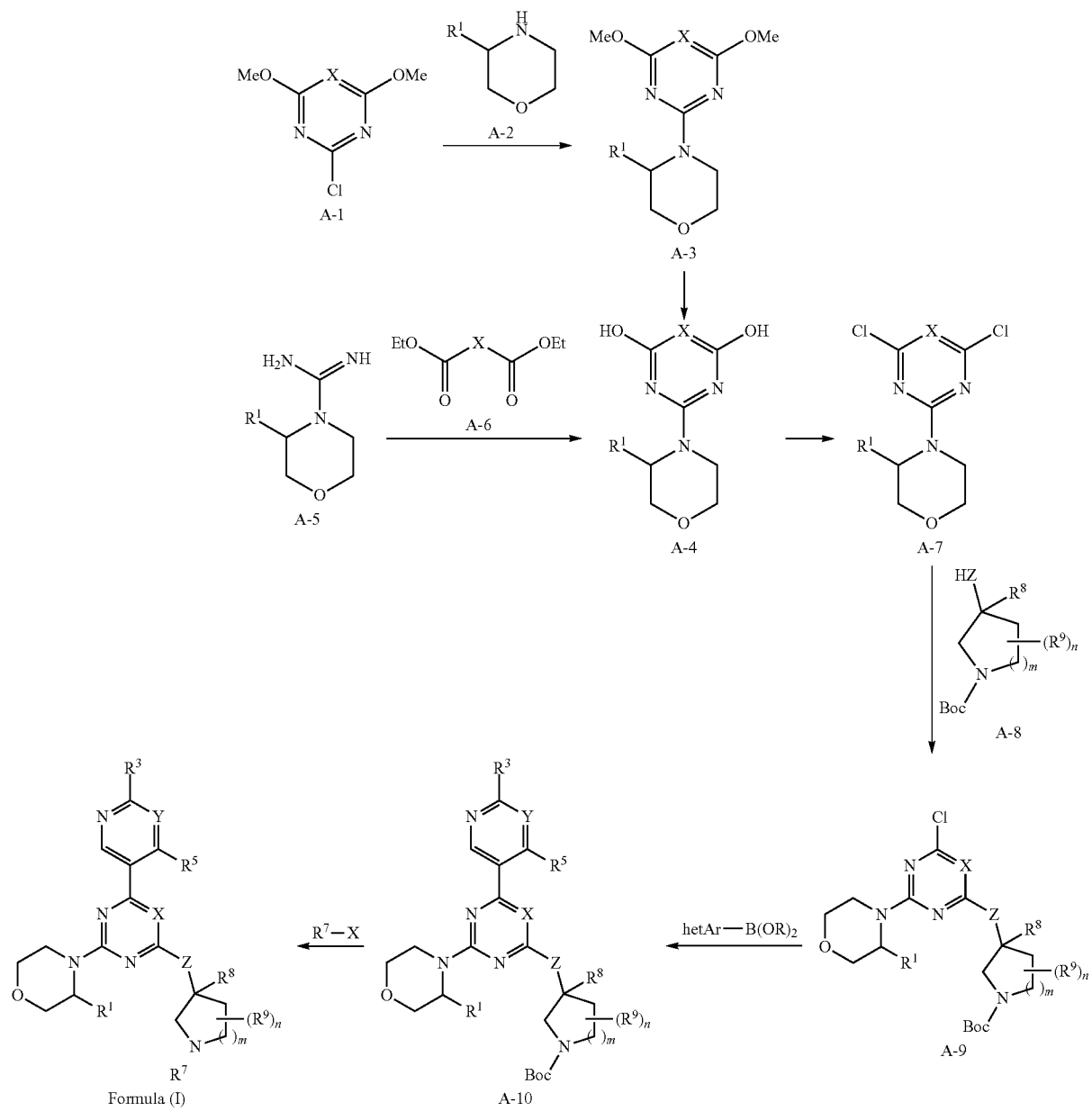

As exemplified in Scheme A, a pyrimidine A-1 is subjected to chlorine displacement with an amine A-2 in the presence of a suitable base (such as DIPEA, NaH, $K_2CO_3$, or CsF) in a suitable solvent (such as DMSO, acetonitrile, NMP, THF, or DMF) to afford A-3. A-3 is treated under demethylation conditions known in the art with sodium iodide and TMS-Cl in acetonitrile to provide A-4. Alternatively, as exemplified in Scheme A, a guanidine A-5 and a malonate A-6 are subjected to a condensation to afford A-4. A-4 is treated with a chlorinating reagent, such as $POCl_3$, to afford A-7. A-7 is subjected to selective chlorine displacement with an amine or alcohol A-8 in a presence of a suitable base (NaH, NaHMDS, KHMDS, LiHMDS, $K_2CO_3$, TBAF, TMAF, DIPEA or 2,6-lutidine) in a suitable solvent (such as DMSO, acetonitrile, NMP, THF, or DMF) to afford A-9. A-9 is treated under Suzuki cross-coupling conditions known in the literature with a boronic acid or a boronic ester to yield A-10. The N-Boc group of A-10 may be deprotected under acidic conditions (such as HCl or TFA) and the resultant amine may be subjected to amide, carbamate, urea, sulfonamide or N-alkyl formation to yield formula (I). Amide formation can be achieved using a suitable amide coupling agent (such as CDI, EDCI, HATU) in the presence of a suitable base (such as DIPEA, TEA) and an appropriate carboxylic acid. Carbamate formation can be achieved using an appropriate chloroformate in the presence of a suitable base (such as DIPEA or TEA) or using an appropriate alcohol in the presence of bis(pentafluorophenyl)carbonate, CDI, phosgene or triphosgene and a suitable base (such as DIPEA or TEA). Urea formation can be achieved by using an appropriate isocyanate in the presence of a suitable base (such as TEA), or in the presence of CDI, triphosgene or phosgene and an amine in the presence of a suitable base (such as sodium carbonate, sodium bicarbonate, or TEA). Sulfonamide formation can be achieved with a sulfonyl chloride in the presence of a suitable base (such as DIPEA or TEA). These amine functionalizations may be performed either before (with A-9) or after (with A-10) the Suzuki cross-coupling step.

As exemplified in Scheme B, a triazine B-1 is subjected to chlorine displacement with an amine A-2 in the presence of a suitable base (such as DIPEA, NaH, NaHCO$_3$, K$_2$CO$_3$, or CsF) in a suitable solvent (such as DMSO, acetonitrile, NMP, THF, or DMF) to afford B-2. B-2 is subjected to selective chlorine displacement with an amine A-8 in a presence of a suitable base (NaH, NaHCO$_3$, DIPEA, CsF or Scheme B:

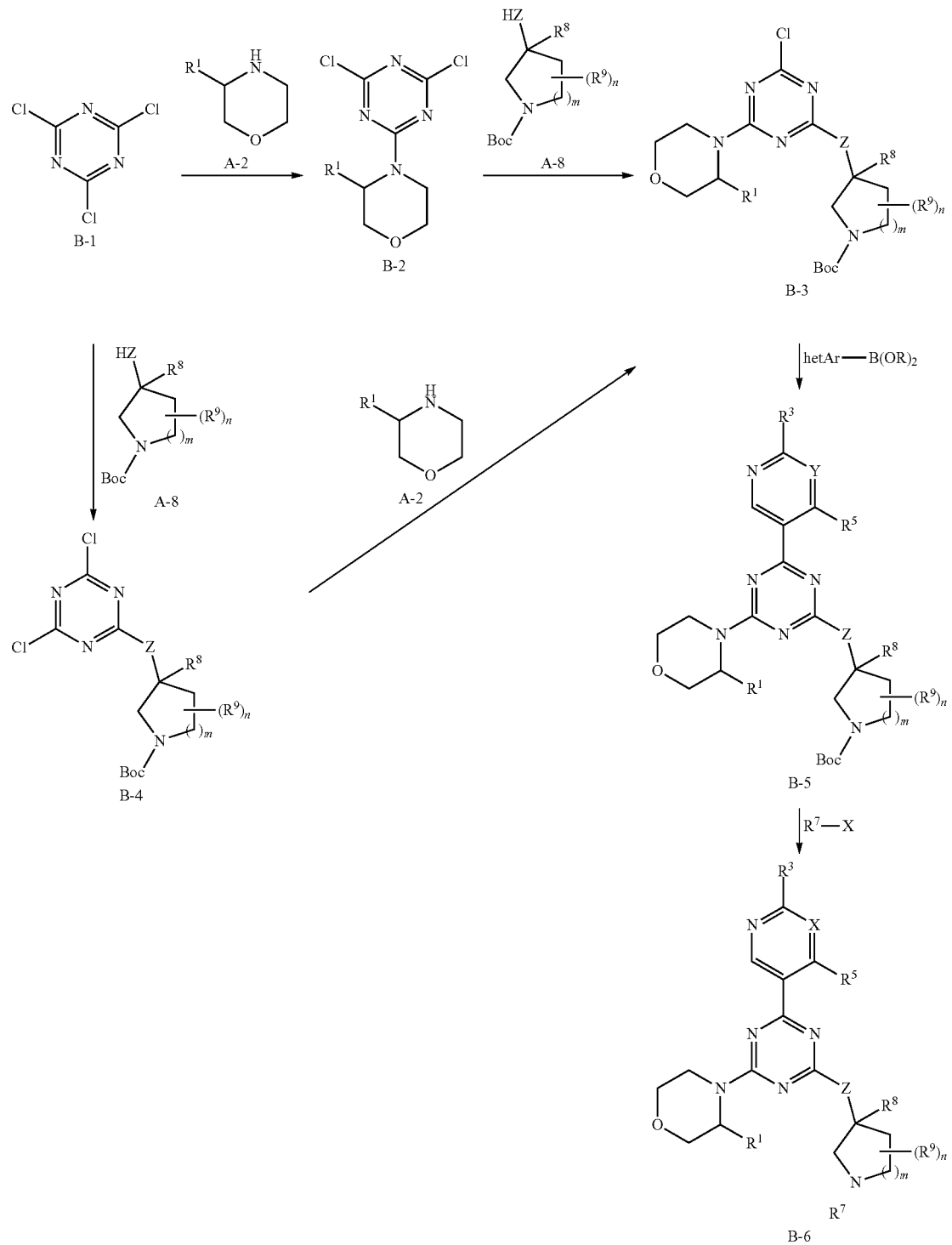

2,6-lutidine) in a suitable solvent (such as acetonitrile, THF, DMF, NMP, DMSO) to afford B-3. Alternatively, B-1 is subjected to chlorine displacement with an amine A-8 in the presence of a suitable base (such as NaH, NaHCO₃, DIPEA, CsF or 2,6-lutidine) in a suitable solvent (such as acetonitrile, DMSO, NMP, THF, or DMF) to afford B-4. B-4 is subjected to selective chlorine displacement with an amine A-2 in a presence of a suitable base (NaH, NaHCO₃, DIPEA, CsF, or 2,6-lutidine) in a suitable solvent (such as acetonitrile, THF, DMF, NMP, DMSO) to afford B-3. B-3 is treated under Suzuki cross-coupling conditions known in the literature with a boronic acid or a boronic ester to yield B-5. The N-Boc group of B-5 may be deprotected as described in Scheme A and the resultant amine subjected to amide, carbamate, urea, sulfonamide, or N-alkyl formation conditions as described above to yield B-6. These amine functionalizations may be performed either before (with B-3) or after (with B-6) the Suzuki cross-coupling step.

EXAMPLES

Example 1 (Scheme A): Preparation of [(3S)-3-{[2'-amino-5-fluoro-2-(morpholin-4-yl)-4,5'-bipyrimidin-6-yl]amino}-3-(hydroxymethyl)pyrrolidin-1-yl](1-fluorocyclopropyl)methanone

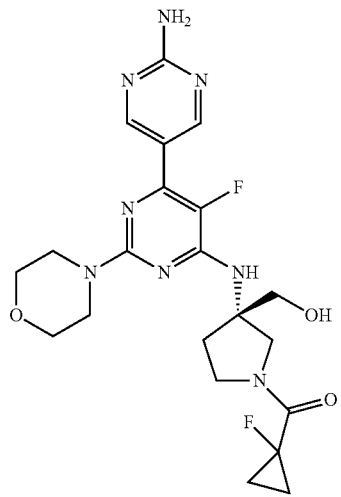 [SMILES: Nc1ncc(-c2nc(N3CCOCC3)nc(N[C@@]3(CO)CCN(C(=O)C4(F)CC4)C3)c2F)cn1]

Step 1: Preparation of tert-butyl (3S)-3-{[6-chloro-5-fluoro-2-(morpholin-4-yl)pyrimidin-4-yl]amino}-3-(hydroxymethyl)pyrrolidine-1-carboxylate

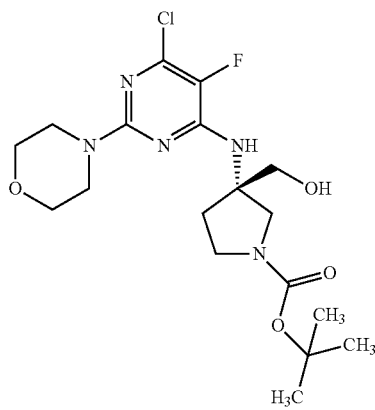 [SMILES: CC(C)(C)OC(=O)N1CC[C@](CO)(Nc2nc(N3CCOCC3)nc(Cl)c2F)C1]

The product of Preparation 1, 4-(4,6-dichloro-5-fluoro-pyrimidin-2-yl)morpholine (2.00 g, 7.93 mmol), tetramethylammonium fluoride (813 mg, 8.73 mmol) and tert-butyl (3S)-3-amino-3-(hydroxymethyl)pyrrolidine-1-carboxylate (2.23 g, 10.3 mmol) were suspended in NMP (13.9 mL) and diisopropylethylamine (2.71 mL, 15.9 mmol) under nitrogen and the yellow mixture was heated at 70° C. for 18 h. The mixture was cooled to room temperature, diluted with water (20 mL) and extracted with EtOAc (3×15 mL). The combined organic phases were washed with brine (2×25 mL), dried over Na₂SO₄, filtered and concentrated. The crude product was purified over silica gel (20-50% EtOAc/heptanes) to give the title compound (2.54 g, 74%) as a foamy white solid. ¹H NMR (400 MHz, 80° C., DMSO-d₆) δ 6.91 (s, 1H), 4.76 (t, J=5.9 Hz, 1H), 3.80-3.59 (m, 7H), 3.57-3.46 (m, 5H), 3.42-3.27 (m, 2H), 2.37-2.27 (m, 1H), 2.18-2.08 (m, 1H), 1.40 (s, 9H); m/z (APCI+) for $C_{18}H_{27}ClFN_6O_4$ 432.2 (M+H)⁺.

Step 2: Preparation of tert-butyl (3S)-3-{[2'-amino-5-fluoro-2-(morpholin-4-yl)-4,5'-bipyrimidin-6-yl]amino}-3-(hydroxymethyl)pyrrolidine-1-carboxylate

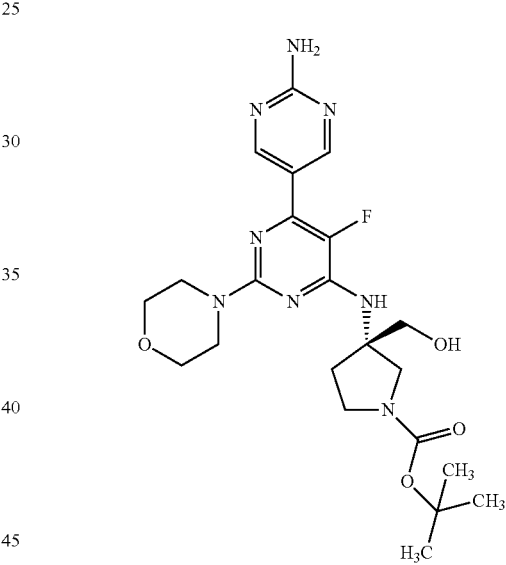

tert-Butyl (3S)-3-{[6-chloro-5-fluoro-2-(morpholin-4-yl)pyrimidin-4-yl]amino}-3-(hydroxymethyl)pyrrolidine-1-carboxylate (572 mg, 1.32 mmol), 5-(4,4,5,5-tetramethyl-1,3,2-dioxaborolan-2-yl)pyrimidin-2-amine (381 mg, 1.72 mmol) and 3 M aqueous potassium carbonate solution (1.77 mL) were suspended in 1,4-dioxane (13.2 mL). Argon was bubbled into the mixture, [1,1'-bis(diphenylphosphino)ferrocene]palladium(II) dichloride (96.9 mg, 0.132 mmol) was added, the reaction vessel was sealed and heated at 120° C. in a microwave reactor for 45 min. The reaction mixture was partitioned between dichloromethane and 1 M aqueous ammonium chloride. The organic layer was separated, dried with Na₂SO₄, filtered and concentrated. The residue was dissolved in dichloromethane (26 mL) and isopropanol (13 mL) and the solvent was removed on a rotary evaporator in a 60° C. water bath until most of the dichloromethane had distilled over (without vacuum). The flask was removed from the heating bath and allowed to cool to room temperature. The resulting suspension was cooled to 0° C., filtered and washed with cold isopropanol. The precipitate was placed in a 50° C. vacuum oven until a constant weight was obtained to give the title compound (429 mg, 66%) as a fluffy off-white solid. ¹H NMR (400 MHz, 80° C., DMSO-d₆) δ 8.77 (s, 2H), 6.74 (s, 2H), 6.50 (s, 1H), 4.73 (t, J=5.8 Hz, 1H), 3.82 (d, J=11.3 Hz, 1H), 3.80-3.74 (m, 1H), 3.74-3.69 (m, 1H), 3.69-3.64 (m, 4H), 3.64-3.57 (m, 4H), 3.52 (d, J=11.5 Hz, 1H), 3.45-3.37 (m, 1H), 3.37-3.27 (m, 1H), 2.44-2.34 (m, 1H), 2.15 (ddd, J=12.9, 8.0, 6.4 Hz, 1H), 1.41 (s, 9H); m/z (APCI+) for C₂₂H₃₁FN₈O₄ 491.2 (M+H)⁺.

Step 3: Preparation of [(3S)-3-{[2'-amino-5-fluoro-2-(morpholin-4-yl)-4,5'-bipyrimidin-6-yl]amino}pyrrolidin-3-yl]methanol trihydrochloride

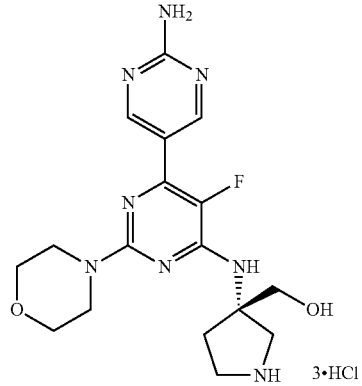 [SMILES: Nc1ncc(-c2nc(N3CCOCC3)nc(N[C@@]3(CO)CCNC3)c2F)cn1]

Hydrochloric acid in 1,4-dioxane (4.33 mL, 4M) was added to a suspension tert-butyl (3S)-3-{[2'-amino-5-fluoro-2-(morpholin-4-yl)-4,5'-bipyrimidin-6-yl]amino}-3-(hydroxymethyl)pyrrolidine-1-carboxylate (425 mg, 0.866 mmol) in EtOAc (4.33 mL). After 18 h, the reaction mixture was diluted with toluene and concentrated by rotary evaporation. The residue was dissolved in MeOH and concentrated by rotary evaporation to give the title compound (455 mg, >99%) as an off-white solid which was used directly in the next step.

Step 4: Preparation of [(3S)-3-{[Z-amino-5-fluoro-2-(morpholin-4-yl)-4,5'-bipyrimidin-6-yl]amino}-3-(hydroxymethyl)pyrrolidin-1-yl](1-fluorocyclopropyl)methanone

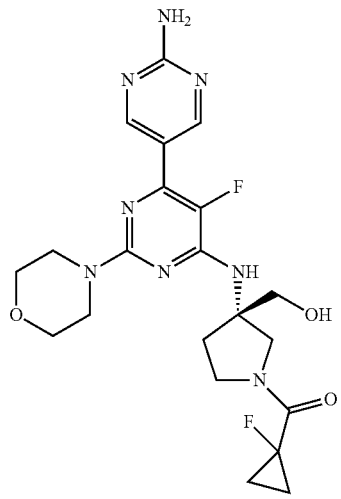 [SMILES: Nc1ncc(-c2nc(N3CCOCC3)nc(N[C@@]3(CO)CCN(C(=O)C4(F)CC4)C3)c2F)cn1]

[(3S)-3-{[2'-Amino-5-fluoro-2-(morpholin-4-yl)-4,5'-bipyrimidin-6-yl]amino}pyrrolidin-3-yl]methanol trihydrochloride (144 mg, 0.216 mmol) was suspended in DCM (4.32 mL) and diisopropylethylamine (140 mg, 1.08 mmol) was added dropwise, followed by 1-fluorocyclopropanecarboxylic acid (27.0 mg, 0.259 mmol). The reaction mixture was cooled to −30° C. and HOBt (35 mg, 0.259 mmol) was added followed by EDCI (49.7 mg, 0.259 mmol). The reaction mixture was stirred for 10 min and allowed to warm to room temperature. After 3 h, the reaction mixture was concentrated under reduced pressure and the residue purified by preparative HPLC (Waters Xbridge C18, 30×250 mm, 5 μm particle size; Column Temperature 60° C., Solvent A: Water with 0.1% acetic acid, Solvent B: Acetonitrile with 0.1% acetic acid, Gradient: 0% B for 5 min, 0-20% B in 5-25 min, 95% B 25-30 min; flow rate 8 mL/min) to give the title compound (52.9 mg, 51%) as a white solid. ¹H NMR (400 MHz, 80° C., DMSO-d₆) δ 8.78 (s, 2H), 6.74 (s, 2H), 6.60 (s, 1H), 4.78 (t, J=5.8 Hz, 1H), 3.87-3.75 (m, 4H), 3.71-3.57 (m, 10H), 2.27-2.16 (m, 1H), 1.28-1.11 (m, 4H); m/z (APCI+) for C₂₁H₂₆F₂N₈O₃ 477.2 (M+H)⁺.

Example 2 (Scheme A): Preparation of 2,2-difluoroethyl (3S)-3-{[2'-amino-5-fluoro-2-(morpholin-4-yl)-4,5'-bipyrimidin-6-yl]amino}-3-(hydroxymethyl)pyrrolidine-1-carboxylate

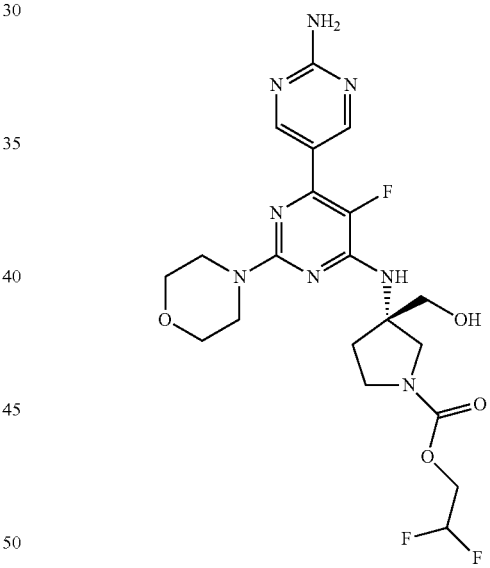

Bis(perfluorophenyl) carbonate (375 mg, 0.951 mmol) was added to a solution of 2,2-difluoroethan-1-ol (85.1 mg, 1.04 mmol) and triethylamine (105 mg, 1.04 mmol) in tetrahydrofuran (4.32 mL). After 1.75 h, this solution was added dropwise to a suspension of the product of Example 1, step 3, [(3S)-3-{[2'-amino-5-fluoro-2-(morpholin-4-yl)-4,5'-bipyrimidin-6-yl]amino}pyrrolidin-3-yl]methanol trihydrochloride (432.0 mg, 0.864 mmol) and triethylamine (440 mg, 4.32 mmol) in dichloromethane (17.3 mL) and isopropanol (1.73 mL). After 45 h, the reaction mixture was filtered and washed with isopropanol. The precipitate was suspended in dichloromethane and MeOH with trifluoroacetic acid (0.200 mL, 2.61 mmol). Silica gel was added and the mixture was concentrated to dryness by rotary evaporation. This material was purified by silica gel chromatography using gradient elution of (7 M ammonia in MeOH) in dichloromethane (0-10%) to give the title compound (223 mg, 52%) as an off-white solid. ¹H NMR (400 MHz, 80° C., DMSO-d₆) δ 8.77 (s, 2H), 6.74 (s, 2H), 6.58 (s, 1H), 6.17 (tt, J=54.8, 2.9 Hz, 1H), 4.77 (t, J=5.7 Hz, 1H), 4.27 (td, J=15.1, 3.1 Hz, 2H), 3.91 (d, J=11.6 Hz, 1H), 3.81-3.72 (m, 2H), 3.70-3.64 (m, 4H), 3.64-3.60 (m, 5H), 3.55-3.38 (m, 2H), 2.47-2.38 (m, 1H), 2.20 (dt, J=13.5, 7.0 Hz, 1H); m/z (APCI+) for C₂₀H₂₅F₃N₈O₄ 499.1 (M+H)⁺; [α]_D²¹=+8.3° (c=0.3, DMSO-d₆).

Example 3 (Scheme A): Preparation of 2,2-difluoroethyl (3S)-3-{[2'-amino-5-fluoro-2-(morpholin-4-yl)-4,5'-bipyrimidin-6-yl]amino}-3-[(phosphonooxy)methyl]pyrrolidine-1-carboxylate

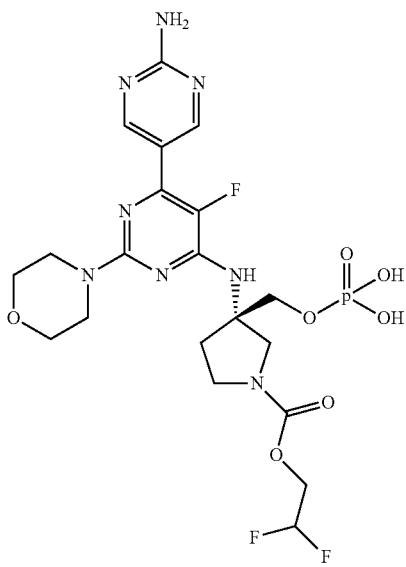

To a suspension of 2,2-difluoroethyl (3S)-3-{[2'-amino-5-fluoro-2-(morpholin-4-yl)-4,5'-bipyrimidin-6-yl]amino}-3-(hydroxymethyl)pyrrolidine-1-carboxylate (240 mg, 0.48 mmol) suspended in acetonitrile (3 mL) was added pyrophosphoryl chloride (618 mg, 2.41 mmol) at 0° C. The mixture was stirred for 1 h. Ice was added while rapidly stirring, and the mixture was allowed to warm to room temperature. The solvent was removed under reduced pressure and the residue was purified by preparative HPLC (Waters Xbridge C18, 30×250 mm, 5 μm particle size; Column Temperature 60° C., Solvent A: Water with 0.1% acetic acid, Solvent B: Acetonitrile with 0.1% acetic acid, Gradient: 0% B for 5 min, 0-20% B in 5-25 min, 95% B 25-30 min; flow rate 8 mL/min) and lyophilized to give 184 mg (66%) of the title compound as a white solid. ¹H NMR (400 MHz, 80° C., CD₃OD) δ 8.69 (s, 2H), 6.94-6.88 (m, 1H), 6.73 (s, 2H), 6.24-5.95 (m, 1H), 4.24-4.11 (m, 4H), 3.87-3.85 (m, 1H), 3.60-3.49 (m, 6H), 3.44-3.30 (m, 3H), 2.19-2.08 (m, 1H); m/z (ESI+) for C₂₀H₂₆F₃N₈O₇P 578.8 (M+H)⁺.

Examples 4, 5 and 6 (Scheme A): Preparation of methyl 3-{[2'-amino-2-(morpholin-4-yl)-4,5'-bipyrimidin-6-yl]amino}-3-(hydroxymethyl)piperidine-1-carboxylate (racemate and enantiomers)

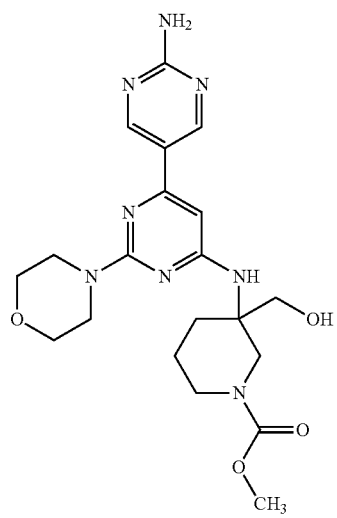 [SMILES: COC(=O)N1CCCC(CO)(Nc2cc(-c3cnc(N)nc3)nc(N3CCOCC3)n2)C1]

Step 1: Preparation of tert-butyl 3-{[6-chloro-2-(morpholin-4-yl)pyrimidin-4-yl]amino}-3-(hydroxymethyl)piperidine-1-carboxylate

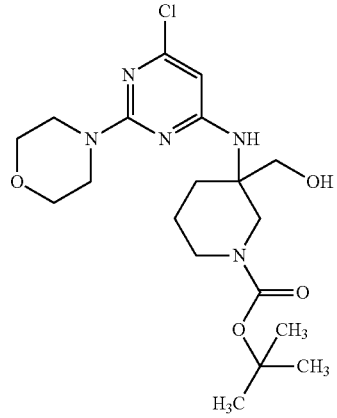 [SMILES: CC(C)(C)OC(=O)N1CCCC(CO)(Nc2cc(Cl)nc(N3CCOCC3)n2)C1]

To a vial containing 4-(4,6-dichloro-pyrimidin-2-yl)-morpholine (550 mg, 2.34 mmol) and the product of Preparation 5, tert-butyl 3-amino-3-(hydroxymethyl)piperidine-1-carboxylate (824 mg, 3.58 mmol), in NMP (11 mL) was added 2,6-lutidine (0.88 mL, 7.05 mmol). The mixture was heated at 110° C. for 8 days. The crude product was purified via reversed phase HPLC (Column: XBridge C18 30×250 mm at 60° C. eluting with 0%-35% of H₂O with 0.1% AcOH to CH₃CN with 0.1% AcOH over 25 min) to give the title compound (268 mg, 27%). ¹H NMR (400 MHz, DMSO-d₆) δ 6.28 (br s, 1H), 5.98 (s, 1H), 4.27-4.14 (m, 1H), 3.82-3.76 (m, 1H), 3.74-3.68 (m, 1H), 3.66-3.56 (m, 8H), 3.25-3.16 (m, 1H), 3.04-2.92 (m, 2H), 2.00-1.91 (m, 1H), 1.81-1.58 (m, 2H), 1.52-1.43 (m, 1H), 1.43-1.37 (m, 1H), 1.30 (s, 9H); m/z (APCI+) for C₁₉H₃₀ClN₆O₄ 428.2 (M+H)⁺.

Step 2: Preparation of tert-butyl 3-{[2'-amino-2-(morpholin-4-yl)-4,5'-bipyrimidin-6-yl]amino}-3-(hydroxymethyl)piperidine-1-carboxylate

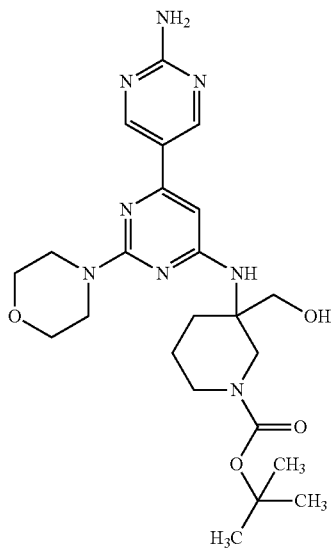 [SMILES: CC(C)(C)OC(=O)N1CCCC(CO)(Nc2cc(-c3cnc(N)nc3)nc(N3CCOCC3)n2)C1]

To a solution of tert-butyl 3-{[6-chloro-2-(morpholin-4-yl)pyrimidin-4-yl]amino}-3-(hydroxymethyl)piperidine-1-carboxylate (265 mg, 0.62 mmol) and 5-(4,4,5,5-tetramethyl-1,3,2-dioxaborolan-2-yl)pyrimidin-2-amine (178 mg, 0.806 mmol) in 1,4-dioxane (3 mL) was added 1M aqueous $Na_2CO_3$ (1.9 mL) and nitrogen was bubbled through the suspension for a few minutes before $PdCl_2$(dppf)-DCM (37 mg, 0.453 mmol) was added. The reaction mixture was heated at 120° C. for 30 min in a microwave reactor. The mixture was directly filtered through a syringeless filter device and concentrated. The crude material was purified by silica gel chromatography using a gradient of 0-10% MeOH in DCM to provide the title compound (250 mg, 83%) as a light brown solid. $^1$H NMR (400 MHz, DMSO-$d_6$, 80° C.) δ 8.73 (s, 2H), 6.61 (br s, 2H), 6.32 (s, 1H), 5.95 (s, 1H), 4.30-4.14 (m, 1H), 3.79 (s, 2H) 3.68 (s, 8H) 3.63-3.53 (m, 1H), 3.27 (d, J=13.5 Hz, 1H), 2.12-2.00 (m, 1H), 1.89-1.60 (m, 3H), 1.55-1.43 (m, 1H), 1.31 (s, 9H); m/z (APCI+) $C_{23}H_{34}N_8O_4$ 487.3 (M+H)$^+$.

Step 3: Preparation of (3-{[2'-amino-2-(morpholin-4-yl)-4,5'-bipyrimidin-6-yl]amino}piperidin-3-yl)methanol hydrochloride

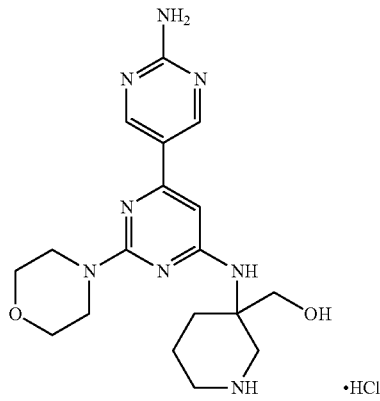 [SMILES: Nc1ncc(-c2cc(NC3(CO)CCCNC3)nc(N3CCOCC3)n2)cn1 ; Cl]

To a solution of tert-butyl 3-{[2'-amino-2-(morpholin-4-yl)-4,5'-bipyrimidin-6-yl]amino}-3-(hydroxymethyl)piperi-dine-1-carboxylate (247 mg, 0.507 mmol) in MeOH (2.4 mL) was added 4N HCl in 1,4-dioxane (2.53 mL, 10.1 mmol) at 0° C. and the reaction was stirred at room temperature for 2 h. The mixture was diluted with toluene and concentrated. The residue was concentrated from toluene a second time to give 272.5 mg (>99%) of the title compound as a yellow solid. $^1$H NMR (400 MHz, DMSO-$d_6$, 80° C.) δ 9.38 (br s, 1H), 8.72 (s, 2H), 8.63 (br s, 1H), 7.43 (br s, 1H), 6.48 (s, 1H), 3.94 (d, J=12.6 Hz, 1H), 3.85 (d, J=11.0 Hz, 1H), 3.76-3.65 (m, 9H), 3.22-3.11 (m, 1H), 3.10-2.99 (m, 1H), 2.94-2.80 (m, 1H), 2.35-2.23 (m, 1H), 1.98-1.81 (m, 1H), 1.78-1.64 (m, 2H); m/z (APCI+) for $C_{18}H_{26}N_8O_2$ 387.3 (M+H)$^+$.

Step 4: Preparation of methyl 3-{[2'-amino-2-(morpholin-4-yl)-4,5'-bipyrimidin-6-yl]amino}-3-(hydroxymethyl)piperidine-1-carboxylate

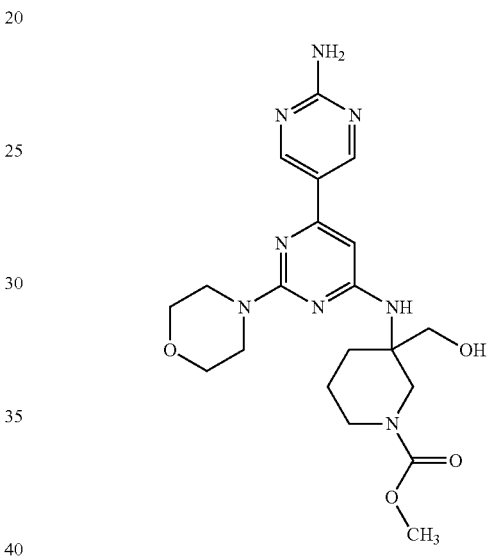

To a stirred light yellow suspension of (3-{[2'-amino-2-(morpholin-4-yl)-4,5'-bipyrimidin-6-yl]amino}piperidin-3-yl)methanol hydrochloride (66.2 mg, 0.134 mmol) in dry DCM (5 mL) was added TEA (0.11 mL, 0.801 mmol) at 0° C., followed by a solution of methyl chloroformate (13.2 mg, 0.140 mmol) in dry DCM (1 mL). The resulting mixture was stirred at 0-10° C. for 40 min. The mixture was washed with water (2 mL), extracted with 10% iPrOH/DCM (3×), dried over $Na_2SO_4$, filtered, concentrated and purified via a reversed phase HPLC (Column: XBridge C18 30×250 mm at 60° C. eluting with 0%-25% of $H_2O$ with 0.1% AcOH to $CH_3CN$ with 0.1% AcOH over 25 min) to give 42.7 mg (72%) of Example 4, the racemic title compound, as a white solid. $^1$H NMR (400 MHz, DMSO-$d_6$, 80° C.) δ 8.74 (s, 2H), 6.60 (s, 2H), 6.33 (s, 1H), 5.95 (s, 1H), 4.04 (d, J=13.3 Hz, 1H), 3.84-3.77 (m, 1H), 3.74 (s, 1H), 3.73-3.65 (m, 8H), 3.56 (d, J=13.4 Hz, 2H), 3.52 (s, 3H), 3.50-3.46 (m, 1H), 3.24-3.15 (m, 1H), 2.11-2.01 (m, 1H), 1.82-1.72 (m, 1H), 1.71-1.57 (m, 1H), 1.57-1.46 (m, 1H); m/z (APCI+) for $C_{20}H_{28}N_8O_4$ 445.3 (M+H)$^+$. The racemic material, Example 4, was further purified by chiral SFC (column: Whelk-O1 (S,S) 4.6×100 mm 5µ eluting with 30% $CO_2$ in MeOH at 120 bar; flow rate 4 mL/min) to give Example 5 (retention time 2.56 min) as a white solid: $^1$H NMR (400 MHz, DMSO-$d_6$, 80° C.) δ 8.74 (s, 2H), 6.61 (br s, 2H), 6.34 (s, 1H), 5.96 (br s, 1H), 4.48 (br s, 1H), 4.04 (d, J=13.5 Hz, 1H), 3.85-3.77

(m, 1H), 3.77-3.63 (m, 9H), 3.60-3.46 (m, 5H), 3.26-3.14 (m, 1H), 2.05 (br s, 1H), 1.83-1.72 (m, 1H), 1.64 (br s, 1H), 1.54 (br s, 1H); m/z (APCI+) for $C_{20}H_{28}N_8O_4$ 445.3 (M+H)$^+$; $[\alpha]_D^{22}$=−15.6° (c=0.1, MeOH); and Example 6 (retention time 3.19 min) as a white solid: $^1$H NMR (400 MHz, DMSO-d$_6$, 80° C.) δ 8.74 (s, 2H), 6.61 (br s, 2H), 6.34 (s, 1H), 5.96 (br s, 1H), 4.48 (t, J=5.3 Hz, 1H), 4.04 (d, J=13.3 Hz, 1H), 3.85-3.72 (m, 2H), 3.72-3.62 (m, 8H), 3.61-3.46 (m, 5H), 3.25-3.13 (m, 1H), 2.12-2.00 (m, 1H), 1.83-1.71 (m, 1H), 1.71-1.58 (m, 1H), 1.58-1.45 (m, 1H); m/z (APCI+) for $C_{20}H_{28}N_8O_4$ 445.3 (M+H)$^+$; $[\alpha]_D^{22}$= +13.2° (c=0.1, MeOH).

Examples 7, 8 and 9 (Scheme A): Preparation of tert-butyl 3-{[2'-amino-2-(morpholin-4-yl)-4,5'-bipyrimidin-6-yl]oxy}-3-(hydroxymethyl)pyrrolidine-1-carboxylate (racemate and enantiomers)

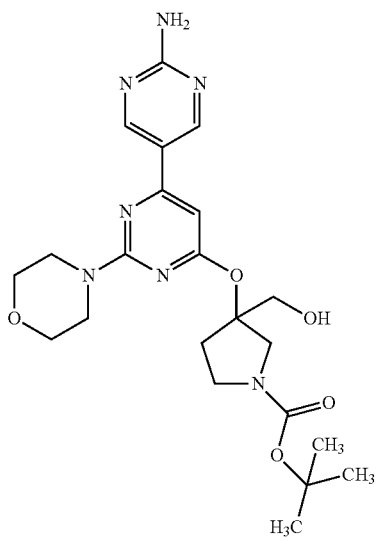 [SMILES: CC(C)(C)OC(=O)N1CCC(CO)(Oc2cc(-c3cnc(N)nc3)nc(N3CCOCC3)n2)C1]

Step 1: Preparation of tert-butyl 3-{[6-chloro-2-(morpholin-4-yl)pyrimidin-4-yl]oxy}-3-ethenylpyrrolidine-1-carboxylate

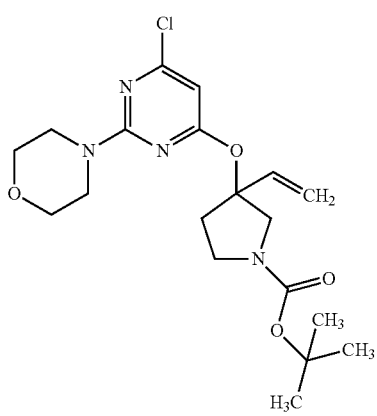 [SMILES: C=CC1(Oc2cc(Cl)nc(N3CCOCC3)n2)CCN(C(=O)OC(C)(C)C)C1]

The product of Preparation 4, tert-butyl 3-ethenyl-3-hydroxypyrrolidine-1-carboxylate (661 mg, 3.10 mmol), and 4-(4,6-dichloropyrimidin-2-yl)morpholine (725 mg, 3.10 mmol) were dissolved in THF (20 mL) under nitrogen and cooled to 0° C. Sodium hydride (60% dispersion in mineral oil, 146 mg, 3.66 mmol) was added portion-wise and the vessel was fitted with a reflux condenser under nitrogen. The reaction mixture was allowed to warm to room temperature and heated under reflux to produce an orange solution. After 23 h, the mixture was cooled to 0° C., quenched with a saturated aqueous ammonium chloride (6 mL) and allowed to warm to room temperature. Brine (15 mL) and EtOAc (15 mL) were added to the mixture and the layers were separated. The aqueous phase was extracted with EtOAc (2×15 mL) and the combined organic phases were dried over Na$_2$SO$_4$, filtered and concentrated under reduced pressure. The crude product was purified by silica gel chromatography (0-25% EtOAc/heptanes) to give the title compound (1.12 g, 88%) as a white foam. $^1$H NMR (400 MHz, DMSO-d$_6$, 80° C.) δ 6.22 (dd, J=17.6, 11.0 Hz, 1H), 6.14 (s, 1H), 5.28-5.19 (m, 2H), 3.86 (d, J=12.4 Hz, 1H), 3.71-3.61 (m, 9H), 3.42-3.35 (m, 2H), 2.31-2.21 (m, 1H), 1.41 (s, 9H); m/z (APCI+) for $C_{19}H_{27}ClN_4O_4$ 311.1 (M+H—BOC)$^+$.

Step 2: Preparation of tert-butyl 3-{[6-chloro-2-(morpholin-4-yl)pyrimidin-4-yl]oxy}-3-(hydroxymethyl)pyrrolidine-1-carboxylate

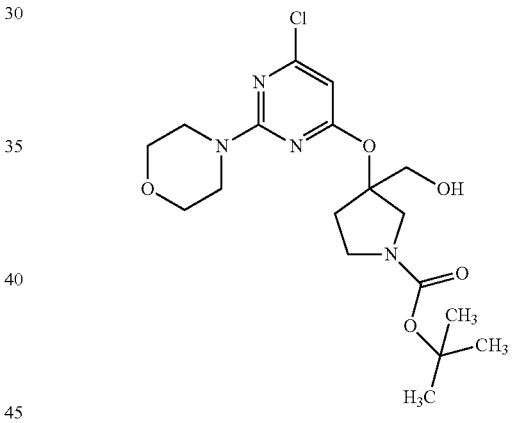

tert-Butyl 3-{[6-chloro-2-(morpholin-4-yl)pyrimidin-4-yl]oxy}-3-ethenylpyrrolidine-1-carboxylate (1.12 g, 2.73 mmol) was dissolved in water (2.5 mL), acetone (25 mL), and 2,6-lutidine (0.64 mL). N-Methyl-morpholine N-oxide (479 mg, 4.09 mmol) was added followed by OsO$_4$ (2.5 wt % in tert-butanol, 0.554 mL, 0.0545 mmol) and the mixture was stirred at room temperature for 16 h. Phenyliodonium diacetate (1.33 g, 4.09 mmol) was added in one portion and the mixture was stirred for 4.5 h whereupon the reaction was quenched with a saturated aqueous sodium thiosulfate solution (10 mL). The reaction mixture was stirred for 10 min whereupon water (20 mL) was added and the mixture was extracted with EtOAc (3×20 mL). The combined organic phases were washed with brine (30 mL), dried over Na$_2$SO$_4$, filtered and concentrated. The crude residue was dissolved in MeOH (25 mL), cooled to 0° C. and sodium borohydride (516 mg, 13.6 mmol) was added in portions. After 1 h, an aqueous solution of saturated ammonium chloride was added and the mixture was extracted with EtOAc (3×25 mL). The combined organic phases were washed with brine (2×25 mL), dried over Na$_2$SO$_4$, filtered and concentrated.

The crude product was purified by silica gel chromatography (25-100% EtOAc/heptanes) to give the title compound (1.06 g, 94%) as a white foam. ¹H NMR (400 MHz, CDCl₃) δ 6.06 (s, 1H), 4.07-3.91 (m, 2H), 3.87-3.64 (m, 10H), 3.54-3.40 (m, 2H), 2.43-2.34 (m, 1H), 2.28-2.18 (m, 1H), 1.45 (s, 9H); m/z (APCI+) for C₁₈H₂₇ClN₄O₆ 415.1 (M+H)⁺.

Step 3: Preparation of tert-butyl 3-{[2'-amino-2-(morpholin-4-yl)-4,5'-bipyrimidin-6-yl]oxy}-3-(hydroxymethyl)pyrrolidine-1-carboxylate

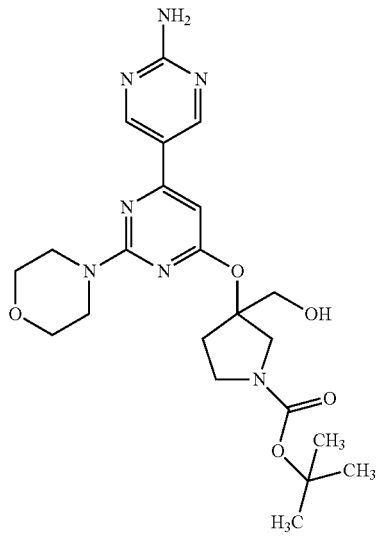 [SMILES: CC(C)(C)OC(=O)N1CCC(CO)(Oc2cc(-c3cnc(N)nc3)nc(N3CCOCC3)n2)C1]

To a solution of tert-butyl 3-{[6-chloro-2-(morpholin-4-yl)pyrimidin-4-yl]oxy}-3-(hydroxymethyl)pyrrolidine-1-carboxylate (385 mg, 0.928 mmol) in saturated aqueous sodium carbonate (0.7 mL) and 1,4-dioxane (3 mL) was added 5-(4,4,5,5-tetramethyl-1,3,2-dioxaborolan-2-yl)pyrimidin-2-amine (369 mg, 1.67 mmol) and PdCl₂(dppf)-DCM (75.8 mg, 0.928 mmol), rinsing with 1,4-dioxane (4 mL). The reaction mixture was bubbled with nitrogen and heated in a microwave reactor at 120° C. for 45 min. The mixture was diluted with brine, extracted with EtOAc (3×5 mL) and the combined organic phases were washed with brine, dried over Na₂SO₄, filtered and concentrated to give Example 7, the racemic title compound. ¹H NMR (400 MHz, 80° C., DMSO-d₆) δ 8.88 (s, 2H), 6.73 (s, 2H), 6.49 (s, 1H), 4.82-4.77 (m, 1H), 4.03-3.95 (m, 2H), 3.84-3.62 (m, 10H), 3.43-3.33 (m, 2H), 2.44-2.35 (m, 1H), 2.34-2.24 (m, 1H), 1.41 (s, 9H). The crude product was purified and separated by chiral preparative SFC (SFC/Phenomenex Lux Cellulose-1 250×21.2 mm column with 10% MeOH at 120 bar; flow rate 100 mL/min) to give 130 mg (30%) of Example 8 (retention time 1.64 min) as a white solid: ¹H NMR (400 MHz, 80° C., DMSO-d₆) δ 8.88 (s, 2H), 6.73 (s, 2H), 6.49 (s, 1H), 4.82-4.77 (m, 1H), 4.03-3.95 (m, 2H), 3.84-3.62 (m, 10H), 3.43-3.33 (m, 2H), 2.44-2.35 (m, 1H), 2.34-2.24 (m, 1H), 1.41 (s, 9H); m/z (APCI+) for C₂₂H₃₁N₇O₅ 474.1 (M+H)⁺ and 122 mg (28%) of Example 9 (retention time 1.89 min) as a white solid: ¹H NMR (400 MHz, 80° C., DMSO-d₆) δ 8.88 (s, 2H), 6.73 (s, 2H), 6.49 (s, 1H), 4.82-4.77 (m, 1H), 4.03-3.95 (m, 2H), 3.84-3.62 (m, 10H), 3.43-3.33 (m, 2H), 2.44-2.35 (m, 1H), 2.34-2.24 (m, 1H), 1.41 (s, 9H); m/z (APCI+) for C₂₂H₃₁N₇O₅ 474.1 (M+H)⁺.

Example 10 (Scheme A): Preparation of tert-butyl (3S)-3-{[2'-amino-2-(morpholin-4-yl)-4,5'-bipyrimidin-6-yl]amino}-3-(1-hydroxyethyl)pyrrolidine-1-carboxylate

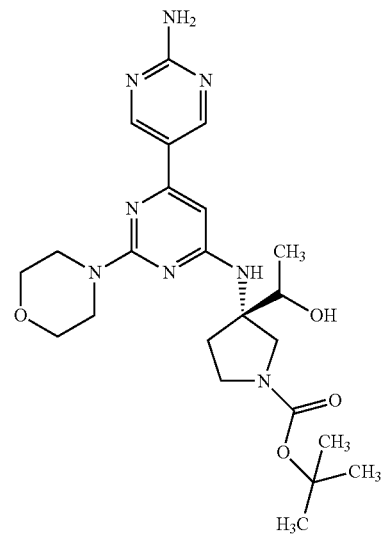 [SMILES: CC(O)[C@]1(Nc2cc(-c3cnc(N)nc3)nc(N3CCOCC3)n2)CCN(C(=O)OC(C)(C)C)C1]

Step 1: Preparation of tert-butyl (3S)-3-{[6-chloro-2-(morpholin-4-yl)pyrimidin-4-yl]amino}-3-(hydroxymethyl)pyrrolidine-1-carboxylate

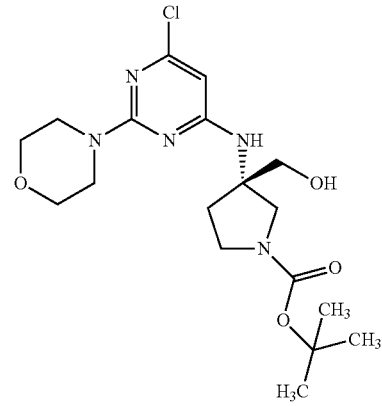 [SMILES: CC(C)(C)OC(=O)N1CC[C@](CO)(Nc2cc(Cl)nc(N3CCOCC3)n2)C1]

4-(4,6-Dichloropyrimidin-2-yl)morpholine (117 mg, 0.50 mmol), N-methylpyrrolidinone (2.50 mL), diisopropylethylamine (0.261 mL, 1.50 mmol) and tert-butyl (3S)-3-amino-3-(hydroxymethyl)pyrrolidine-1-carboxylate (108 mg, 0.50 mmol) were combined in a reaction vessel and the vessel was sealed. The reaction mixture was heated at 130° C. for 5 days. After cooling to room temperature, the reaction mixture was added dropwise to ice-cold water. The resulting suspension was filtered and the precipitate was dissolved in a mixture of dichloromethane and ethanol. This mixture was concentrated to dryness by rotary evaporation and the residue was purified by silica gel chromatography using gradient elution of (20% ethanol in EtOAc) in heptane (25-50%) to give the title compound (68 mg, 30%) as an off-white solid. ¹H NMR (400 MHz, DMSO-d₆) δ 7.28 (d, J=14.2 Hz, 1H), 5.88 (s, 1H), 5.07-4.79 (m, 1H), 3.93-3.65 (m, 2H), 3.65-3.53 (m, 9H), 3.50-3.34 (m, 1H), 2.17 (br s, 1H), 2.13-2.02 (m, 1H), 1.38 (d, J=5.3 Hz, 9H); m/z (APCI+) for $C_{18}H_{28}ClN_6O_4$ 414.1 (M+H)$^+$.

Step 2: Preparation of tert-butyl (3S)-3-{[2'-amino-2-(morpholin-4-yl)-4,5'-bipyrimidin-6-yl]amino}-3-(1-hydroxyethyl)pyrrolidine-1-carboxylate

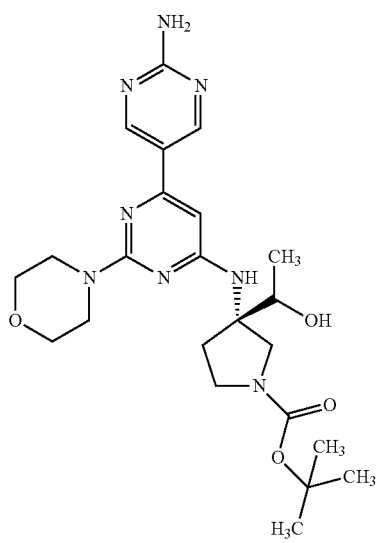 [SMILES: CC(O)[C@]1(Nc2cc(-c3cnc(N)nc3)nc(N3CCOCC3)n2)CCN(C(=O)OC(C)(C)C)C1]

tert-Butyl (3S)-3-{[6-chloro-2-(morpholin-4-yl)pyrimidin-4-yl]amino}-3-(hydroxymethyl)pyrrolidine-1-carboxylate (20.5 mg, 0.0495 mmol) was dissolved in dichloromethane (1 mL) and sodium bicarbonate (20.8 mg, 0.248 mmol) was added. The reaction mixture was cooled to 0° C. and Dess-Martin periodinane (25.7 mg, 0.0594 mmol) was added and the mixture was stirred for 2 h. An additional portion of Dess-Martin Periodinane (5.00 mg, 0.012 mmol) was added and the reaction was stirred for an additional 50 min. A saturated aqueous solution of sodium sulfite was added and the layers were separated. The aqueous phase was extracted with DCM (3×1 mL) and the combined organic phases were dried over $Na_2SO_4$, filtered and concentrated. The residue was diluted with THF (0.5 mL), cooled to −78° C. and 3 M methyl magnesium bromide in diethyl ether (32 μL, 0.096 mmol) was added in two portions (1.5 h apart) and the mixture was stirred for 40 min. A saturated aqueous solution of ammonium chloride (0.5 mL) and MeOH (0.5 mL) were added and the mixture was extracted with EtOAc (3×1 mL). The combined organic phases were dried over $Na_2SO_4$, filtered and concentrated. The residue was dissolved in 1,4-dioxane (0.6 mL) and 5-(4,4,5,5-tetramethyl-1,3,2-dioxaborlan-2-yl)-pyrimidin-2-ylamine (15.2 mg, 0.0687 mmol), Pd(dppf)$Cl_2$.DCM (3.21 mg, 0.00393 mmol), and 1M aqueous sodium carbonate (13.0 mg, 0.123 mmol) were added. The reaction mixture was bubbled with nitrogen and heated in a microwave reactor at 120° C. for 30 min. The mixture was diluted with a saturated aqueous sodium bicarbonate solution and extracted with EtOAc (3×1 mL). The combined organic phases were dried over magnesium sulfate, filtered and concentrated. The crude product was purified by preparatory HPLC (Waters Xbridge C18, 30×250 mm, 5 μm particle size; Column temperature of 60° C., Solvent A: Water with 0.1% Acetic acid, Solvent B: Acetonitrile with 0.1% Acetic acid, Gradient: 0% B for 5 min, 0-20% B in 5-25 min, 95% B 25-30 min; flow rate 8 mL/min) to give the title compound (7.1 mg, 30%) as white solid (a 7:3 mixture of diastereomers). $^1$H NMR (400 MHz, 80° C., DMSO-$d_6$) δ 8.73 (br s, 2H), 6.78-6.65 (m, 3H), 6.32-6.23 (m, 1H), 5.16-4.86 (m, 1H), 4.46-4.22 (m, 1H), 3.73-3.48 (m, 10H), 3.41-3.27 (m, 2H), 2.24-1.97 (m, 2H), 1.42-1.33 (m, 9H), 1.10-1.00 (m, 3H); m/z (APCI+) for $C_{23}H_{34}N_8O_4$ 487.3 (M+H)$^+$.

Example 11 (Scheme B): Preparation of methyl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate

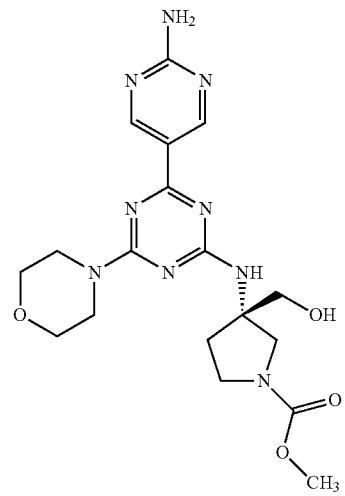 [SMILES: COC(=O)N1CC[C@](CO)(Nc2nc(-c3cnc(N)nc3)nc(N3CCOCC3)n2)C1]

Step 1: Preparation of 2,4-dichloro-6-(morpholin-4-yl)-1,3,5-triazine

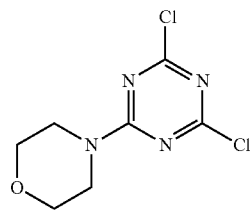 [SMILES: Clc1nc(Cl)nc(N2CCOCC2)n1]

To a white suspension of 2,4,6-trichloropyrimidine (6000 mg, 32.54 mmol) in DCM (60 mL) was added 1M aqueous NaHCO$_3$ (65.1 mL, 65.1 mmol) at 0° C. Morpholine (2830 mg, 32.5 mmol) in DCM (20 mL) was added dropwise at 0° C. and the mixture was stirred for 1 h. The reaction mixture was extracted with DCM (20 mL×3), the combined organic layers were washed with brine (50 mL), dried over Na$_2$SO$_4$, filtered and concentrated. The residue was purified by silica gel chromatography eluting with 6:1 petroleum ether/EtOAc to give the title compound (4500 mg, 58%) as a white solid. $^1$H NMR (400 MHz, CDCl$_3$) δ 3.91-3.85 (m, 4H), 3.77-3.73 (m, 4H).

Step 2: Preparation of tert-butyl (3S)-3-{[4-chloro-6-(morpholin-4-yl)-1,3,5-triazin-2-yl]amino}-3-(hydroxymethyl)pyrrolidine-1-carboxylate

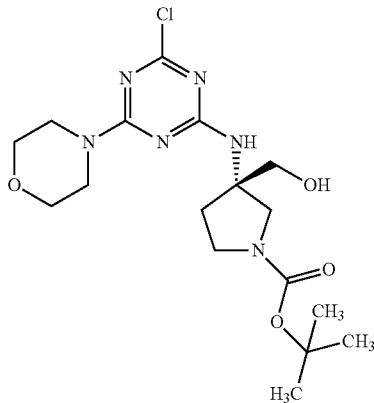

A solution of 2,4-dichloro-6-(morpholin-4-yl)-1,3,5-triazine (2500 mg, 10.64 mmol), NaHCO$_3$ (2680 mg, 31.9 mmol) and tert-butyl (3S)-3-amino-3-(hydroxymethyl)pyrrolidine-1-carboxylate (2760 mg, 12.8 mmol) in MeCN (20 mL) was stirred at 10° C. for 42 h. The reaction mixture was diluted with water (20 mL) and extracted with DCM (50 mL×4). The combined organic layers were concentrated and the residue was purified by silica gel chromatography eluting with 1:1 petroleum ether/EtOAc to give the title compound (2500 mg, 57%) as a white solid. $^1$H NMR (400 MHz, CDCl$_3$) δ 5.61-5.54 (m, 1H), 4.15-4.05 (comp, 11H), 3.58-3.46 (m, 4H), 2.20-2.17 (m, 2H), 1.46 (s, 9H).

Step 3: Preparation of tert-butyl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate

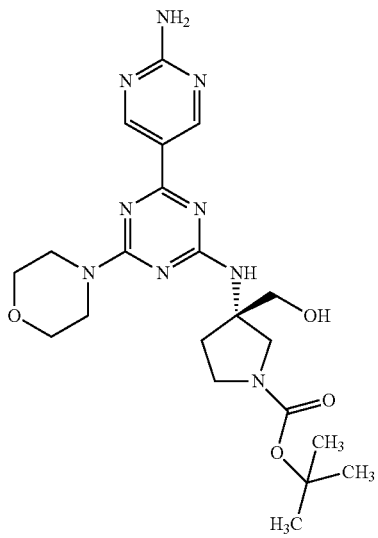 [SMILES: CC(C)(C)OC(=O)N1CC[C@](CO)(Nc2nc(-c3cnc(N)nc3)nc(N3CCOCC3)n2)C1]

To a mixture of tert-butyl (3S)-3-{[4-chloro-6-(morpholin-4-yl)-1,3,5-triazin-2-yl]amino}-3-(hydroxymethyl)pyrrolidine-1-carboxylate (300 mg, 0.723 mmol) and 5-(4,4,5,5-tetramethyl-1,3,2-dioxaborolan-2-yl)pyrimidin-2-amine (208 mg, 0.940 mmol) and Na$_2$CO$_3$ (230 mg, 2.17 mmol) in 1,4-dioxane (6 mL) and water (1 mL) was added Pd(dppf)Cl$_2$-DCM (52.9 mg, 0.0723 mmol) under nitrogen. The mixture was sealed and stirred at 120° C. in a microwave reactor for 45 min. The mixture was concentrated and the residue was purified by silica gel chromatography eluting with 20:1 EtOAc/MeOH to give the title compound (207 mg, 61%) as an off-white solid. $^1$H NMR (400 MHz, DMSO-d$_6$) δ 9.00 (s, 2H), 7.35-7.24 (m, 3H), 5.01-4.96 (m, 1H), 3.78-3.65 (m, 12H), 3.60-3.42 (m, 2H), 2.24-2.07 (m, 2H), 1.37 (s, 9H); m/z (ESI+) for C$_{21}$H$_{31}$N$_9$O$_4$ 474.1 (M+H)$^+$.

Step 4: Preparation of [(3S)-3-{[4-(2-aminopyrimidin-5-yl)-6-(morpholin-4-yl)-1,3,5-triazin-2-yl]amino}pyrrolidin-3-yl]methanol hydrochloride

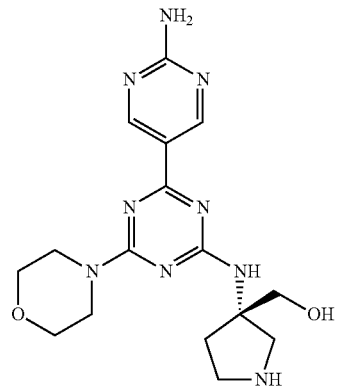 [SMILES: Nc1ncc(-c2nc(N[C@@]3(CO)CCNC3)nc(N3CCOCC3)n2)cn1]

To a stirred yellow solution of tert-butyl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate (557 mg, 1.18 mmol) in DCM (15 mL) was added HCl (g)/EtOAc (30 mL, 6N) at 0° C. and the solution was stirred at 15° C. for 3 h. The reaction mixture was concentrated and lyophilized to give the title compound (550 mg, >99%) as a yellow solid. This material was used in the next step without further purification. m/z (ESI+) for C$_{16}$H$_{23}$N$_9$O$_2$ 374.0 (M+H)$^+$.

Step 5: Preparation of methyl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate

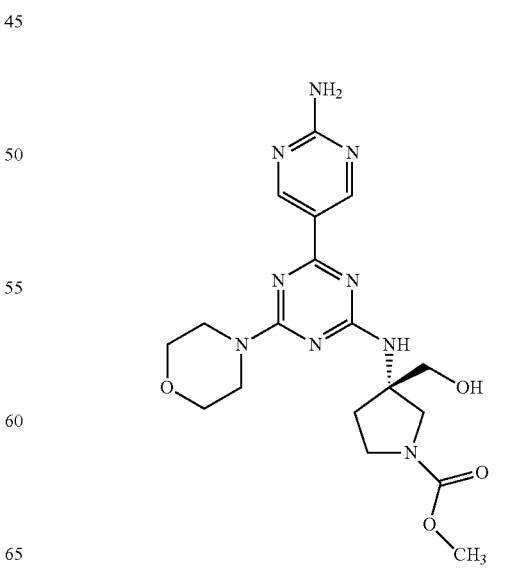

To a colorless solution of [(3S)-3-{[4-(2-aminopyrimidin-5-yl)-6-(morpholin-4-yl)-1,3,5-triazin-2-yl]amino}pyrrolidin-3-yl]methanol hydrochloride (60 mg, 0.15 mmol) in DCM (3 mL) was added TEA (71.8 mg, 0.709 mmol) at 15° C. The mixture was cooled to 0° C. and methyl chloroformate (13.4 mg, 0.142 mmol) was added. The mixture was allowed to warm to room temperature and stirring was continued for 20 min. The mixture was concentrated to give a light yellow solid, which was purified by preparative HPLC (Column Luna C18 150×25 5μ eluting with 10-30% B to A; B: acetonitrile, A: 0.225% formic acid in water; flow rate 35 mL/min) to give the title compound (18 mg, 29%) as a white solid. $^1$H NMR (400 MHz, DMSO-$d_6$) δ 8.99 (s, 2H), 7.36-7.23 (m, 3H), 4.98 (br s, 1H), 3.75-3.56 (m, 12H), 3.53 (s, 3H), 3.49-3.41 (m, 2H), 2.32-2.31 (m, 1H), 2.13-2.12 (m, 1H); m/z (ESI+) for $C_{18}H_{26}N_9O_4$ 432.2 (M+H)$^+$.

Preparation 1: Preparation of 4-(4,6-dichloro-5-fluoropyrimidin-2-yl)morpholine

Step 1: Preparation of 5-fluoro-2-(morpholin-4-yl)pyrimidine-4,6-diol

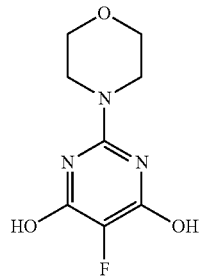

Sodium metal (9.68 g, 421 mmol) was cut in small pieces and added to dry EtOH (300 mL) in portions. After all the sodium was dissolved, morpholine-4-carboxamidine sulfate (30 g, 168 mmol) and diethyl fluoromalonate (30 g, 168 mmol) were added to the mixture at 10° C. The resulting white suspension was stirred at 20° C. for 10 min and then heated under reflux for 12 h. The resulting purple suspension was concentrated under reduced pressure and water (150 mL) was added. The solution was treated with 6N HCl (60 mL) to obtain pH~4 at 10° C. The resulting yellow precipitate was collected by filtration, washed with water (40 mL×2) and the yellow filter cake was dried under an infrared lamp for 12 h to give 34 g (94%) of the title compound as a yellow solid. $^1$H NMR (400 MHz, DMSO-$d_6$) δ 3.65-3.57 (m, 4H) 3.53-3.46 (m, 4H); m/z (APCI−) for $C_8H_{10}FN_3O_3$ 214.1 (M−H)$^-$.

Step 2: Preparation of 4-(4,6-dichloro-5-fluoropyrimidin-2-yl)morpholine

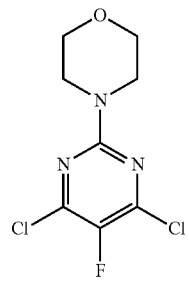 [SMILES: Fc1c(Cl)nc(N2CCOCC2)nc1Cl]

A suspension of 5-fluoro-2-(morpholin-4-yl)pyrimidine-4,6-diol (34 g, 158 mmol) in phosphorous oxychloride (400 mL) was heated under reflux for 6 h. The resulting black solution was cooled to 20° C. and concentrated under reduced pressure. The residue was treated with 4N aqueous NaOH (100 mL) to obtain pH ~8. The mixture was extracted with DCM (250 mL×3), the combined organic layers were washed with brine (60 mL), dried over $Na_2SO_4$ and concentrated to give a yellow solid. The crude product was purified by silica gel column chromatography eluting with 10:1 petroleum ether/EtOAc to obtain the title compound (23 g, 58%) as a yellow solid. $^1$H NMR (400 MHz, DMSO-$d_6$) δ 3.71-3.60 (m, 8H).

Preparation 2: Preparation of (3S)-4-(4,6-dichloropyrimidin-2-yl)-3-methylmorpholine Step 1: Preparation of (3S)-4-(4,6-dimethoxypyrimidin-2-yl)-3-methylmorpholine

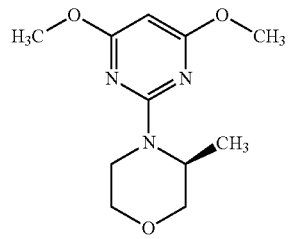

A solution of (S)-3-methylmorpholine (4.86 g, 48.0 mmol), 2-chloro-4,6-dimethoxypyrimidine (6.98 g, 40 mmol) and DIPEA (8.36 mL, 48.0 mmol) in DMSO (40 mL) was heated at 100° C. in a sealed flask for 22 h, and then allowed to cool to room temperature. The reaction mixture was placed in an ice bath, and water (120 mL) was added dropwise. The mixture was decanted and the gummy precipitate was dissolved in EtOAc. The EtOAc solution was washed with brine, dried with MgSO$_4$, filtered and concentrated by rotary evaporation to give the title compound (8.58 g, 90%). $^1$H NMR (400 MHz, CDCl$_3$) δ 5.40 (s, 1H), 4.69 (qd, J=6.8, 3.1 Hz, 1H), 4.33 (dd, J=13.7, 2.9 Hz, 1H), 4.01-3.93 (m, 1H), 3.86 (s, 6H), 3.78-3.73 (m, 1H), 3.73-3.66 (m, 1H), 3.54 (ddd, J=12.2, 11.4, 3.1 Hz, 1H), 3.25 (ddd, J=13.5, 12.4, 3.8 Hz, 1H), 1.29 (d, J=6.8 Hz, 3H); m/z (APCI+) for $C_{11}H_{17}N_3O_3$ 240.0 (M+H)$^+$.

Step 2: Preparation of 2-[(3S)-3-methylmorpholin-4-yl]pyrimidine-4,6-diol

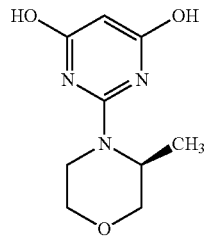

(3S)-4-(4,6-Dimethoxypyrimidin-2-yl)-3-methylmorpholine (6.3 g, 26.3 mmol) was dissolved in MeCN (88 mL).

Argon was bubbled into the solution and sodium iodide (11.8 g, 79.0 mmol) and TMS-Cl (10.3 mL, 79.0 mmol) were added. The reaction was heated under reflux for 2 h, and allowed to cool to room temperature. Water (50 mL) and sodium bisulfite (2.74 g, 26.3 mmol) were added. MeCN was removed by rotary evaporation and the resulting slurry was filtered. The precipitate was suspended in ethanol and concentrated to dryness by rotary evaporation to give the title compound (3.81 g, 68%). $^1$H NMR (400 MHz, DMSO-$d_6$) δ 10.61 (br s, 2H), 4.80 (br s, 1H), 4.40 (d, J=5.9 Hz, 1H), 3.98 (d, J=12.7 Hz, 1H), 3.85 (dd, J=11.3, 3.5 Hz, 1H), 3.68-3.62 (m, 1H), 3.56-3.50 (m, 1H), 3.38 (td, J=11.8, 3.0 Hz, 1H), 3.16-3.04 (m, 1H), 1.16 (d, J=6.7 Hz, 3H).

Step 3: Preparation of (3S)-4-(4,6-dichloropyrimidin-2-yl)-3-methylmorpholine

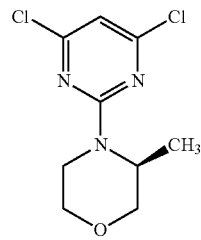

2-[(3S)-3-Methylmorpholin-4-yl]pyrimidine-4,6-diol (4.06 g, 19.2 mmol) was suspended in MeCN (38.4 mL) and phosphorous oxychloride (14.3 mL, 154 mmol) was added. The reaction mixture was heated in a sealed vial for 2 h and then concentrated by rotary evaporation. A 1:1 mixture of MeCN and water (10 mL) was added dropwise with stirring keeping the temperature below 40° C. Additional water (20 mL) was added and the MeCN was removed by rotary evaporation. The resulting slurry was cooled to 0° C. and solids were collected by filtration. The resultant solid was dissolved in dichloromethane, dried with Na$_2$SO$_4$, filtered and concentrated by rotary evaporation to give the title compound (4.38 g, 92%). $^1$H NMR (400 MHz, CDCl$_3$) δ 6.56 (s, 1H), 4.68 (qd, J=6.8, 3.1 Hz, 1H), 4.33 (dd, J=13.7, 2.9 Hz, 1H), 3.97 (dd, J=11.5, 3.7 Hz, 1H), 3.79-3.73 (m, 1H), 3.69-3.64 (m, 1H), 3.51 (td, J=11.9, 3.0 Hz, 1H), 3.30 (ddd, J=13.6, 12.4, 3.8 Hz, 1H), 1.32 (d, J=6.5 Hz, 3H); m/z (APCI+) for C$_9$H$_{11}$Cl$_2$N$_3$O 247.9 (M+H)$^+$.

Preparation 3: Preparation of tert-butyl (3S)-3-amino-3-(hydroxymethyl)pyrrolidine-1-carboxylate Step 1: Preparation of tert-butyl (3S)-3-amino-3-(hydroxymethyl)pyrrolidine-1-carboxylate hemi-(+)-O,O'-di-p-toluoyl-D-tartrate

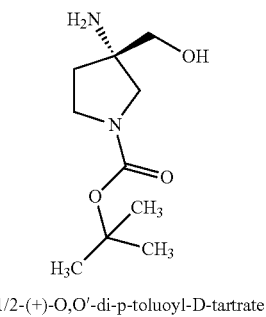

1/2-(+)-O,O'-di-p-toluoyl-D-tartrate

A mixture of tert-butyl-3-amino-3-(hydroxymethyl)pyrrolidine-1-carboxylate (1 g, 4.62 mmol) and (+)-O,O'-di-p-toluoyl-D-tartaric acid (893 mg, 2.31 mmol) was suspended in isopropanol (5 mL) and the mixture was sonicated until mostly dissolved. The resultant suspension was heated at 65° C. for a few min and sonicated again resulting in a homogeneous mixture. The pale yellow solution was heated at 65° C. After ~5 min, the mixture became a white suspension, and stirring was continued at 65-70° C. for 18 h. The suspension was allowed to cool to room temperature over 1 h. The suspension was filtered, the solids were rinsed with a small volume of isopropanol and dried in a vacuum oven at 50° C. for 1 h to give the title compound (773 mg, 41%) as a white solid. $^1$H NMR (400 MHz, D$_2$O) δ 8.05 (d, J=7.8 Hz, 2H), 7.43 (d, J=8.1 Hz, 2H), 5.71 (s, 1H), 3.78 (s, 2H), 3.64-3.52 (m, 4H), 2.46 (s, 3H), 2.28-2.13 (m, 2H), 1.49 (s, 9H).

Step 2: Preparation of tert-butyl (3S)-3-amino-3-(hydroxymethyl)pyrrolidine-1-carboxylate

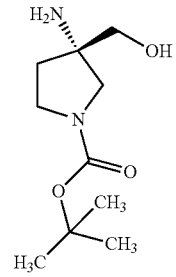

tert-Butyl (3S)-3-amino-3-(hydroxymethyl)pyrrolidine-1-carboxylate hemi-(+)-O,O'-di-p-toluoyl-D-tartrate (1 g, 2.44 mmol) was suspended in water (5 mL) and EtOAc (5 mL). The mixture was cooled in an ice bath and 6 N HCl (0.41 mL, 2.44 mmol) was added dropwise. The resulting biphasic mixture was stirred at 0° C. for 1 h. The layers were separated and the aqueous layer was washed with EtOAc (1×). The aqueous layer was cooled to 0° C., treated with 3 M aqueous NaOH (0.814 mL, 2.44 mmol) and stirred at 0° C. for 1 h. The mixture was lyophilized, the resulting solids were suspended in EtOH and the mixture was stirred at room temperature for 4 h. The mixture was filtered and the solids rinsed with EtOH. The filtrate was concentrated under reduced pressure to give the title compound (514 mg, 97%) as a white solid. $^1$H NMR (400 MHz, 80° C., DMSO-$d_6$) δ 4.48 (br s, 1H), 3.45-3.25 (m, 4H), 3.21 (d, J=10.8 Hz, 1H), 2.95 (d, J=10.8 Hz, 1H), 1.81 (td, J=8.3, 12.3 Hz, 1H), 1.58-1.45 (m, 3H), 1.41 (s, 9H).

Preparation 4: Preparation of tert-butyl 3-ethenyl-3-hydroxypyrrolidine-1-carboxylate

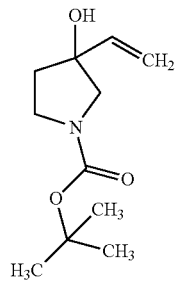

1-N-Boc-pyrrolidinone (1.00 g, 5.40 mmol) was dissolved in THF (20 mL) under nitrogen. The reaction mixture was cooled to −78° C., 1 M vinylmagnesium bromide in THF (5.94 mL, 5.94 mmol) was added via a syringe and the mixture was stirred for 1 h. A saturated aqueous solution of ammonium chloride (5 mL) was added and the mixture was allowed to warm to room temperature. Water (15 mL) was added, the mixture extracted with EtOAc (3×15 mL), the combined organic phases were dried over Na$_2$SO$_4$, filtered and concentrated. The crude product was purified by silica gel chromatography (0-40% EtOAc/heptanes) to give the title compound (307 mg, 27%) as a white solid. $^1$H NMR (400 MHz, 80° C., DMSO-$d_6$) δ 5.99 (dd, J=17.3, 10.7 Hz, 1H), 5.32 (dd, J=17.3, 1.7 Hz, 1H), 5.08 (dd, J=10.7, 1.7 Hz, 1H), 4.78 (s, 1H), 3.46-3.31 (m, 2H), 3.25-3.18 (m, 2H), 1.94-1.84 (m, 1H), 1.81-1.74 (m, 1H), 1.41 (s, 9H); m/z (APCI+) for $C_{11}H_{19}NO_3$ 114.2 (M+H-Boc)$^+$.

Preparation 5: Preparation of tert-butyl 3-amino-3-(hydroxymethyl)piperidine-1-carboxylate

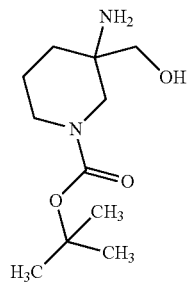 [SMILES: CC(C)(C)OC(=O)N1CCCC(N)(CO)C1]

A suspension of 3-amino-1-(tert-butoxycarbonyl)piperidine-3-carboxylic acid (4 g, 16.37 mmol) in dry THF (40 mL) was cooled to −10° C. in an ice/MeOH bath and treated with 1M BH$_3$.THF solution (50 mL, 50 mmol) via an addition funnel over 30 min. The mixture was allowed to slowly warm to room temperature over 24 h. The suspension was cooled in an ice bath and treated with MeOH (10 mL) in small portions. The mixture was stirred at 0° C. for 2 h, the ice bath was removed and the mixture was stirred at room temperature for 22 h. The mixture was treated with diethylamine (34 mL) and heated at 50° C. for 3 h. The resulting suspension was concentrated and the residue was taken up in a few mL of MeOH, dropped into 3:1 mixture of brine/1N NaOH (100 mL) and extracted with 15% isopropanol in DCM (5×). The organics were dried over MgSO$_4$ and concentrated. The residue was concentrated twice from toluene to give a syrup (2.5 g, 66%, ~80% purity) that was used in the next step without further purification. $^1$H NMR (400 MHz, 80° C., DMSO-$d_6$) δ 4.21 (br s, 1H), 3.45-3.34 (m, 1H), 3.20 (s, 2H), 3.18-3.07 (m, 2H), 2.70-2.54 (m, 1H), 1.68-1.48 (m, 2H), 1.46-1.33 (m, 10H), 1.32-1.22 (m, 1H).

The following examples were made with non-critical changes or substitutions to the exemplified procedures that would be understood by one skilled in the art.

TABLE 1

| Example Number | Structure and Compound Name | LRMS m/z [M + H]$^+$ | $^1$H NMR |
|---|---|---|---|
| 1 | [(3S)-3{[2'-amino-5-fluoro-2-(morpholin-4-yl)-4,5'-bipyrimidin-6-yl]amino}-3-(hydroxymethyl)pyrrolidin-1-yl](1-fluorocyclopropyl)methanone | 432.2 | $^1$H NMNR (400 MHz, 80° C. DMSO-$d_6$) δ 8.78 (s, 2H), 6.74 (s, 2H), 6.60 (s, 1H), 4.78 (t, J = 5.8 Hz, 1H), 3.87-3.75 (m, 4H), 3.71-3.57 (m, 10H), 2.27-2.16 (m, 1H), 1.28-1.11 (m, 4H). |
| 2 | 2,2-difluoroethyl (3S)-3-{[2'-amino-5-fluoro-2-(morpholin-4-yl)-4,5'-bipyrimidin-6-yl]amino}-3-(hydroxymethyl)pyrrolidine-1-carboxylate | 499.0 | $^1$H NMR (400 MHz, 80° C., DMSO-$d_6$) δ 8.77 (s, 2H), 6.74 (s, 2H), 6.58 (s, 1H), 6.17 (tt, J = 54.8, 2.9 Hz, 1H), 4.77 (t, J = 5.7 Hz, 1H), 4.27 (td, J = 15.1, 3.1 Hz, 2H), 3.91 (d, J = 11.6 Hz, 1H), 3.81-3.72 (m, 2H), 3.70-3.64 (m, 4H), 3.64-3.60 (m, 5H), 3.55-3.38 (m, 2H), 2.47-2.38 (m, 1H), 2.20 (dt, J = 13.5, 7.0 Hz, 1H). |

TABLE 1-continued

| Example Number | Structure and Compound Name | LRMS m/z [M + H]+ | 1H NMR |
|---|---|---|---|
| 3 | 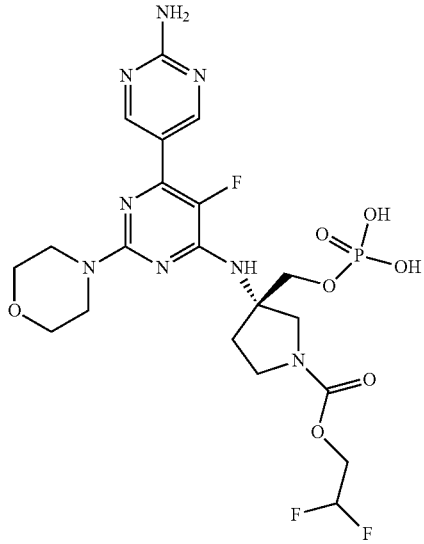 [SMILES: Nc1ncc(-c2nc(N3CCOCC3)nc(N[C@@]3(COP(=O)(O)O)CCN(C(=O)OCC(F)F)C3)c2F)cn1]<br>2,2-difluoroethyl (3S)-3-{[2'-amino-5-fluoro-2-(morpholin)-4-yl)-4,5'-bipyrimidin-6-yl]amino}-3-[(phosphonooxy)methyl] pyrrolidine-1-carboxylate | 578.8 | 1H NMR (400 MHz, 80° C., CD3OD) δ 8.69 (s, 2H), 6 94-6 88 (m, 1H), 6.73 (s, 2H), 6.24-5.95 (m, 1H), 4.24-4.11 (m, 4H), 3.87-3.85 (m, 1H), 3.60-3.49 (m, 6H), 3.44-3.30 (m, 3H), 2.19-2.08 (m, 1H). |
| 4 | 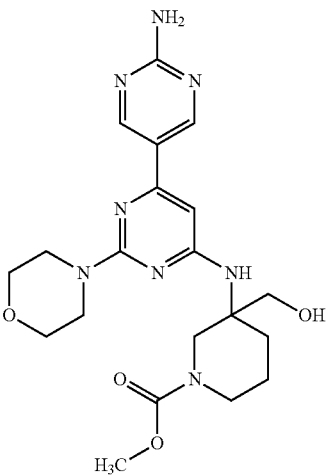 [SMILES: COC(=O)N1CCCC(CO)(Nc2cc(-c3cnc(N)nc3)nc(N3CCOCC3)n2)C1]<br>methyl 3-{[2'-amino-2-{morpholin-4-yl)-4,5'-bipyrimidin-6-yl]amino}-3-(hydroxymethyl)piperidine-1-carboxylate | 445.3 | 1H NMR (400 MHz, DMSO-d6, 80° C.) δ 8.74 (s, 2H), 6.60 (s, 2H), 6.33 (s, 1H), 5.95 (s, 1H), 4.04 (d, J = 13.3 Hz, 1H), 3.84-3.77 (m, 1H), 3.74 (s, 1H), 3.73-3.65 (m, 8H), 3.56 (d, J = 13.4 Hz, 2H), 3.52 (s, 3H), 3.50-3.46 (m, 1H), 3.24-3.15 (m, 1H), 2.11-2.01 (m, 1H), 1.82-1.72 (m, 1H), 1.71-1.57 (m, 1H), 1.57-1.46 (m, 1H). |

TABLE 1-continued

| Example Number | Structure and Compound Name | LRMS m/z [M + H]+ | 1H NMR |
|---|---|---|---|
| 5 | 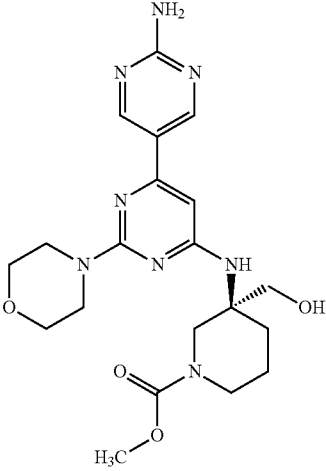 [SMILES: COC(=O)N1CCC[C@](CO)(Nc2cc(-c3cnc(N)nc3)nc(N3CCOCC3)n2)C1]<br>methyl (3S)-3{[2'-amino-2-(morpholin-4-yl)-4,5'-bipyrimidin-6-yl]amino}-3-(hydroxymethyl)piperidine-1-carboxylate | 445.3 | 1H NMR (400 MHz, DMSO-d6, 80° C.) δ 8.74 (s, 2H), 6.61 (br s, 2H), 6.34 (s, 1H), 5.96 (br s, 1H), 4.48 (br s, 1H), 4.04 (d, J = 13.5 Hz, 1H), 3.85-3.77 (m, 1H), 3.77-3.63 (m, 9H), 3.60-3.46 (m, 5H), 3.26-3.14 (m, 1H), 2.05 (br s, 1H), 1.83-1.72 (m, 1H), 1.64 (br s, 1H), 1.54 (br s, 1H). |
| 6 | 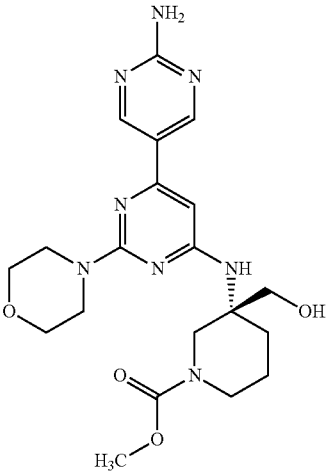 [SMILES: COC(=O)N1CCC[C@@](CO)(Nc2cc(-c3cnc(N)nc3)nc(N3CCOCC3)n2)C1]<br>methyl (3R)-3{[2'-amino-2-(morpholin-4-yl)-4,5'-bipyrimidin-6-yl]amino}-3-(hydroxymethyl)piperidine-1-carboxylate | 445.3 | 1H NMR (400 MHz, DMSO-d6, 80° C.) δ 8.74 (s, 2H), 6.61 (br s, 2H), 6.34 (s, 1H), 5.96 (br s, 1H), 4.48 (t, J = 5.3 Hz, 1H), 4.04 (d, J = 13.3 Hz, 1H), 3.85-3.72 (m, 2H), 3.72-3.62 (m, 8H), 3.61-3.46 (m, 5H), 3.25-3.13 (m, 1H), 2.12-2.00 (m, 1H), 1.83-1.71 (m, 1H), 1.71-1.58 (m, 1H), 1.58-1.45 (m, 1H). |

TABLE 1-continued
| Example Number | Structure and Compound Name | LRMS m/z [M + H]+ | 1H NMR |
|---|---|---|---|
| 7 | 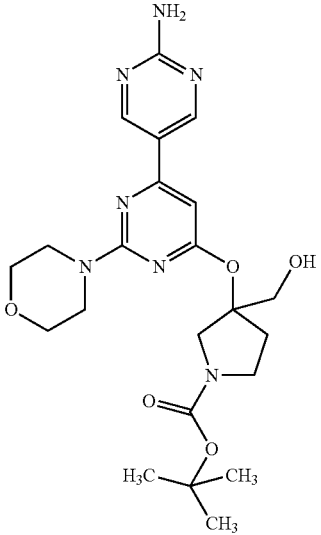 [SMILES: CC(C)(C)OC(=O)N1CCC(CO)(Oc2cc(-c3cnc(N)nc3)nc(N3CCOCC3)n2)C1]<br>tert-butyl 3-{[2'-amino-2-(morpholin-4-yl)-4,5'-bipyrimidin-6-yl]oxy}-3-(hydroxymethyl)pyrrolidine-1-carboxylate | 474.1 | 1H NMR (400 MHz, 80° C., DMSO-d6) δ 8.88 (s, 2H), 6.73 (s, 2H), 6.49 (s, 1H), 4.82-4.77 (m, 1H), 4.03-3.95 (m, 2H), 3.84-3.62 (m, 10H), 3.43-3.33 (m, 2H), 2.44-2.35 (m, 1H), 2.34-2.24 (m, 1H), 1.41 (s, 9H). |
| 8* | 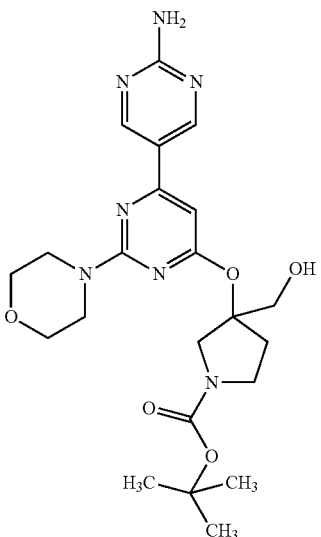<br>tert-butyl 3-{[2'-amino-2-(morpholin-4-yl)-4,5'-bipyrimidin-6-yl]oxy}-3-(hydroxymethyl)pyrrolidine-1-carboxylate | 474.1 | 1H NMR (400 MHz, 80° C., DMSO-d6) δ 8.88 (s, 2H), 6.73 (s, 2H), 6.49 (s, 1H), 4.82-4.77 (m, 1H), 4.03-3.95 (m, 2H), 3.84-3.62 (m, 10H), 3.43-3.33 (m, 2H), 2.44-2.35 (m, 1H), 2.34-2.24 (m, 1H), 1.41 (s, 9H). |

TABLE 1-continued

| Example Number | Structure and Compound Name | LRMS m/z [M + H]+ | 1H NMR |
|---|---|---|---|
| 9* | 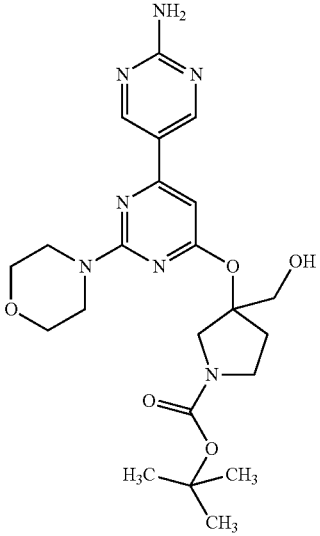 [SMILES: CC(C)(C)OC(=O)N1CCC(CO)(Oc2cc(-c3cnc(N)nc3)nc(N3CCOCC3)n2)C1]<br>tert-butyl 3-{[2'-amino-2-(morpholin-4-yl)-4,5'-bipyrimidin-6-yl]oxy}-3-(hydroxymethyl)pyrrolidine-1-carboxylate | 474.1 | 1H NMR (400 MHz, 80° C., DMSO-d6) δ 8.88 (s, 2H), 6.73 (s, 2H), 6.49 (s, 1H), 4.82-4.77 (m, 1H), 4.03-3.95 (m, 2H), 3.84-3.62 (m, 10H), 3.43-3.33 (m, 2H), 2.44-2.35 (m, 1H), 2.34-2.24 (m, 1H), 1.41 (s, 9H). |
| 10 | 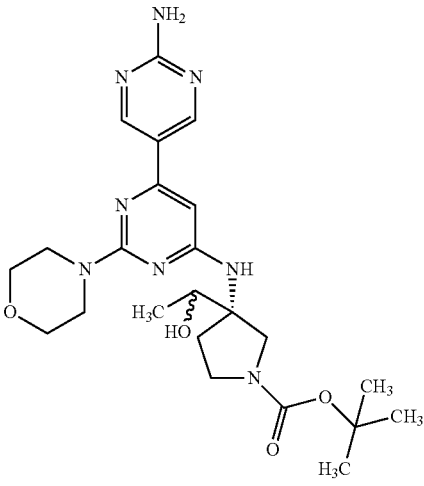 [SMILES: CC(O)[C@]1(Nc2cc(-c3cnc(N)nc3)nc(N3CCOCC3)n2)CCN(C(=O)OC(C)(C)C)C1]<br>tert-butyl (3S)-3-{[2'-amino-2-(morpholin-4-yl)-4,5'-bipyrimidin-6-yl]amino}-3-(1-hydroxyethyl)pyrrolidine-1-carboxylate | 487.3 | 1H NMR (400 MHz, 80° C., DMSO-d6; 7:3 mixture of diastereomers) δ 8.73 (br s, 2H), 6.78-6.65 (m, 3H), 6.32-6.23 (m, 1H), 5.16-4.86 (m, 1H), 4.46-4.22 (m, 1H), 3.73-3.48 (m, 10H), 3.41-3.27 (m, 2H), 2.24-1.97 (m, 2H), 1.42-1.33 (m, 9H), 1.10-1.00 (m, 3H). |

TABLE 1-continued
| Example Number | Structure and Compound Name | LRMS m/z [M + H]+ | 1H NMR |
|---|---|---|---|
| 11 | 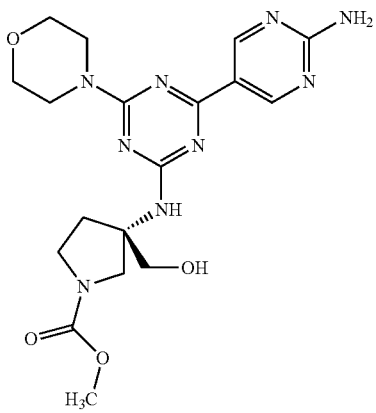 [SMILES: COC(=O)N1CC[C@](CO)(Nc2nc(-c3cnc(N)nc3)nc(N3CCOCC3)n2)C1]<br>methyl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate | 432.2 | 1H NMR (400 MHz, DMSO-d6) δ 8.99 (s, 2H), 7.36-7.23 (m, 3H), 4.98 (br s, 1H), 3.75-3.56 (m, 12H), 3.53 (s, 3H), 3.49-3.41 (m, 2H), 2.32-2.31 (m, 1H), 2.13-2.12 (m, 1H). |
| 12 | 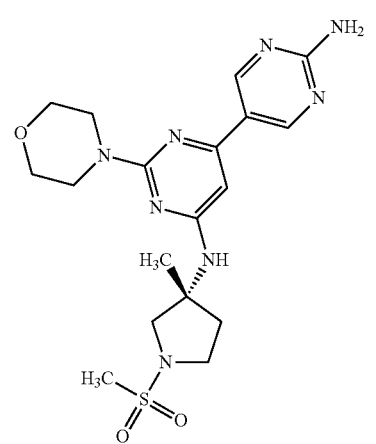 [SMILES: C[C@@]1(Nc2cc(-c3cnc(N)nc3)nc(N3CCOCC3)n2)CCN(S(C)(=O)=O)C1]<br>N-6~-[(3R)-3-methyl-1-(methylsulfonyl)pyrrolidin-3-yl]-2-(morpholin-4-yl)-4,5'-bipyrimidine-2',6-diamine | 435.0 | 1H NMR (400 MHz, CDCl3) δ 8.84 (s, 2H), 6.00 (s, 1H), 5.30 (s, 2H), 4.67 (s, 1H), 3.98 (d, J = 10.4 Hz, 1H), 3.81-3.79 (m, 8H), 3.52-3.49 (m, 2H), 3.37 (d, J = 10.4 Hz, 1H), 2.81 (s, 3H), 2.52-2.49 (m, 1H), 2.04-2.01 (m, 1H), 1.64 (s, 3H). |

TABLE 1-continued

| Example Number | Structure and Compound Name | LRMS m/z [M + H]+ | 1H NMR |
|---|---|---|---|
| 13 | 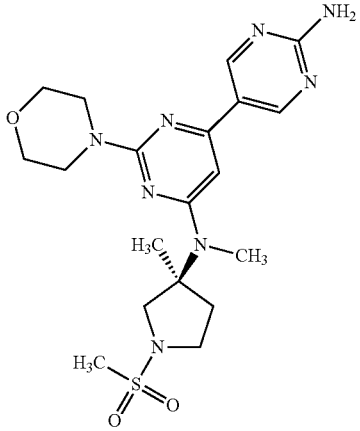 [SMILES: CN(c1cc(-c2cnc(N)nc2)nc(N2CCOCC2)n1)[C@@]1(C)CCN(S(C)(=O)=O)C1]<br>N~6~-methyl-N~6~-[(3S)-3-methyl-1-(methylsulfonyl)pyrrolidin-3-yl]-2-(morpholin-4-yl)-4,5'-bipyrimidine-2',6-diamine | 449.1 | 1H NMR (400 MHz, DMSO-d6) δ 8.92 (s, 2H), 7.03 (s, 2H), 6.46 (s, 1H), 4.05-4.03 (m, 1H), 3.68-3.65 (m, 8H), 3.43-3.40 (m, 2H), 3.26-3.24 (m, 1H), 3.03 (s, 3H), 2.90 (s, 3H), 2.29-2.24 (m, 2H), 1.44 (s, 3H). |
| 14 | 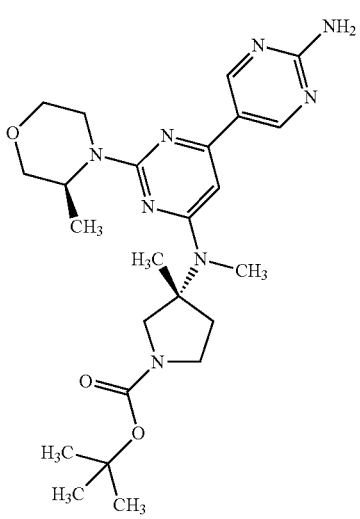 [SMILES: C[C@H]1COCCN1c1nc(-c2cnc(N)nc2)cc(N(C)[C@]2(C)CCN(C(=O)OC(C)(C)C)C2)n1]<br>tert-butyl (3R)-3-[{2'-amino-2-[(3S)-3-methylmorpholin-4-yl]-4,5'-bipyrimidin-6-yl}(methyl)amino]-3-methylpyrrolidine-1-carboxylate | 485.2 | 1H NMR (400 MHz, CDCl3) δ 8.88 (s, 2H), 6.11 (s, 1H), 5.21 (s, 2H), 4.71-4.56 (m, 1H), 4.36-4.27 (m, 1H), 4.25-3.98 (m, 2H), 3.82-3.75 (m, 2H), 3.57-3.48 (m, 3H), 3.31-3.22 (m, 2H), 3.05 (s, 3H), 2.33-2.16 (m, 2H), 1.47-1.44 (m, 12H), 1.31 (d, J = 5.3 Hz, 3H). |

TABLE 1-continued

| Example Number | Structure and Compound Name | LRMS m/z [M + H]+ | 1H NMR |
|---|---|---|---|
| 15 | 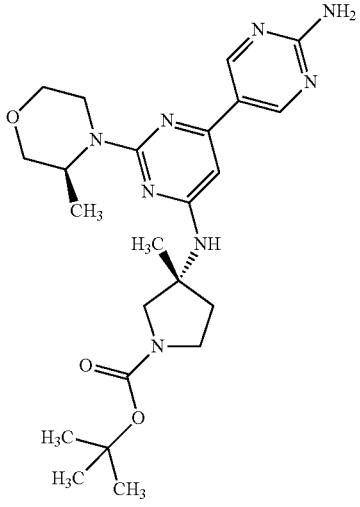 [SMILES: C[C@H]1COCCN1c1nc(N[C@]2(C)CCN(C(=O)OC(C)(C)C)C2)cc(-c2cnc(N)nc2)n1]<br>tert-butyl (3R)-3-({2'-amino-2-[(3S)-3-methylmorpholin-4-yl]-4,5'-bipyrimidin-6-yl}amino)-3-methylpyrrolidine-1-carboxylate | 474.1 | 1H NMR (400 MHz, CDCl3) δ 8.84 (s, 2H), 5.96 (s, 1H), 5.21 (s, 2H), 4.70 (s, 1H), 4.60 (s, 1H), 4.41-4.35 (m, 1H), 3.99 (d, J = 8.0 Hz, 1H), 3.77-3.73 (m, 3H), 3.57-3.43 (m, 4H), 3.28-3.20 (m, 1H), 2.50-2.38 (m, 1H), 1.95-1.85 (m, 1H), 1.62 (s, 3H), 1.45 (s, 9H), 1.32-1.28 (m, 3H). |
| 16 | 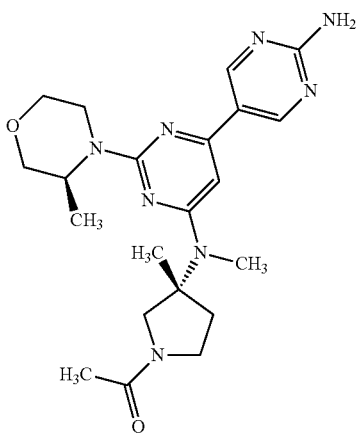 [SMILES: CC(=O)N1CC[C@@](C)(N(C)c2cc(-c3cnc(N)nc3)nc(N3CCOC[C@@H]3C)n2)C1]<br>1-{(3R)-3-[{2'-amino-2-[(3S)-3-methylmorpholin-4-yl]-4,5'-bipyrimidin-6-yl}(methyl)amino]-3-methylpyrrolidin-1-yl}ethanone | 427.1 | 1H NMR (400 MHz, CDCl3) δ 8.84 (s, 2H), 5.96 (s, 1H), 5.31-5.28 (m, 2H), 4.69-4.66 (m, 1H), 4.45-4.35 (m, 2H), 4.05-3.95 (m, 1H), 3.81-3.72 (m, 3H), 3.60-3.40 (m, 2H), 3.30-3.20 (m, 2H), 3.05-3.04 (m, 3H), 2.55-2.30 (m, 1H), 2.20-2.18 (m, 1H), 2.06-2.04 (m, 3H), 1.46 (d, J = 5.6 Hz, 3H), 1.32-1.30 (m, 3H). |

TABLE 1-continued

| Example Number | Structure and Compound Name | LRMS m/z [M + H]+ | 1H NMR |
|---|---|---|---|
| 17 | 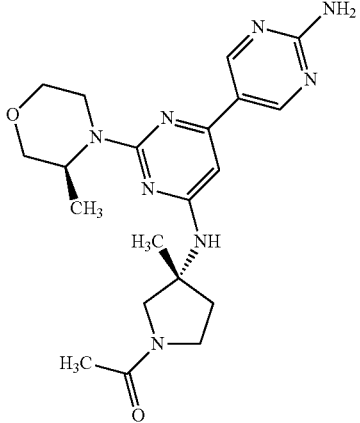 [SMILES: CC(=O)N1CC[C@@](C)(Nc2cc(-c3cnc(N)nc3)nc(N3CCOC[C@@H]3C)n2)C1]<br>1-[(3R)-3-{{2'-amino-2-[(3S)-3-methylmorpholin-4-yl]-4,5'-bipyrimidin-6-yl}amino)-3-methylpyrrolidin-1-yl]ethanone | 413.1 | 1H NMR (400 MHz, CDCl3) δ 8.34 (s, 2H), 5.97 (s, 1H), 5.25 (s, 2H), 4.75-4.65 (m, 2H), 4.38 (t, J = 11.2 Hz, 1H), 4.07-3.95 (m, 1H), 3.90-3.70 (m, 3H), 3.70-3.50 (m, 4H), 3.35-3.20 (m, 1H), 2.85-2.75 (m, 1H), 2.35-2.20 (m, 1H), 2.04 (d, J = 16.0 Hz, 3H), 1.63 (s, 3H), 1.32 (d, J = 6.8 Hz, 3H). |
| 18 | 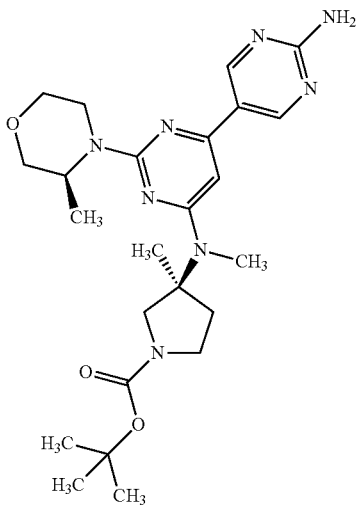 [SMILES: C[C@H]1COCCN1c1nc(-c2cnc(N)nc2)cc(N(C)[C@@]2(C)CCN(C(=O)OC(C)(C)C)C2)n1]<br>tert-butyl (3S)-3-[{2'-amino-2-[(3S)-3-methylmorpholin-4-yl]-4,5'-bipyrimidin-6-yl}(methyl)amino]-3-methylpyrrolidine-1-carboxylate | 485.2 | 1H NMR (400 MHz, CDCl3) δ 8.88 (s, 2H), 6.11 (s, 1H), 5.25 (s, 2H), 4.71-4.69 (m, 1H), 4.35-4.34 (m, 1H), 4.17-4.14 (m, 1H), 4.00-3.99 (m, 1H), 3.82-3.72 (m, 2H), 3.60-3.48 (m, 3H), 3.30-3.29 (m, 2H), 3.04 (s, 3H), 2.27-2.12 (m, 2H), 1.47-1.46 (m, 12H), 1.33 (d, J = 6.8 Hz (3H). |

TABLE 1-continued

| Example Number | Structure and Compound Name | LRMS m/z [M + H]+ | 1H NMR |
|---|---|---|---|
| 19 | 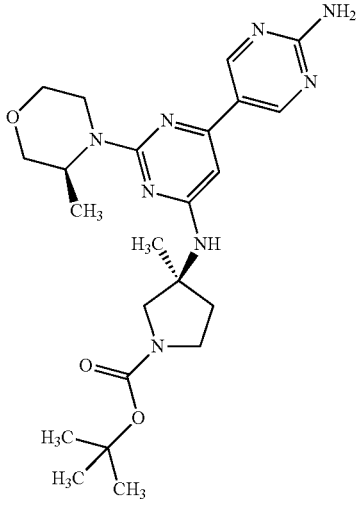 [SMILES: C[C@H]1COCCN1c1nc(N[C@@]2(C)CCN(C(=O)OC(C)(C)C)C2)cc(-c2cnc(N)nc2)n1]<br>tert-butyl (3S)-3-({2'-amino-2-[(3S)-3-methylmorpholin-4-yl]-4,5'-bipyrimidin-6-yl}amino)-3-methylpyrrolidine-1-carboxylate | 471.2 | 1H NMR (400 MHz, CDCl3) δ 8.84 (s, 2H), 5.96 (s, 1H), 5.28 (s, 2H), 4.69-4.68 (m, 2H), 4.45-4.35 (m, 1H), 4.05-3.95 (m, 1H), 3.81-3.72 (m, 3H), 3.60-3.40 (m, 4H), 3.30-3.20 (m, 1H), 2.55-2.30 (m, 1H), 1.96-1.89 (m, 1H), 1.60 (s, 3H), 1.46, (d, J = 5.6 Hz, 9H), 1.31 (d, J = 6.8 Hz, 3H). |
| 20 | 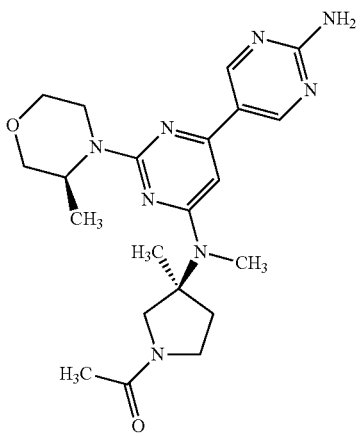 [SMILES: CC(=O)N1CC[C@](C)(N(C)c2cc(-c3cnc(N)nc3)nc(N3CCOC[C@@H]3C)n2)C1]<br>1-[(3S)-3-[{2'-amino-2-[(3S)-3-methylmorpholin-4-yl]-4,5'-bipyrimidin-6-yl}(methyl)amino]-3-methylpyrrolidin-1-yl}ethanone | 427.0 | 1H NMR (400 MHz, CDCl3) δ 8.88 (s, 2H), 6.12 (s, 1H), 5.31 (s, 2H), 4.68-4.67 (m, 1H), 4.42-4.37 (m, 2H), 3.80-3.75 (m, 1H), 3.67-3.52 (m, 6H), 3.41-3.25 (m, 1H), 3.07-3.05 (m, 3H), 2.26-2.20 (m, 1H), 2.18-2.11 (m, 1H), 2.07-2.04 (m, 3H), 1.50-1.46 (m, 3H), 1.37-1.33 (m, 3H). |

TABLE 1-continued

| Example Number | Structure and Compound Name | LRMS m/z [M + H]+ | 1H NMR |
|---|---|---|---|
| 21 | 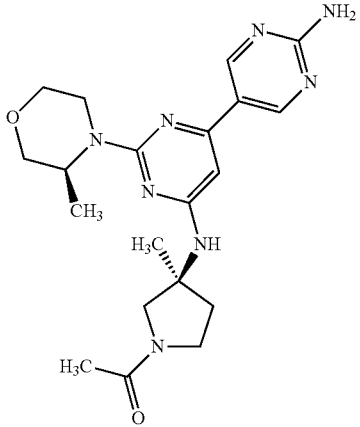 [SMILES: CC(=O)N1CC[C@](C)(Nc2cc(-c3cnc(N)nc3)nc(N3CCOC[C@@H]3C)n2)C1]<br>1-[(3S)-3-({2'-amino-2-[(3S)-3-methylmorpholin-4-yl]-4,5'-bipyrimidin-6-yl}amino)-3-methylpyrrolidin-1-yl]ethanone | 413.1 | 1H NMR (400 MHz, CDCl3) δ 8.34 (s, 2H), 5.97 (s, 1H), 5.25 (s, 2H), 4.75-4.65 (m, 2H), 4.38 (t, J = 11.2 Hz, 1H), 4.07-3.95 (m, 1H), 3.90-3.70 (m, 3H), 3.70-3.50 (m, 4H), 3.35-3.20 (m, 1H), 2.85-2.75 (m, 1H), 2.35-2.20 (m, 1H), 2.04 (d, J = 16.0 Hz, 3H), 1.63 (s, 3H), 1.32 (d, J = 6.8 Hz, 3H). |
| 22 | 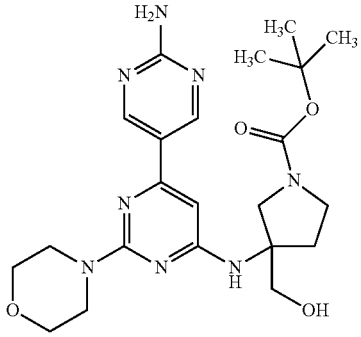 [SMILES: CC(C)(C)OC(=O)N1CCC(CO)(Nc2cc(-c3cnc(N)nc3)nc(N3CCOCC3)n2)C1]<br>tert-butyl 3-{[2'-amino-2-(morpholin-4-yl)-4,5'-bipyrimidin-6-yl]amino}-3-(hydroxymethyl)pyrrolidine-1-carboxylate | 473.2 | 1H NMR (400 MHz, DMSO-d6) δ 8.73 (s, 2H), 6.66 (s, 1H), 6.61 (s, 2H), 6.27 (s, 1H), 4.67 (t, J = 5.6 Hz, 1H), 3.78-3 65 (m, 11H), 3.49 (d, J = 11.4 Hz, 1H), 3.42-3.30 (m, 2H), 2.30-2.21 (m, 1H), 2.16-2.07 (m, 1H), 1.41 (s, 9H). |
| 23 | 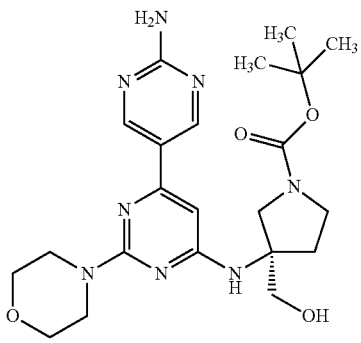 [SMILES: CC(C)(C)OC(=O)N1CC[C@@](CO)(Nc2cc(-c3cnc(N)nc3)nc(N3CCOCC3)n2)C1]<br>tert-butyl (3R)-3-{[2'-amino-2-(morpholin-4-yl)-4,5'-bipyrimidin-6-yl]amino}-3-(hydroxymethyl)pyrrolidine-1-carboxylate | 472.9 | 1H NMR (700 MHz, DMSO-d6) δ ppm 8.73 (br s, 2H), 7.01 (d, J = 16.91 Hz, 1H), 6.89 (br s, 2H), 6.17-6.23 (m, 1H), 3.75 (s, 9H), 3.62 (br s, 3H), 3.21-3.38 (m, 2H), 2.01-2.19 (m, 2H), 1.30-1.39 (m, 9H). |

TABLE 1-continued

| Example Number | Structure and Compound Name | LRMS m/z [M + H]+ | 1H NMR |
|---|---|---|---|
| 24 | 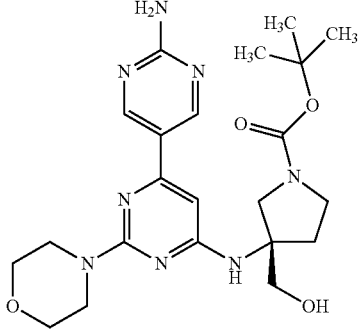 [SMILES: CC(C)(C)OC(=O)N1CC[C@](CO)(Nc2cc(-c3cnc(N)nc3)nc(N3CCOCC3)n2)C1]<br>tert-butyl (3S)-3-{[2'-amino-2-(morpholin-4-yl)-4,5'-bipyrimidin-6-yl]amino}-3-(hydroxymethyl)pyrrolidine-1-carboxylate | 473.0 | 1H NMR (400 MHz, 80° C., DMSO-d6) δ 8.73 (s, 2H), 6.67 (br s, 1H), 6,62 (br s, 2H), 6.27 (s, 1H), 4.70-4.66 (m, 1H), 3.79-3 65 (m, 11H), 3.50 (d, J = 11.4 Hz, 1H), 3.43-3.29 (m, 2H), 2.30-2.21 (m, 1H), 2.16-2.08 (m, 1H), 1.41 (s, 9H). |
| 25 | 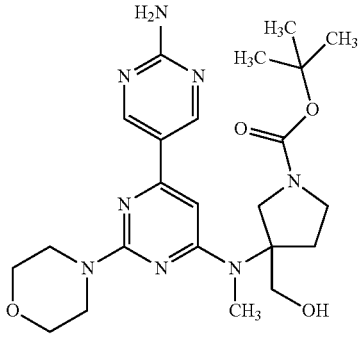 [SMILES: CN(c1cc(-c2cnc(N)nc2)nc(N2CCOCC2)n1)C1(CO)CCN(C(=O)OC(C)(C)C)C1]<br>tert-butyl 3-{[2'-amino-2-(morpholin-4-yl)-4,5'-bipyrimidin-6-yl](methyl)amino}-3-(hydroxymethyl)pyrrolidine-1-carboxylate | 487.25 | 1H NMR (400 MHz, DMSO-d6) δ 8.87 (s, 2H), 6.63 (s, 2H), 6.37 (s, 1H), 4.69 (t, J = 5.6 Hz, 1H), 4.07 (d, J = 11.2 Hz, 1H), 4.01-3.87 (m, 1H), 3.83-3.57 (m, 10H), 3.50 (d, J = 11.7 Hz, 1H), 3.43-3.34 (m, 1H), 3.22 (td, J = 10.3, 7.1 Hz, 1H), 3.10 (s, 3H), 2.27-2.14 (m, 1H), 1.41 (s, 9H). |
| 26* | 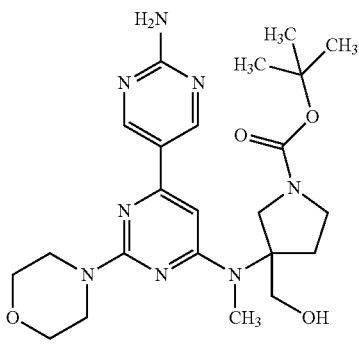 [SMILES: CN(c1cc(-c2cnc(N)nc2)nc(N2CCOCC2)n1)C1(CO)CCN(C(=O)OC(C)(C)C)C1]<br>tert-butyl 3-{[2'-amino-2-(morpholin-4-yl)-4,5'-bipyrimidin-6-yl](methyl)amino}-3-(hydroxymethyl)pyrrolidine-1-carboxylate | 486.9 | 1H NMR (700 MHz, DMSO-d6) δ 8.91 (s, 2H), 7.01 (br s, 2H), 6.41 (s, 1H), 4.13-3.90 (m, 2H), 3.72-3.55 (m, 8H), 3.50-3.35 (m, 1H), 3.07 (s, 3H), 2.20-2.08 (m, 1H), 1.40-1.37 (m, 12H). |

TABLE 1-continued

| Example Number | Structure and Compound Name | LRMS m/z [M + H]+ | 1H NMR |
|---|---|---|---|
| 27* | 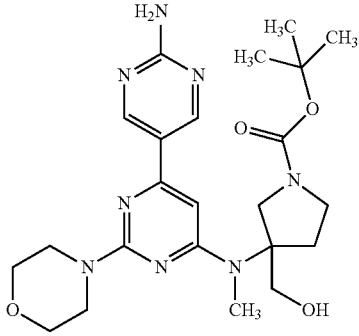 [SMILES: CN(c1cc(-c2cnc(N)nc2)nc(N2CCOCC2)n1)C1(CO)CCN(C(=O)OC(C)(C)C)C1]<br>tert-butyl 3-{[2'-amino-2-(morpholin-4-yl)-4,5'-bipyrimidin-6-yl](methyl)amino}-3-(hydroxymethyl)pyrrolidine-1-carboxylate | 486.9 | 1H NMR (700 MHz, DMSO-d$_6$) δ 7.01 (br s, 2H), 6.41 (s, 1H), 4.14-3.91 (m, 2H), 3.71-3.58 (m, 7H), 3.49-3.33 (m, 1H), 3.23-3.11 (m, 1H), 3.07 (s, 3H), 2.22-2.07 (m, 1H), 1.38 (br s, 12H). |
| 28 | 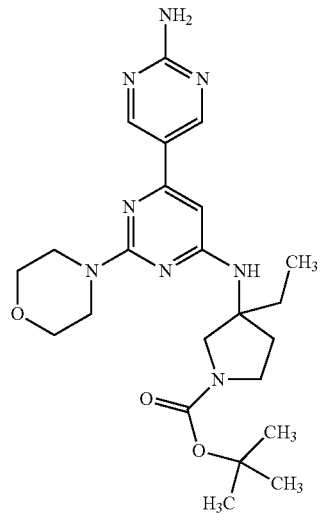 [SMILES: CCC1(Nc2cc(-c3cnc(N)nc3)nc(N3CCOCC3)n2)CCN(C(=O)OC(C)(C)C)C1]<br>tert-butyl 3-{[2'-amino-2-(rnorpholin-4-yl)-4,5'-bipyrimidin-6-yl]amino}-3-ethylpyrrolidine-1-carboxylate | 471.2 | 1H NMR (400 MHz, CDCl$_3$) δ 8.85 (s, 2H), 6.00 (s, 1H), 5.25 (s, 2H), 4.54 (s, 1H), 3.79 (s, 9H), 3.52-3.32 (m, 3H), 2.52-2.29 (m, 1H), 2.27-1.84 (m, 3H), 1.47-1.46 (d, J = 4.0 Hz, 9H), 0.94-0.84 (m, 3H). |
| 29 | 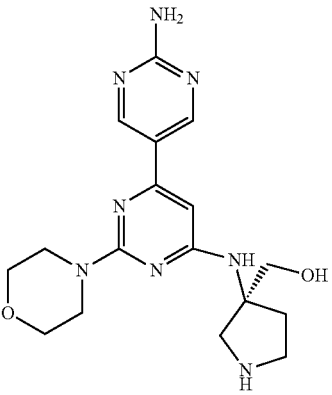 [SMILES: Nc1ncc(-c2cc(N[C@@]3(CO)CCNC3)nc(N3CCOCC3)n2)cn1]<br>[(3S)-3-{[2'-amino-2-(morpholin-4-yl)-4,5'-bipyrimidin-6-yl]amino}pyrrolidin-3-yl]methanol | 373.2 | 1H NMR (400 MHz, D$_2$O) δ 8.67-8.65 (m, 2H), 6.36-6.32 (m, 1H), 4.18 (d, J = 11.6 Hz, 1H), 4.06 (d, J = 13.1 Hz, 1H), 3.98-3.81 (m, 9H), 3.63-3.52 (m, 3H), 2.57-2.36 (m, 2H). |

TABLE 1-continued

| Example Number | Structure and Compound Name | LRMS m/z [M + H]+ | 1H NMR |
|---|---|---|---|
| 30 | 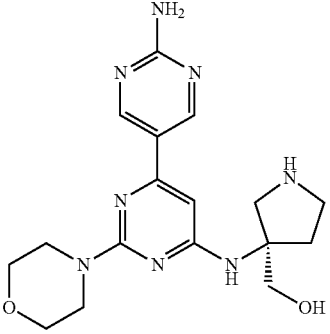 [SMILES: Nc1ncc(-c2cc(N[C@]3(CO)CCNC3)nc(N3CCOCC3)n2)cn1]<br>[(3R)-3-{[2'-amino-2-(morpholin-4-yl)-4,5'-bipyrimidin-6-yl]amino}pyrrolidin-3-yl]methanol | 373.2 | 1H NMR (400 MHz, METHANOL-d4) δ 8.80 (s, 2H), 6.22 (s, 1H), 3.98-3.87 (m, 2H), 3.82-3.70 (m, 8H), 3.39 (d, J = 12.1 Hz, 1H), 3.18 (d, J = 12.1 Hz, 1H), 3.15-3.00 (m, 2H), 2.23-2.07 (m, 2H). |
| 31 | 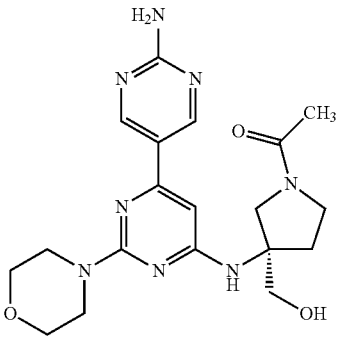 [SMILES: CC(=O)N1CC[C@@](CO)(Nc2cc(-c3cnc(N)nc3)nc(N3CCOCC3)n2)C1]<br>1-[(3R)-3-{[2'-amino-2-(morpholin-4-yl)-4,5'-bipyrimidin-6-yl]amino}-3-(hydroxymethyl)pyrrolidin-1-yl]ethanone | 415.2 | 1H NMR (400 MHz, METHANOL-d4) δ 8.80 (s, 2H), 6.28-6.20 (m, 1H), 4 09-3.85 (m, 3H), 3.75 (s, 8H), 3.70-3.50 (m, 3H), 2.52-2.35 (m, 1H), 2.35-2.11 (m, 1H), 2.05 (d, J = 4.5 Hz, 3H) |
| 32 | 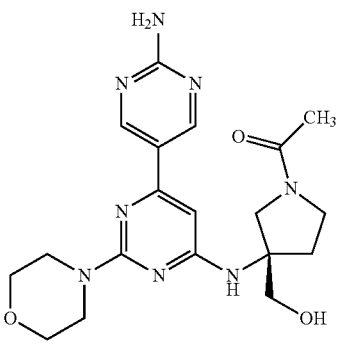 [SMILES: CC(=O)N1CC[C@](CO)(Nc2cc(-c3cnc(N)nc3)nc(N3CCOCC3)n2)C1]<br>1-[(3S)-3-{[2'-amino-2-(morpholin-4-yl)-4,5'-bipyrimidin-6-yl]amino}-3-(hydroxymethyl)pyrrolidin-1-yl]ethanone | 415.2 | 1H NMR (400 MHz, METHANOL-d4) δ 8.87-8.69 (m, 2H), 6.29-6.17 (m, 1H), 4.07-3.87 (m, 3H), 3.75 (s, 8H), 3.70-3.59 (m, 2H), 3.59-3 50 (m, 1H), 2.52-2.34 (m, 1H), 2.34-2.13 (m, 1H), 2.05 (d, J = 4.5 Hz, 3H). |

TABLE 1-continued

| Example Number | Structure and Compound Name | LRMS m/z [M + H]+ | ¹H NMR |
|---|---|---|---|
| 33 | [(3S)-3-{[2'-amino-2-(morpholin-yl)-4,5'-bipyrimidin-6-yl]amino}-1-(methylsulfonyl)pyrrolidin-3-yl]methanol | 451.1 | ¹H NMR (400 MHz, DMSO-d₆) δ 8.73 (s, 2H), 7.02 (s, 1H), 6.97 (s, 2H), 6.24 (s, 1H), 5.00 (br s, 1H), 3.80-3.61 (m, 11H), 3.42-3.31 (m, 3H, partially overlapped with water), 2.83 (s, 3H), 2.34-2.26 (m, 1H), 2.14 (td, J = 12.9, 8.1 Hz, 1H) |
| 34 | methyl (3S)-3-{[2'-amino-2-(morpholin-4-yl)-4,5'-bipyrimidin-6-yl]amino}-3-(hydroxymethyl)pyrrolidine-1-carboxylate | 431.1 | ¹H NMR (400 MHz, 80° C., DMSO-d₆) δ 8.73 (s, 2H), 6.69 (s, 1H), 6.63 (s, 2H), 6.26 (s, 1H), 4.71 (br s, 1H), 3.78-3.74 (m, 3H), 3.71-3.64 (m, 8H), 3.59 (s, 3H), 3.51 (d, J = 11.4 Hz, 1H), 3.47-3.35 (m, 2H), 2.35-2.27 (m, 1H), 2.17-2.08 (m, 1H). |

TABLE 1-continued

| Example Number | Structure and Compound Name | LRMS m/z [M + H]+ | 1H NMR |
|---|---|---|---|
| 35 | 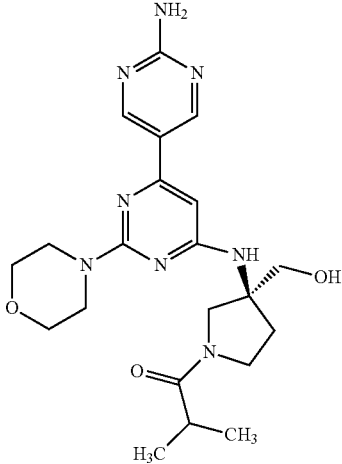 [SMILES: CC(C)C(=O)N1CC[C@](CO)(Nc2cc(-c3cnc(N)nc3)nc(N3CCOCC3)n2)C1]<br>1-[(3S)-3-{[2'-amino-2-(morpholin-4-yl)-4,5'-bipyrimidin-6-yl]amino}-3-(hydroxymethyl)pyrrolidin-1-yl]-2-methylpropan-1-one | 443.2 | 1H NMR (400 MHz, DMSO-d$_6$) δ 8.76-8.70 (m, 2H), 7.01-6.95 (m, 3H), 6.26-6.18 (m, 1H), 4.95 (td, J = 15.8, 5.7 Hz, 1H), 4.00-3.34 (m, 14H), 2.68-2.53 (m, 1H, partially overlapped with DMSO), 2.41-2.01 (m, 2H), 1.03-0.91 (m, 6H). |
| 36 | 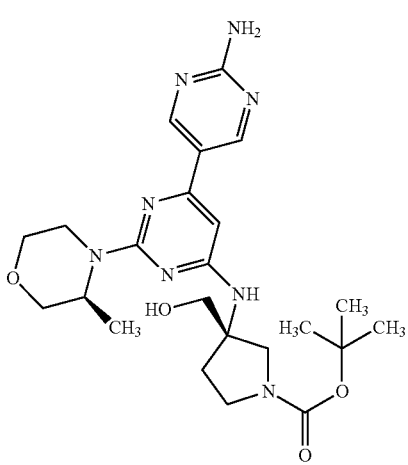 [SMILES: C[C@H]1COCCN1c1nc(N[C@@]2(CO)CCN(C(=O)OC(C)(C)C)C2)cc(-c2cnc(N)nc2)n1]<br>tert-butyl (3S)-3-({2'-amino-2-[(3S)-3-methylmorpholin-4-yl]-4,5'-bipyrimidin-6-yl}amino)-3-(hydroxymethyl)pyrrolidine-1-carboxylate | 487.2 | 1H NMR (400 MHz, DMSO-d$_6$) δ 8.72 (s, 2H), 6.64 (s, 1H), 6.60 (s, 2H), 6.25 (s, 1H), 4.67 (t, J = 5.6 Hz, 1H), 4.64-4.50 (m, 1H), 4.28 (dd, J = 13.7, 1.9 Hz, 1H), 3.90 (dd, J = 11.0, 3.6 Hz, 1H), 3.84-3.66 (m, 4H), 3.65-3.57 (m, 1H), 3.49 (d, J = 11.6 Hz, 1H), 3.46-3.27 (m, 3H), 3.19-3.08 (m, 1H), 2.30-2.18 (m, 1H), 2.18-2.05 (m, 1H), 1.40 (s, 9H), 1.23 (d, J = 6.7 Hz, 3H). |

TABLE 1-continued

| Example Number | Structure and Compound Name | LRMS m/z [M + H]+ | 1H NMR |
|---|---|---|---|
| 37 | 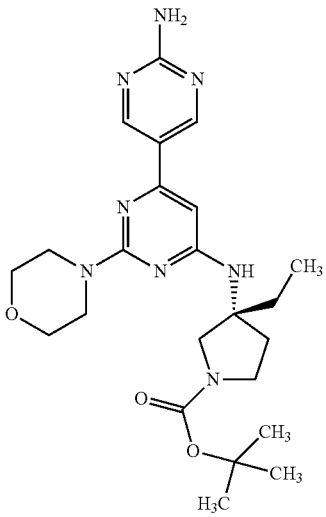 [SMILES: CC[C@@]1(Nc2cc(-c3cnc(N)nc3)nc(N3CCOCC3)n2)CCN(C(=O)OC(C)(C)C)C1]<br>tert-butyl (3R)-3-{[2'-amino-2-(morpholin-4-yl)-4,5'-bipyrimidin-6-yl]amino}-3-ethylpyrrolidine-1-carboxylate | 471.3 | 1H NMR (400 MHz, CDCl3) δ 8.84 (s, 2H), 6.00 (s, 1H), 5.27 (s, 2H), 4.55 (s, 1H), 3.79 (s, 9H), 3.52-3.32 (m, 3H), 2.59-2.29 (m, 1H), 2.25-1.83 (m, 3H), 1.46 (s, 9H), 0.93-0.83 (m, 3H). |
| 38 | 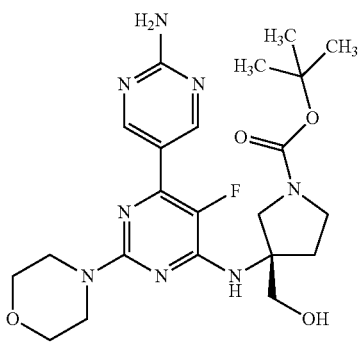 [SMILES: CC(C)(C)OC(=O)N1CC[C@](CO)(Nc2nc(N3CCOCC3)nc(-c3cnc(N)nc3)c2F)C1]<br>tert-butyl (3S)-3-{[2'-amino-5-fluoro-2-(morpholin-4-yl)-4,5'-bipyrimidin-6-yl]amino}-3-(hydroxymethyl)pyrrolidine-1-carboxylate | 491.2 | 1H NMR (400 MHz, DMSO-d6) δ 8.77 (s, 2H), 6.74 (s, 2H), 6.50 (s, 1H), 4.73 (t, J = 5.8 Hz, 1H), 3.82 (d, J = 11.2 Hz, 1H), 3.74-3.80 (m, 1H), 3.69-3.74 (m, 1H), 3.64-3.69 (m, 4H), 3.57-3.64 (m, 4H), 3.52 (d, J = 11.5 Hz, 1H), 3.37-3.45 (m, 1H), 3.27-3.37 (m, 1H), 2.34-2.44 (m, 1H), 2.15 (ddd, J = 12.9, 8.0, 6.4 Hz, 1H), 1.41 (s, 9 H). |
| 39 | 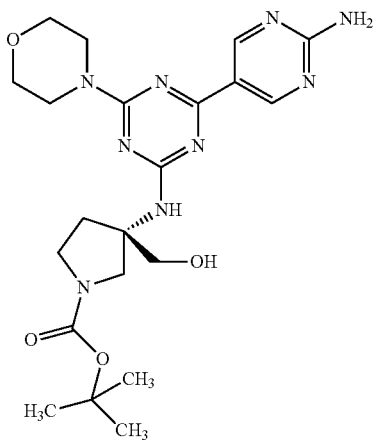 [SMILES: CC(C)(C)OC(=O)N1CC[C@](CO)(Nc2nc(-c3cnc(N)nc3)nc(N3CCOCC3)n2)C1]<br>tert-butyl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate | 474.1 | 1H NMR (400 MHz, DMSO-d6) δ 9.00 (s, 2H), 7.33-7.22 (m, 3H), 4.99-4.94 (m, 1H), 3.76-3.44 (m, 14H), 2.23-2.07 (m, 2H), 1.37 (d, J = 7.2 Hz, 9H). |

TABLE 1-continued
| Example Number | Structure and Compound Name | LRMS m/z [M + H]+ | 1H NMR |
|---|---|---|---|
| 40 | 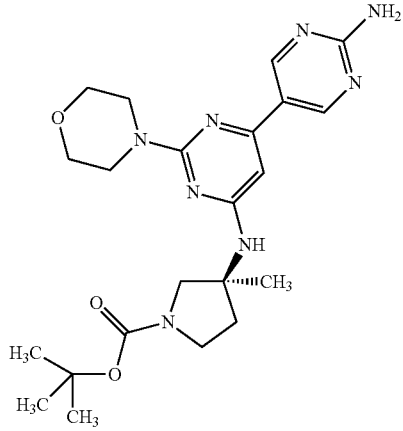 [SMILES: CC(C)(C)OC(=O)N1CC[C@](C)(Nc2cc(-c3cnc(N)nc3)nc(N3CCOCC3)n2)C1]
tert-butyl (3S)-3-{[2'-amino-2-(morpholin-4-yl)-4,5'-bipyrimidin-6-yl]amino}-3-methylpyrrolidine-1-carboxylate | 457.0 | 1H NMR (400 MHz, CDCl3) δ 8.84 (s, 2H), 5.97 (s, 1H), 5.23 (s, 2H), 4.64 (br s, 1H), 3.80-3.70 (m, 10H), 3.55-3.40 (m, 2H), 2.60-2.35 (m, 1H), 2.00-1.90 (m, 1H), 1.59 (s, 3H), 1.45 (s, 9H). |
| 41 | 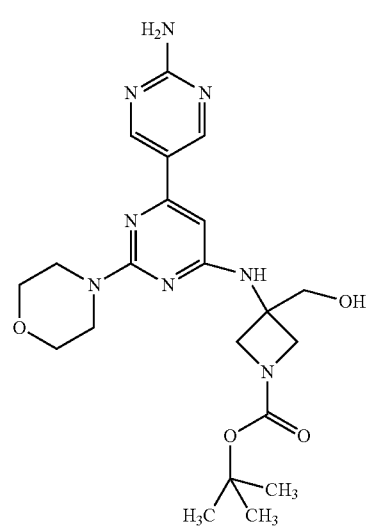 [SMILES: CC(C)(C)OC(=O)N1CC(CO)(Nc2cc(-c3cnc(N)nc3)nc(N3CCOCC3)n2)C1]
tert-butyl 3-{[2'-amino-2-(morpholin-4-yl)-4,5'-bipyrimidin-6-yl]amino}-3-(hydroxymethyl)azetidine-1-carboxylate | 459.2 | 1H NMR (400 MHz, DMSO-d6) δ 8.74 (s, 2H), 7.45 (s, 1H), 7.02 (s, 2H), 6.18 (s, 1H), 5.14 (d, J = 5.8 Hz, 1H), 3.92-3.85 (m, 4H), 3.69-3.63 (m, 10H), 1.37 (s, 9H). |

TABLE 1-continued

| Example Number | Structure and Compound Name | LRMS m/z [M + H]+ | 1H NMR |
|---|---|---|---|
| 42 | 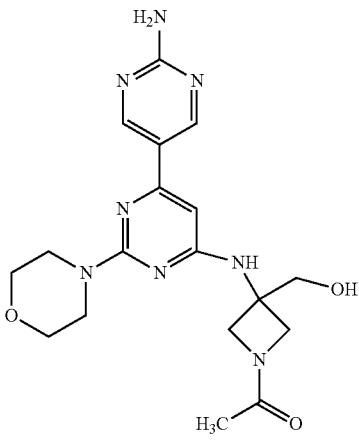 [SMILES: CC(=O)N1CC(CO)(Nc2cc(-c3cnc(N)nc3)nc(N3CCOCC3)n2)C1]<br>1-[3-{[2'-amino-2-(morpholin-4-yl)-4,5'-bipyrimidin-6-yl]amino}-3-(hydroxymethyl)azetidin-1-yl]ethanone | 401.2 | 1H NMR (400 MHz, DMSO-$d_6$) δ 8.75 (s, 2H), 7.46 (s, 1H), 7.01 (s, 2H), 6.20 (s, 1H), 5.15- 5.14 (m, 1H), 4.16- 4.15 (m, 2H), 3.92-3.85 (m, 2H), 3.72 (d, J = 5.6 Hz, 2H), 3.65-3.64 (m, 8H), 1.77 (s, 3H). |
| 43 | 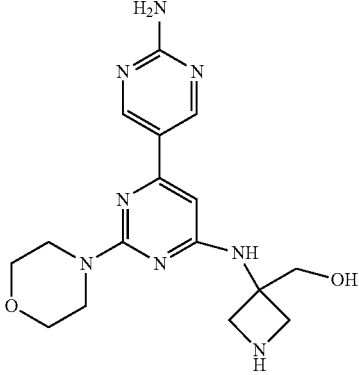 [SMILES: Nc1ncc(-c2cc(NC3(CO)CNC3)nc(N3CCOCC3)n2)cn1]<br>(3-{[2'-amino-2-(morpholin-4-yl)-4,5'-bipyrimidin-6-yl]amino}azetidin-3-yl)methanol | 359.1 | 1H NMR (400 MHz, $D_2O$) δ 8.75-8.70 (m, 2H), 6.32 (s, 1H), 4.40-4.37 (m, 2H), 4.31-4.28 (m, 2H), 3.93 (s, 2H), 3.81-3.73 (m, 8H). |
| 44 | 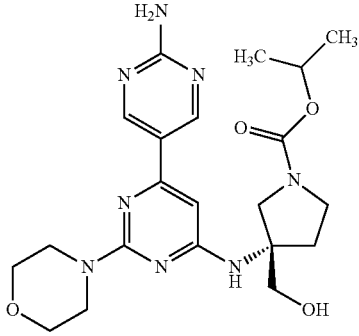 [SMILES: CC(C)OC(=O)N1CC[C@](CO)(Nc2cc(-c3cnc(N)nc3)nc(N3CCOCC3)n2)C1]<br>propan-2-yl (3S)-3-{[2'-amino-2-(morpholin-4-yl)-4,5'-bipyrimidin-6-yl]amino}-3-(hydroxymethyl)pyrrolidine-1-carboxylate | 459.2 | 1H NMR (400 MHz, METHANOL-$d_4$) δ 8.81 (s, 2H), 6.24 (s, 1H), 3.99-3.86 (m, 3H), 3.76-3.74 (m, 7H), 3.62-3.49 (m, 4H), 2.34-2.21 (m, 3H), 1.25-1.21 (m, 6H). |

TABLE 1-continued

| Example Number | Structure and Compound Name | LRMS m/z [M + H]+ | 1H NMR |
|---|---|---|---|
| 45 | 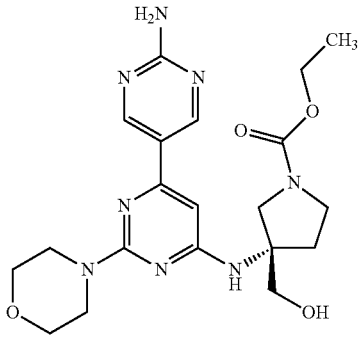 [SMILES: CCOC(=O)N1CC[C@](CO)(Nc2cc(-c3cnc(N)nc3)nc(N3CCOCC3)n2)C1]ethyl (3S)-3-{[2'-amino-2-(morpholin-4-yl)-4,5'-bipyrimidin-6-yl]amino}-3-(hydroxymethyl)pyrrolidine-1-carboxylate | 445.1 | 1H NMR (400 MHz, DMSO-$d_6$) δ 8.71 (s, 2H), 7.01-6.99 (m, 2H), 6.23 (s, 1H), 4.95 (br s, 1H) 4.01-3.99 (m, 2H) 3.73-3.65 (m, 9H) 3.45-3.44 (m, 3H) 2.23-1.98 (m, 2H) 1.23-1.14 (m, 3H). |
| 46 | 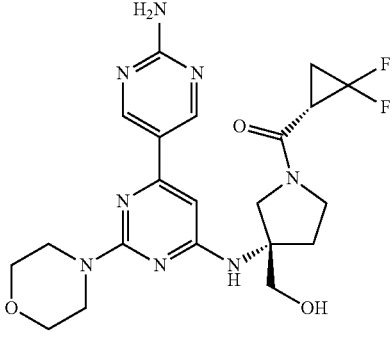 [SMILES: Nc1ncc(-c2cc(N[C@@]3(CO)CCN(C(=O)[C@@H]4CC4(F)F)C3)nc(N3CCOCC3)n2)cn1][(3S)-3-{[2'-amino-2-(morpholin-4-yl)-4,5'-bipyrimidin-6-yl]amino}-3-(hydroxymethyl)pyrrolidin-1-yl][(1S)-2,2-difluorocyclopropyl]methanone | 477.2 | 1H NMR (400 MHz, METHANOL-$d_4$) δ 8.83 (s, 2H), 6.26 (s, 1H), 4.14-4.01 (m, 2H), 3.93-3.58 (m, 10H), 2.84-2.78 (m, 1H), 2.52-2.32 (m, 3H), 2.05-1.78 (m, 3H). |
| 47 | 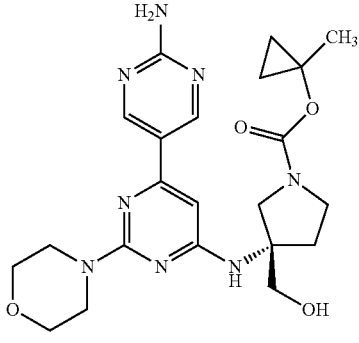 [SMILES: CC1(OC(=O)N2CC[C@](CO)(Nc3cc(-c4cnc(N)nc4)nc(N4CCOCC4)n3)C2)CC1]1-methylcyclopropyl (3S)-3-{[2'-amino-2-(morpholin-4-yl)-4,5'-bipyrimidin-6-yl]amino}-3-(hydroxymethyl)pyrrolidine-1-carboxylate | 471.0 | 1H NMR (400 MHz, METHANOL-$d_4$) δ 8.80 (s, 2H), 6.22 (s, 1H), 4.01-3.75 (m, 10H), 3.55-3.44 (m, 4H), 2.33-2.03 (m, 3H), 1.52-1.51 (m, 2H), 1.33-1.29 (m, 3H), 0.91-0.90 (m, 2H), 0.63-0.62 (m, 1H). |

TABLE 1-continued

| Example Number | Structure and Compound Name | LRMS m/z [M + H]+ | 1H NMR |
|---|---|---|---|
| 48 | 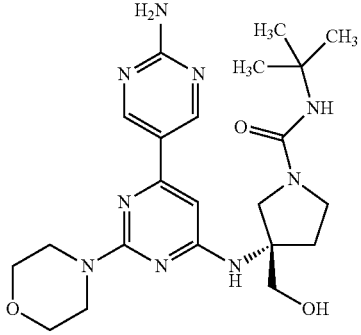 [SMILES: CC(C)(C)NC(=O)N1CC[C@](CO)(Nc2cc(-c3cnc(N)nc3)nc(N3CCOCC3)n2)C1]<br>(3S)-3-{[2'-amino-2-(morpholin-4-yl)-4,5'-bipyrimidin-6-yl]amino}-N-tert-butyl-3-(hydroxymethyl)pyrrolidine-1-carboxamide | 472.0 | 1H NMR (400 MHz, METHANOL-d4) δ 8.79 (s, 2H), 6.22 (s, 1H), 4.01-3.98 (m, 1H), 3.86-3.84 (m, 1H), 3.79-3.75 (m, 10H), 3.59-3.56 (m, 1H), 3.31-3.30 (m, 3H), 2.39-2.35 (m, 1H), 2.24-2.19 (m, 1H), 1.33 (s, 9H). |
| 49 | 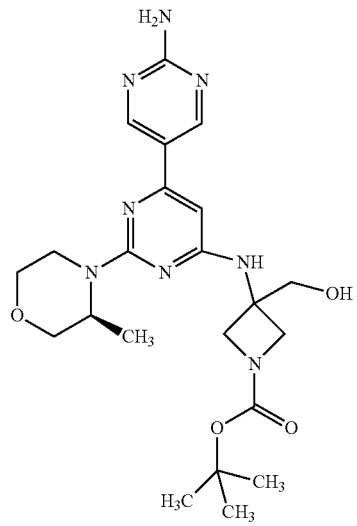 [SMILES: C[C@H]1COCCN1c1nc(NC2(CO)CN(C(=O)OC(C)(C)C)C2)cc(-c2cnc(N)nc2)n1]<br>tert-butyl 3-({2'-amino-2-[(3S)-3-methylmorpholin-4-yl]-4,5'-bipyrimidin-6-yl}amino)-3-(hydroxymethyl)azetidine-1-carboxylate | 473.1 | 1H NMR (400 MHz, METHANOL-d4) δ 8.83 (s, 2H), 6.23 (s, 1H), 4.67 (s, 1H), 4.34 (d, J = 12.4 Hz, 1H), 4.10-3.91 (m, 7H), 3.77-3.73 (m, 2H), 3.55 (m, 1H), 3.23 (m, 1H), 1.47 (s, 9H), 1.28 (d, J = 7.2 Hz, 3H). |
| 50 | 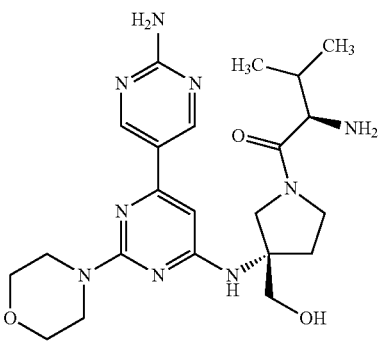 [SMILES: CC(C)[C@@H](N)C(=O)N1CC[C@](CO)(Nc2cc(-c3cnc(N)nc3)nc(N3CCOCC3)n2)C1]<br>(2R)-2-amino-1-[(3S)-3-{[2'-amino-2-(morpholin-4-yl)-4,5'-bipyrimidin-6-yl]amino}-3-(hydroxymethyl)pyrrolidin-1-yl]-3-methylbutan-1-one | 472.2 | 1H NMR (400 MHz, METHANOL-d4) δ 8.53 (s, 2H), 6.19-6.18 (m, 1H), 4.13-3.98 (m, 4H), 3.86-3.60 (m, 11H), 2.50-2.40 (m, 1H), 2.25-2.13 (m, 2H), 1.01-0.91 (m, 6H). |

TABLE 1-continued

| Example Number | Structure and Compound Name | LRMS m/z [M + H]+ | ¹H NMR |
|---|---|---|---|
| 51 | 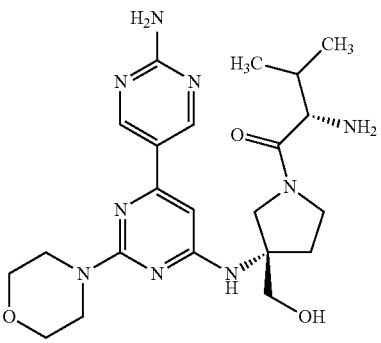 [SMILES: CC(C)[C@H](N)C(=O)N1CC[C@](CO)(Nc2cc(-c3cnc(N)nc3)nc(N3CCOCC3)n2)C1]<br>(2S)-2-amino-1-[(3S)-3-{[2'-amino-2-(morpholin-4-yl)-4,5'-bipyrimidin-6-yl]amino}-3-(hydroxymethyl)pyrrolidin-1-yl]-3-methylbutan-1-one | 472.1 | ¹H NMR (400 MHz, METHANOL-$d_4$) δ 8.59 (s, 2H), 6.22 (d, J = 16.0 Hz, 1H), 4.22-4.00 (m, 3H), 3.82-3.68 (m, 12H), 2.39-2.02 (m, 3H), 1.00-0.86 (m, 6H). |
| 52 | 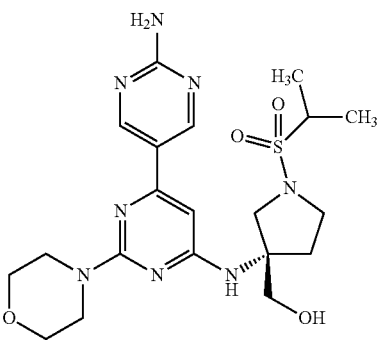 [SMILES: CC(C)S(=O)(=O)N1CC[C@](CO)(Nc2cc(-c3cnc(N)nc3)nc(N3CCOCC3)n2)C1]<br>[(3S)-3-{[2'-amino-2-(morpholin-4-yl)-4,5'-bipyrimidin-6-yl]amino}-1-(propan-2-ylsulfonyl)pyrrolidin-3-yl]methanol | 479.3 | ¹H NMR (400 MHz, METHANOL-$d_4$) δ 8.81 (s, 2H), 6.24 (s, 1H), 4.02-3.99 (m, 2H), 3.96-3.89 (m, 1H), 3.87-3.85 (m, 8H), 3.60-3.54 (m, 4H), 2.33-2.28 (m, 2H), 1.32-1.29 (m, 6H). |
| 53 | 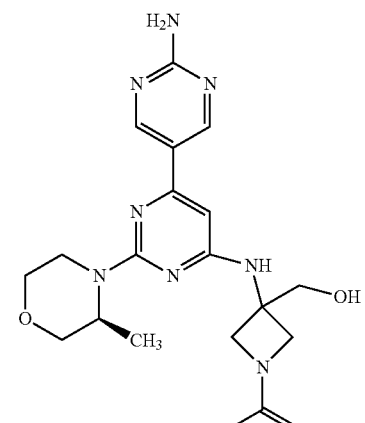<br>1-[3-({2'-amino-2-[(3S)-3-methylmorpholin-4-yl]-4,5'-bipyrimidin-6-yl}amino)-3-(hydroxymethyl)azetidin-1-yl]ethanone | 415.1 | ¹H NMR (400 MHz, METHANOL-$d_4$) δ 8.82 (s, 2H), 6.23 (s, 1H), 4.66-4.60 (m, 1H), 4.39-4.29 (m, 3H), 4.14-4.08 (m, 2H), 3.95-3.90 (m, 2H), 3.76-3.71 (m, 2H), 3.60-3.55 (m, 1H), 3.25-3.20 (m, 2H), 1.91-1.90 (m, 3H), 1.28-1.26 (m, 3H). |

TABLE 1-continued

| Example Number | Structure and Compound Name | LRMS m/z [M + H]+ | 1H NMR |
|---|---|---|---|
| 54 | 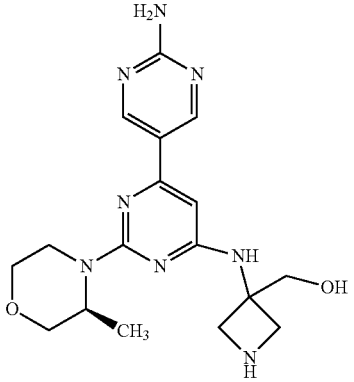 [SMILES: C[C@H]1COCCN1c1nc(NC2(CO)CNC2)cc(-c2cnc(N)nc2)n1]<br>[3-({2'-amino-2-[(3S)-3-methylmorpholin-4-yl]-4,5'-bipyrimidin-6-yl}amino)azetidin-3-yl]methanol | 373.0 | 1H NMR (400 MHz, METHANOL-d4) δ 8.82 (s, 2H), 6.37 (s, 1H), 4.52-4.35 (m, 4H), 4.09-4.02 (m, 2H), 3.88-3.75 (m, 4H), 3.60-3.48 (m, 3H), 1.40-1.38 (m, 3H). |
| 55 | 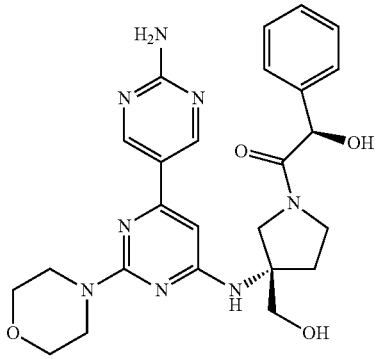 [SMILES: Nc1ncc(-c2cc(N[C@@]3(CO)CCN(C(=O)[C@H](O)c4ccccc4)C3)nc(N3CCOCC3)n2)cn1]<br>(2R)-1-[(3S)-3-{[2'-amino-2-(morpholin-4-yl)-4(5'-bipyrimidin-6-yl]amino}-3-(hydroxymethyl)pyrrolidin-1-yl]-2-hydroxy-2-phenylethanone | 507.0 | 1H NMR (400 MHz, METHANOL-d4) δ 8.79-8.77 (m, 2H), 7.40-7.26 (m, 5H), 6.16-6.09 (m, 1H), 5.30-5.23 (m, 1H), 4.22-3.73 (m, 14H), 2.21-2.12 (m, 3H). |
| 56 | 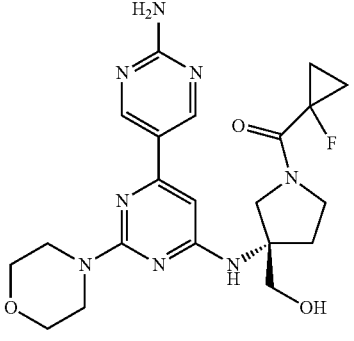 [SMILES: Nc1ncc(-c2cc(N[C@@]3(CO)CCN(C(=O)C4(F)CC4)C3)nc(N3CCOCC3)n2)cn1]<br>[(3S)-3-{[2'-amino-2-(morpholin-4-yl)-4,5'-bipyrimidin-6-yl]amino}-3-(hydroxymethyl)pyrrolidin-1-yl](1-fluorocyclopropyl)methanone | 458.3 | 1H NMR (400 MHz, DMSO-d6) δ 8.73 (s, 2H), 7.09 (d, J = 10.8 Hz, 1H), 7.02 (s, 2H), 6.25-6.23 (m, 1H), 5.03-5.00 (m, 1H), 4.23-4.10 (m, 1H), 3.89-3.77 (m, 4H), 3.66 (s, 6 H), 3.57-3.49 (m, 2H), 3.17 (d, J = 5.2 Hz, 1H), 2.37-2.07 (m, 2H), 1.24-1.08 (m, 4H). |

TABLE 1-continued

| Example Number | Structure and Compound Name | LRMS m/z [M + H]+ | 1H NMR |
|---|---|---|---|
| 57 | 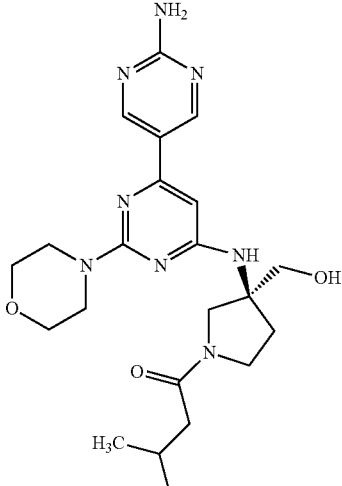<br>1-[(3S)-3-{[2'-amino-2-(morpholin-4-yl)-4,5'-bipyrimidin-6-yl]amino}-3-(hydroxymethyl)pyrrolidin-1-yl]-3-methylbutan-1-one | 457.3 | $^1$H NMR (400 MHz, METHANOL-$d_4$) δ 8.82 (s, 2H), 6.25 (d, J = 2.8 Hz, 1H), 4.21 (d, J = 11.6 Hz, 1H), 4.03-3.93 (m, 3H), 3.78-3.60 (m, 10H), 2.47-2.04 (m, 6H), 1.00-0.92 (m, 6H). |
| 58 | 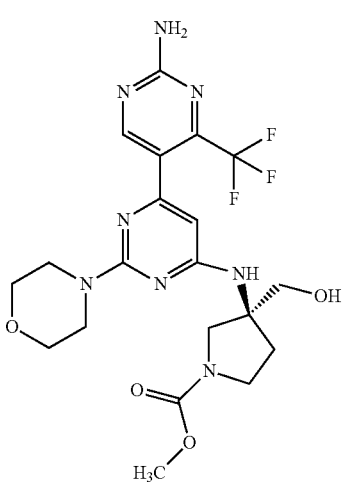 [SMILES: COC(=O)N1CC[C@](CO)(Nc2cc(-c3cnc(N)nc3C(F)(F)F)nc(N3CCOCC3)n2)C1]<br>methyl (3S)-3-{[2'-amino-2-(morpholin-4-yl)-4'-(trifluoromethy)-4,5'-bipyrimidin-6-yl]amino}-3-(hydroxymethyl)pyrrolidine-1-carboxylate | 499.1 | $^1$H NMR (400 MHz, CDCl$_3$) δ 8.55 (s, 1H), 5.83 (s, 1H), 5.42 (s, 2H), 4.82 (s, 1H), 4.37-4.28 (m, 1H), 3.94-3.89 (m, 2H), 3.75-3.71 (m, 13H), 3.58-3.52 (m, 2H), 2.36-2.20 (m, 2H) |

TABLE 1-continued

| Example Number | Structure and Compound Name | LRMS m/z [M + H]+ | 1H NMR |
|---|---|---|---|
| 59 | 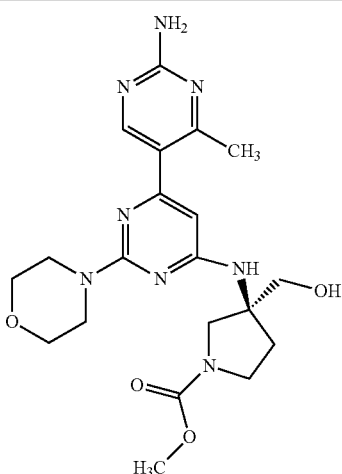<br>methyl (3S)-3-{[2'-amino-4'-methyl-2-(morpholin-4-yl)-4,5'-bipyrimidin-6-yl]amino}-3-(hydroxymethyl)pyrrolidine-1-carboxylate | 445.2 | 1H NMR (400 MHz, CDCl$_3$) δ 8.31 (s, 1H), 5.79 (s, 1H), 5.14 (s, 2H), 4.85 (s, 1H), 4.67 (br s, 1H), 3.97-3.85 (m, 2H), 3.75-3.70 (m, 13H), 3.58-3.52 (m, 2H), 2.51 (s, 3H), 2.37-2.17 (m, 2H). |
| 60 | 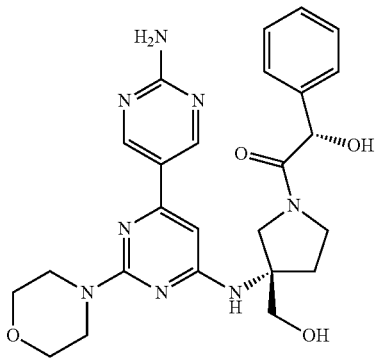 [SMILES: Nc1ncc(-c2cc(N[C@@]3(CO)CCN(C(=O)[C@@H](O)c4ccccc4)C3)nc(N3CCOCC3)n2)cn1]<br>(2S)-1-[(3S)-3-{[2'-amino-2-(morpholin-4-yl)-4,5'-bipyrimidin-6-yl]amino}-3-(hydroxymethyl)pyrrolidin-1-yl]-2-hydroxy-2-phenylethanone | 507.0 | 1H NMR (400 MHz, METHANOL-d$_4$) δ 8.79-8.77 (m, 2H), 7.41-7.05 (m, 5H), 6.21-6.03 (m, 1H), 5.27-5.21 (m, 1H), 4.10-4.07 (m, 1H), 3.93-3.64 (m, 14 H), 2.19-2.06 (m, 2H). |

TABLE 1-continued

| Example Number | Structure and Compound Name | LRMS m/z [M + H]+ | 1H NMR |
|---|---|---|---|
| 61 | 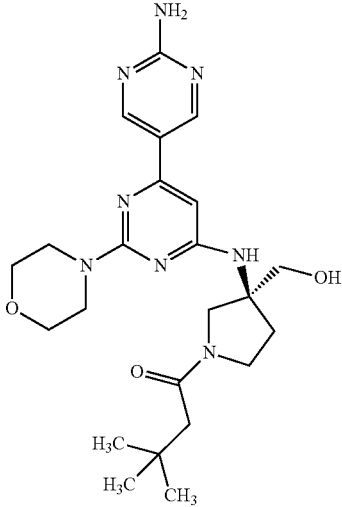 [SMILES: CC(C)(C)CC(=O)N1CC[C@](CO)(Nc2cc(-c3cnc(N)nc3)nc(N3CCOCC3)n2)C1]

1-[(3S)-3-{[2'-amino-2-(morpholin-4-yl)-4,5'-bipyrimidin-6-yl]amino}-3-(hydroxymethyl)pyrrolidin-1-yl]-3,3-dimethylbutan-1-one | 471.0 | 1H NMR (400 MHz, METHANOL-d4) δ 8.82 (s, 2H), 6.24 (d, J = 3.6 Hz, 1H), 4.27-4.00 (m, 2H), 3.91 (d, J = 11.6 Hz, 1H), 3.78-3.60 (m, 11H), 2.33-2.25 (m, 4H), 1.05 (d, J = 19.2 Hz, 9H). |
| 62 | 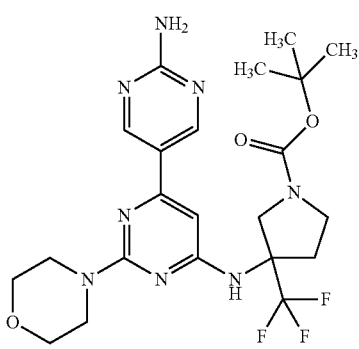 [SMILES: CC(C)(C)OC(=O)N1CCC(Nc2cc(-c3cnc(N)nc3)nc(N3CCOCC3)n2)(C(F)(F)F)C1]

tert-butyl 3-{[2'-amino-2-(morpholin-4-yl)-4,5'-bipyrimidin-6-yl]amino}-3-(trifluoromethyl)pyrrolidine-1-carboxylate | 511.2 | 1H NMR (400 MHz, CHLOROFORM-d) δ 8.96 (br s, 2H), 6.07 (s, 1H), 5.18 (br s, 2H), 4.61 (br s, 1H), 4.17 (d, J = 12.2 Hz, 1H), 3.97 (d, J = 12.3 Hz, 1H), 3.87-3.72 (m, 8H), 3.67-3.49 (m, 2H), 2.69 (br s, 1H), 2.55-2.40 (m, 1H), 1.49 (s, 9H). |
| 63 | 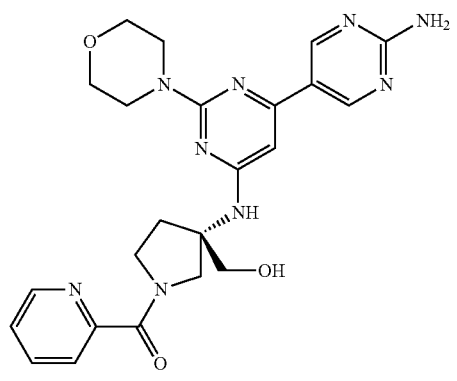 [SMILES: Nc1ncc(-c2cc(N[C@@]3(CO)CCN(C(=O)c4ccccn4)C3)nc(N3CCOCC3)n2)cn1]

[(3S)-3-{[2'-amino-2-(morpholin-4-yl)-4,5'-bipyrimidin-6-yl]amino}-3-(hydroxymethyl)pyrrolidin-1-yl](pyridin-2-yl)methanone | 478.1 | 1H NMR (400 MHz, DMSO-d6) δ 8.73-8.70 (m, 2H), 8.60-8.59 (m, 1H), 7.95-7.91 (m, 1H), 7.73-7.68 (m, 1H), 7.53-7.48 (m, 1H), 7.10-7.00 (m, 2H), 6.26-6.19 (m, 1H), 5.06-4.96 (m, 1H), 4.11-4.02 (m, 1H), 3.91-3.56 (m, 13H), 2.36-1.94 (m, 2H) |

TABLE 1-continued

| Example Number | Structure and Compound Name | LRMS m/z [M + H]+ | 1H NMR |
|---|---|---|---|
| 64 | 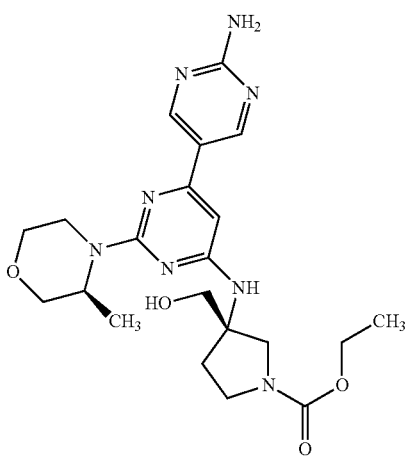 [SMILES: CCOC(=O)N1CC[C@](CO)(Nc2cc(-c3cnc(N)nc3)nc(N3CCOC[C@@H]3C)n2)C1]<br>ethyl (3S)-3-({2'-amino-2-[(3S)-3-methylmorpholin-4-yl]-4,5'-bipyrimidin-6-yl}amino)-3-(hydroxymethyl)pyrrolidine-1-carboxylate | 459.1 | 1H NMR (400 MHz, METHANOL-$d_4$): δ 8.80 (s, 2H), 6.22 (s, 1H), 4.35-4.19 (m, 1H), 4.12-3.31 (m, 12H), 3.23-3.20 (m, 2H), 2.34-2.20 (m, 2H), 1.29-1.12 (m, 6H). |
| 65 | 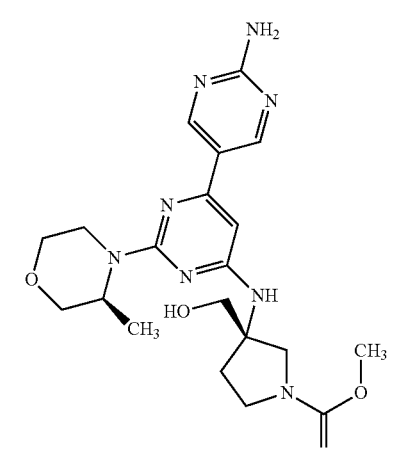<br>methyl (3S)-3-({2'-amino-2-[(3S)-3-methylmorpholin-4-yl]-4,5'-bipyrimidin-6-yl}amino)-3-(hydroxymethyl)pyrrolidine-1-carboxylate | 445.0 | 1H NMR (400 MHz, METHANOL-$d_4$) δ 8.80 (s, 2H), 6.22 (s, 1H), 4.34-4.30 (m, 1H), 4.02-3.52 (m, 13H), 3.21-3.19 (m, 2H), 2.34-2.31 (m, 1H), 2.24-2.16 (m, 1H), 1.29 (d, J = 6.8 Hz, 3H). |

TABLE 1-continued

| Example Number | Structure and Compound Name | LRMS m/z [M + H]+ | 1H NMR |
|---|---|---|---|
| 66 | 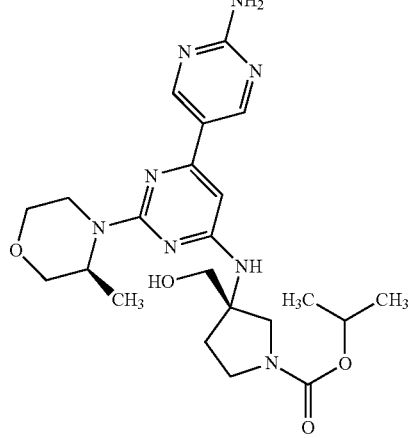<br>propan-2-yl (3S)-3-({2'-amino-2-[(3S)-3-methylmorpholin-4-yl]-4,5'-bipyrimidin-6-yl}amino)-3-(hydroxymethyl)pyrrolidine-1-carboxylate | 473.1 | 1H NMR (400 MHz, METHANOL-d4) δ 8,81 (s, 2H), 6.22 (s, 1H), 4.33-4.26 (m, 1H), 3.97-3.31 (m, 11H), 3.23-3.20 (m, 2H), 2.33-2.23 (m, 2H), 1.31-1.13 (m, 9H). |
| 67 | 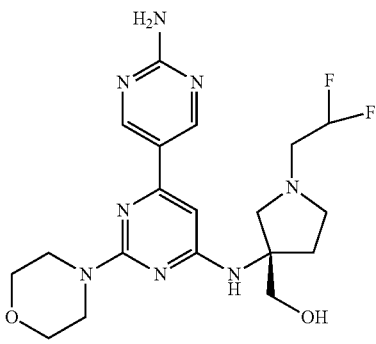 [SMILES: Nc1ncc(-c2cc(N[C@@]3(CO)CCN(CC(F)F)C3)nc(N3CCOCC3)n2)cn1]<br>[(3S)-3-{[2'-amino-2-(morpholin-4-yl)-4,5'-bipyrimidin-6-yl]amino}-1-(2,2-difluoroethyl)pyrrolidin-3-yl]methanol | 437.1 | 1H NMR (400 MHz, DMSO-d6) δ 8.72 (s, 2H), 6.98-6.92 (m, 2H), 6.29-6.20 (m, 1H), 6.09-6.06 (m, 1H), 4.87 (s, 1H), 3.76-3.59 (m, 10H), 3.50-3.42 (m, 1H), 2.91-2.77 (m, 4H), 2.72-2.64 (m, 2H), 2.04-1.96 (m, 2H). |
| 68 | 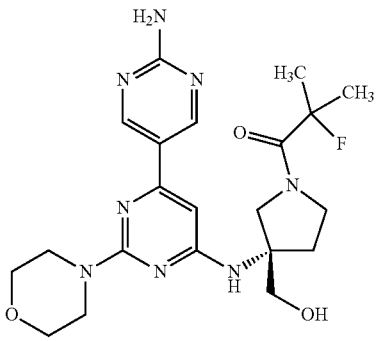 [SMILES: CC(C)(F)C(=O)N1CC[C@](CO)(Nc2cc(-c3cnc(N)nc3)nc(N3CCOCC3)n2)C1]<br>1-[(3S)-3-{[2'-amino-2-(morpholin-4-yl)-4,5'-bipyrimidin-6-yl]amino}-3-(hydroxymethyl)pyrrolidin-1-yl]-2-fluoro-2-methylpropan-1-one | 461.1 | 1H NMR (400 MHz, DMSO-d6 + D2O) δ 8.74 (s, 2H), 7.05-6.97 (m, 2H), 6.23 (s, 1H), 4.26-4.24 (m, 1H), 3.88-3.65 (m, 12H), 2.34-2.05 (m, 3H), 1.53-1.40 (m, 6H). |

TABLE 1-continued

| Example Number | Structure and Compound Name | LRMS m/z [M + H]+ | 1H NMR |
|---|---|---|---|
| 69 | 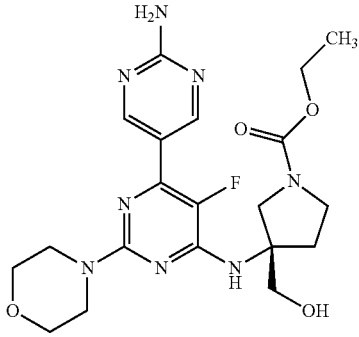 [SMILES: CCOC(=O)N1CC[C@](CO)(Nc2nc(N3CCOCC3)nc(-c3cnc(N)nc3)c2F)C1]<br>ethyl (3S)-3-{[2'-amino-5-fluoro-2-(morpholin-4-yl)-4,5'-bipyrimidin-6-yl]amino}-3-(hydroxymethyl)pyrrolidine-1-carboxylate | 463.1 | $^1$H NMR (400 MHz, DMSO-d$_6$) δ 8.76 (s, 2H), 7.17-6.94 (m, 3H), 4.99 (br s, 1H), 4.07-3.95 (m, 2H), 3.47-3.85 (m, 14H), 2.43-2.30 (m, 1H), 2.21-2.06 (m, 1H) 1.16 (t, J = 6.8 Hz, 3H). |
| 70 | 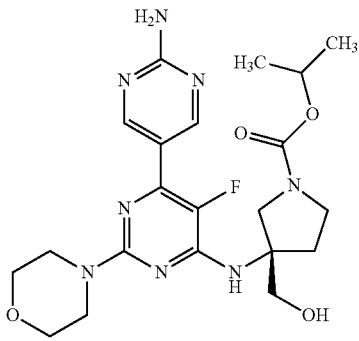 [SMILES: CC(C)OC(=O)N1CC[C@](CO)(Nc2nc(N3CCOCC3)nc(-c3cnc(N)nc3)c2F)C1]<br>propan-2-yl (3S)-3-{[2'-amino-5-fluoro-2-(morpholin-4-yl)-4,5'-bipyrimidin-6-yl]amino}-3-(hydroxymethyl)pyrrolidine-1-carboxylate | 477.1 | $^1$H NMR (400 MHz, DMSO-d$_6$) δ 8.76 (s, 2H), 7.19-6.93 (m, 3H), 4.99 (br s, 1H), 4.79-4.67 (m, 1H), 3.89-3.40 (m, 14H), 2.42-2.29 (m, 1H), 2.21-2.05 (m, 1H), 1.17 (d, J = 6.0 Hz, 6H). |
| 71 | 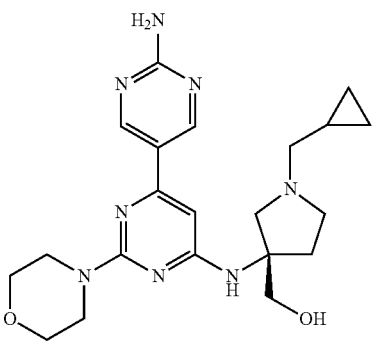 [SMILES: Nc1ncc(-c2cc(N[C@@]3(CO)CCN(CC4CC4)C3)nc(N3CCOCC3)n2)cn1]<br>[(3S)-3-{[2'-amino-2-(morpholin-4-yl)-4,5'-bipyrimidin-6-yl)amino}-1-(cyclopropylmethyl)pyrrolidin-3-yl]methanol | 427.2 | $^1$H NMR (400 MHz, CDCl$_3$) δ 8.83 (s, 2H), 6.05 (s, 1H), 5.28 (s, 2H), 5.10 (s, 1H), 3.92-3.78 (m, 11H), 2.98-2.95 (m, 1H), 2.90-2.84 (m, 2H), 2.67-2.65 (m, 1H), 2.36-2.34 (m, 2H), 2.22-2.21 (m, 1H), 2.09-2.08 (m, 1H), 0.90-0.89 (m, 1H), 0.54-0.50 (m, 2H), 0.15-0.13 (m, 2H) |

| Example Number | Structure and Compound Name | LRMS m/z [M + H]+ | 1H NMR |
|---|---|---|---|
| 72 | 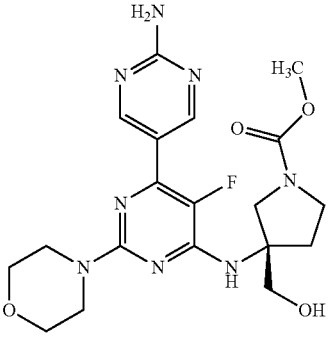 [SMILES: COC(=O)N1CC[C@](CO)(Nc2nc(N3CCOCC3)nc(-c3cnc(N)nc3)c2F)C1]<br>methyl (3S)-3-{[2'-amino-5-fluoro-2-(morpholin-4-yl)-4,5'-bipyrimidin-6-yl]amino}-3-(hydroxymethyl)pyrrolidine-1-carboxylate | 449.0 | $^1$H NMR (400 MHz, DMSO-d$_6$) δ 8.76 (s, 2H), 7.17-6.94 (m, 3H), 4.98 (s, 1H), 3.83-3.48 (m, 17H), 2.43-2.32 (m, 1H), 2.21-2.06 (m, 1H). |
| 73 | 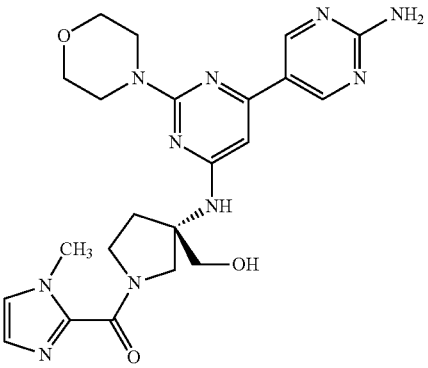 [SMILES: Cn1ccnc1C(=O)N1CC[C@](CO)(Nc2cc(-c3cnc(N)nc3)nc(N3CCOCC3)n2)C1]<br>[(3S)-3-{[2'-amino-2-(morpholin-4-yl)-4,5'-bipyrimidin-6-yl]amino}-3-(hydroxymethyl)pyrrolidin-1-yl](1-methyl-1H-imidazol-2-yl)methanone | 481.1 | $^1$H NMR (400 MHz, CDCl$_3$) δ 8.78 (d, J = 11.2 Hz, 2H), 7.12-6.95 (m, 2H), 5.98 (d, J = 12.8 Hz, 1H), 5.30-5.22 (m, 2H), 5.20-5.10 (m, 1H), 5.09-4.95 (m, 1H), 4.43 (s, 1H), 4.40-4.08 (m, 1H), 4.05-3.85 (m, 3H), 3.77-3.42 (m, 12H), 2.18-2.16 (m, 1H), 2.27-2.22 (m, 1H). |
| 74 | 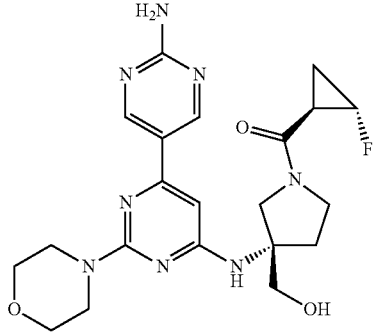 [SMILES: Nc1ncc(-c2cc(N[C@@]3(CO)CCN(C(=O)[C@H]4C[C@@H]4F)C3)nc(N3CCOCC3)n2)cn1]<br>[(3S)-3-{[2'-amino-2-(morpholin-4-yl)-4,5'-bipyrimidin-6-yl]amino}-3-(hydroxymethyl)pyrrolidin-1-yl][(1R,2S)-2-fluorocyclopropyl]methanone | 459.1 | $^1$H NMR (400 MHz, METHANOL-d$_4$) δ 8.83 (s, 2H), 6.26 (s, 1H), 4.38-4.25 (m, 1H), 4.03-3.87 (m, 4H), 3.77-3.71 (m, 6H), 3.65-3.57 (m, 2H), 2.51-2.22 (m, 4H), 1.45-1.25 (m, 3H) |

TABLE 1-continued

| Example Number | Structure and Compound Name | LRMS m/z [M + H]+ | 1H NMR |
|---|---|---|---|
| 75 | 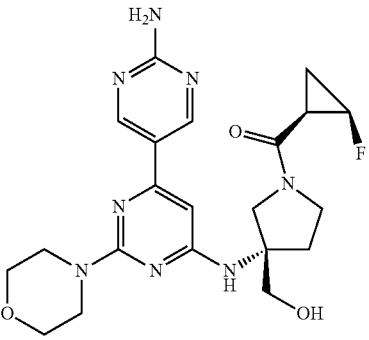 [SMILES: Nc1ncc(-c2cc(N[C@@]3(CO)CCN(C(=O)[C@H]4C[C@H]4F)C3)nc(N3CCOCC3)n2)cn1]<br>[(3S)-3-{[2'-amino-2-(morpholin-4-yl)-4,5'-bipyrimidin-6-yl]amino}-3-(hydroxymethyl)pyrrolidin-1-yl][(1R,2R)-2-fluorocyclopropyl]methanone | 459.1 | 1H NMR (400 MHz, METHANOL-$d_4$) δ 8.83 (s, 2H), 6.26 (s, 1H), 4.20-4.15 (m, 1H), 4.04-3.95 (m, 2H), 3.91-3.86 (m, 2H), 3.77-3.71 (m, 7H), 3.62-3.60 (m, 1H), 2.54-2.51 (m, 1H), 2.39-2.29 (m, 2H), 2.05-1.95 (m, 1H), 1.72-1.67 (m, 1H), 1.14-1.10 (m, 2H). |
| 76 | 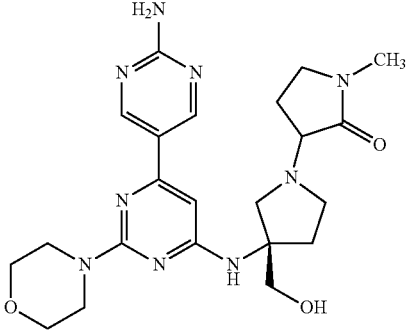 [SMILES: CN1CCC(N2CC[C@](CO)(Nc3cc(-c4cnc(N)nc4)nc(N4CCOCC4)n3)C2)C1=O]<br>(3S)-3-{[2'-amino-2-(morpholin-4-yl)-4,5'-bipyrimidin-6-yl]amino}-3-(hydroxymethyl)-1'-methyl-1,3'-bipyrrolidin-2'-one | 470.3 | 1H NMR (400 MHz, METHANOL-$d_4$) δ 8.82 (s, 2H), 6.27 (s, 1H), 3.97-3.95 (m, 1H), 3.89-3.87 (m, 1H), 3.80-3.72 (m, 8H), 3.41-3.33 (m, 4H), 3.06-2.95 (m, 2H), 2.86 (s, 3H), 2.80-2.75 (m, 1H), 2.26-2.03 (m, 4H). |
| 77 | 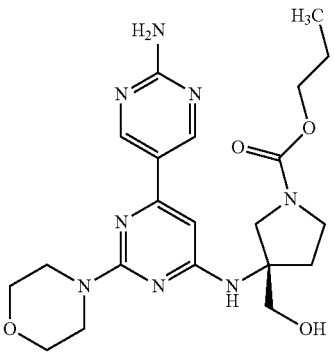 [SMILES: CCCOC(=O)N1CC[C@](CO)(Nc2cc(-c3cnc(N)nc3)nc(N3CCOCC3)n2)C1]<br>propyl (3S)-3-{[2'-amino-2-(morpholin-4-yl)-4,5'-bipyrimidin-6-yl]amino}-3-(hydroxymethyl)pyrrolidine-1-carboxylate | 459.2 | 1H NMR (400 MHz, METHANOL-$d_4$) δ 8.82 (s, 2H), 6.25 (s, 1H), 4.05-3.88 (m, 5H), 3.77-3.33 (m, 11H), 2.34-2.24 (m, 2H), 1.68-1.63 (m, 2H), 0.99-0.95 (m, 3H). |

TABLE 1-continued

| Example Number | Structure and Compound Name | LRMS m/z [M + H]+ | 1H NMR |
|---|---|---|---|
| 78 | 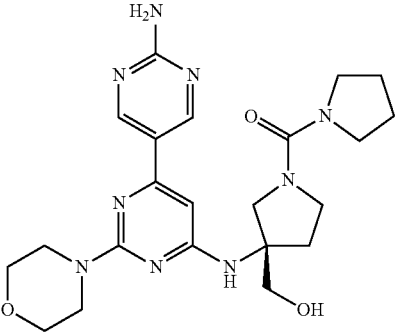 [SMILES: Nc1ncc(-c2cc(N[C@@]3(CO)CCN(C(=O)N4CCCC4)C3)nc(N3CCOCC3)n2)cn1]<br>[(3S)-3-{[2,-amino-2-(morpholin-4-yl)-4,5'-bipyrimidin-6-yl]amino}-3-(hydroxymethyl)pyrrolidin-1-yl](pyrrolidin-1-yl)methanone | 470.1 | 1H NMR (400 MHz, METHANOL-d4) δ 8.82 (s, 2H), 6.24 (s, 1H), 4.02-3.89 (m, 3H), 3.76-3.48 (m, 11H), 3.40-3.33 (m, 4H), 2.35-2.34 (m, 1H), 2.21-2.07 (m, 1H), 1.88-1.87 (m, 4H). |
| 79 | 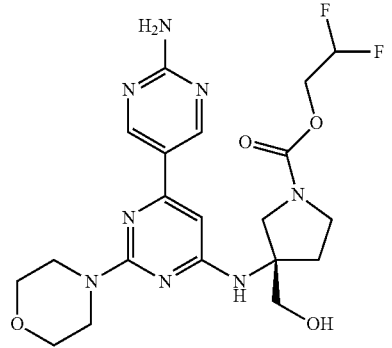 [SMILES: Nc1ncc(-c2cc(N[C@@]3(CO)CCN(C(=O)OCC(F)F)C3)nc(N3CCOCC3)n2)cn1]<br>2,2-difluoroethyl (3S)-3-{[2'-amino-2-(morpholin-4-yl)-4,5'-bipyrimidin-6-yl]amino}-3-(hydroxymethyl)pyrrolidine-1-carboxylate | 481.1 | 1H NMR (400 MHz, DMSO-d6 + D2O) δ 8.74 (s, 2H), 7.08-7.05 (m, 1H), 6.22 (s, 1H), 6.33-6.05 (t, J = 56 Hz, 1H), 4.29-4.22 (m, 2H), 3.81-3.71 (m, 4H), 3.64-3.54 (m, 8H), 3.42-3.41 (m, 2H), 2.22-2.11 (m, 2H). |
| 80 | 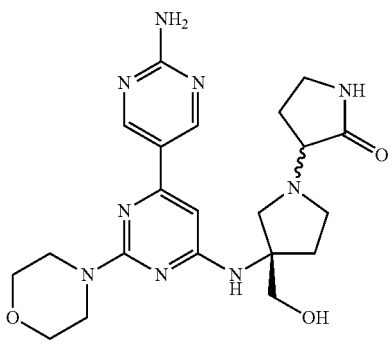 [SMILES: Nc1ncc(-c2cc(N[C@@]3(CO)CCN(C4CCNC4=O)C3)nc(N3CCOCC3)n2)cn1]<br>(3S)-3-{[2'-amino-2-(morpholin-4-yl)-4,5'-bipyrimidin-6-yl]amino}-3-(hydroxymethyl)-1,3'-bipyrrolidin-2'-one | 456.1 | 1H NMR (400 MHz, METHANOL-d4) δ 8.83 (s, 2H), 6.27 (s, 1H), 4.01-3.98 (m, 1H), 3.89-3.87 (m, 1H), 3.80-3.72 (m, 8H), 3.40-3.30 (m, 4H), 3.06-2.95 (m, 2H), 2.86-2.82 (m, 1H), 2.31-2.25 (m, 1H), 2.15-2.13 (m, 3H). |

TABLE 1-continued

| Example Number | Structure and Compound Name | LRMS m/z [M + H]+ | 1H NMR |
|---|---|---|---|
| 81 | 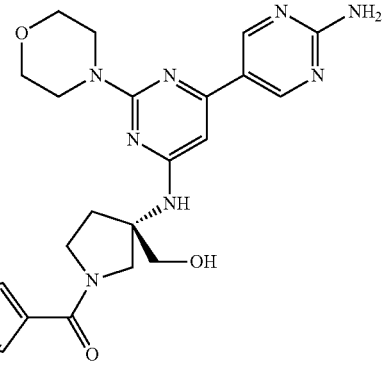<br>[(3S)-3-{[2'-amino-2-(morpholin-4-yl)-4,5'-bipyrimidin-6-yl]amino}-3-(hydroxymethyl)pyrrolidin-1-yl](1-methyl-1H-pyrazol-4-yl)methanone | 481.2 | 1H NMR (400 MHz, METHANOL-d4) δ 8.78 (d, J = 4.8 Hz, 2H), 8.11-8.00 (m, 1H), 7.89-7.79 (m, 1H), 6.22 (d, J = 10.4 Hz, 1H), 4.47-4.18 (m, 17H), 2.60-2.15 (m, 2H) |
| 82 | 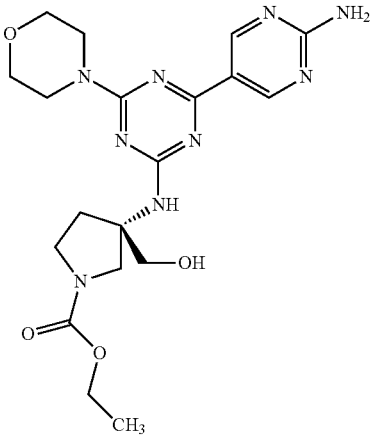 [SMILES: CCOC(=O)N1CC[C@](CO)(Nc2nc(-c3cnc(N)nc3)nc(N3CCOCC3)n2)C1]<br>ethyl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate | 446.3 | 1H NMR (400 MHz, DMSO-d6) δ 8.99 (s, 2H), 7.36-7.23 (m, 3H), 4.96 (br s, 1H), 4.02-4.00 (m, 2H), 3.98-3.51 (m, 12H), 3.49-3.43 (m, 2H), 2.32-2.25 (m, 1H), 2.11-2.10 (m, 1H), 1.16 (t, J = 5.2 Hz, 3H). |
| 83 | 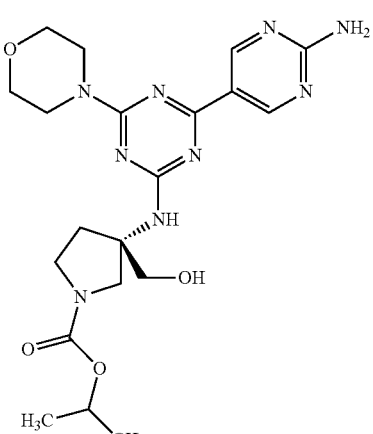<br>propan-2-yl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate | 460.0 | 1H NMR (400 MHz, METHANOL-d4) δ 9.08 (s, 2H), 4.01-3.56 (m, 12H), 3.54-3.50 (m, 3H), 2.35-2.34 (m, 1H), 2.22-2.21 (m, 1H), 1.35-1.24 (m, 6H). |

| Example Number | Structure and Compound Name | LRMS m/z [M + H]+ | ¹H NMR |
|---|---|---|---|
| 84 | 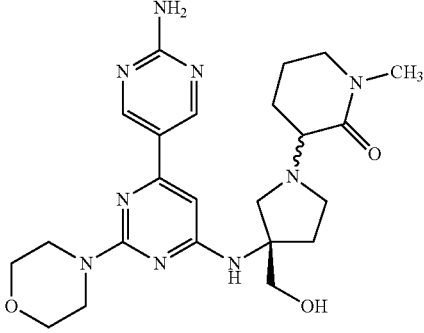 [SMILES: CN1CCCC(N2CC[C@](CO)(Nc3cc(-c4cnc(N)nc4)nc(N4CCOCC4)n3)C2)C1=O]<br>3-[(3S)-3-{[2'-amino-2-{morpholin-4-yl)-4,5'-bipyrimidin-6-yl]amino}-3-(hydroxymethyl)pyrrolidin-1-yl]-1-methylpiperidin-2-one | 484.1 | ¹H NMR (400 MHz, METHANOL-d₄) δ 8.83 (s, 2H), 6.28 (s, 1H), 3.95-3.88 (m, 2H), 3.80-3.72 (m, 8H), 3.41-3.33 (m, 2H), 3.22-3.18 (m, 3H), 3.08-2.85 (m, 3H), 2.93 (s, 3H), 2.14-1.82 (m, 5H). |
| 85 | 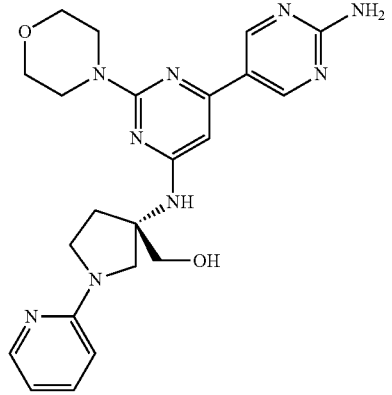 [SMILES: Nc1ncc(-c2cc(N[C@@]3(CO)CCN(c4ccccn4)C3)nc(N3CCOCC3)n2)cn1]<br>[(3S)-3-{[2'-amino-2-(morpholin-4-yl)-4,5'-bipyrimidin-6-yl]amino}-1-(pyridin-2-yl)pyrrolidin-3-yl]methanol | 450.1 | ¹H NMR (400 MHz, DMSO-d₆) δ 8.70 (s, 2H), 8.04-8.03 (m, 1H), 7.48-7.44 (m, 1H), 7.04-6.99 (m, 3H), 6.53-6.50 (m, 1H), 6.39-6.37 (m, 1H), 6.24 (s, 1H), 5.00-4.97 (m, 1H), 3.82-3.80 (m, 3H), 3.72-3.62 (m, 7H), 3.60-3.57 (m, 1H), 3.52-3.40 (m, 2H), 3.17-3.16 (m, 1H), 2.49-2.38 (m, 1H), 2.39-2.20 (m, 1H). |
| 86 | 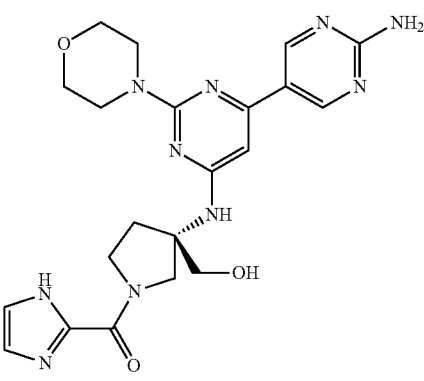 [SMILES: Nc1ncc(-c2cc(N[C@@]3(CO)CCN(C(=O)c4ncc[nH]4)C3)nc(N3CCOCC3)n2)cn1]<br>[(3S)-3-{[2'-amino-2-(morpholin-4-yl)-4,5'-bipyrimidin-6-yl]amino}-3-(hydroxymethyl)pyrrolidin-1-yl](1H-imidazol-2-yl)methanone | 467.1 | ¹H NMR (400 MHz, METHANOL-d₄) δ 8.80-8.79 (m, 2H), 7.19 (s, 2H), 6.24-6.21 (m, 1H), 4.37-4.34 (m, 1H), 4.25-4.20 (m, 1H), 4.06-3.95 (m, 2H), 3.89-3.73 (m, 10H), 2.49-2.26 (m, 2H) |

TABLE 1-continued

| Example Number | Structure and Compound Name | LRMS m/z [M + H]⁺ | ¹H NMR |
|---|---|---|---|
| 87 | 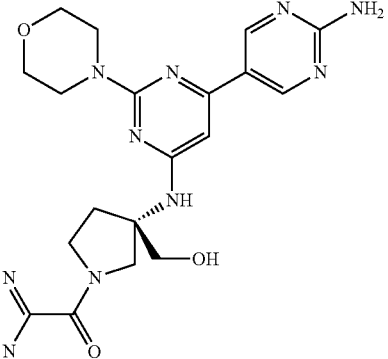[(3S)-3-{[2'-amino-2-(morpholin-4-yl)-4,5'-bipyrimidin-6-yl]amino}-3-(hydroxymethyl)pyrrolidin-1-yl](pyrimidin-2-yl)methanone | 479.1 | ¹H NMR (400 MHz, DMSO-d₆) δ 8.91 (d, J = 5.2 Hz, 2H), 8.72 (d, J = 14.8 Hz, 2H), 7.64-7.60 (m, 1H), 7.11-7.01 (m, 3H), 6.27-6.19 (m, 1H), 5.07-4.97 (m, 1H), 4.07-3.67 (m, 2H), 3.63-3.50 (m, 12H), 2.33-2.13 (m, 2H). |
| 88 | 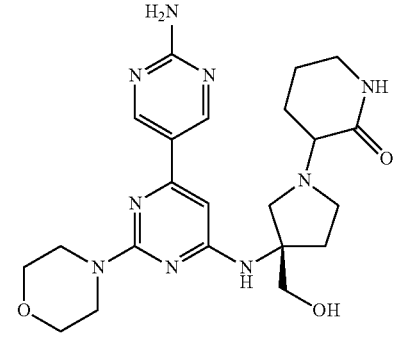 [SMILES: Nc1ncc(-c2cc(N[C@@]3(CO)CCN(C4CCCNC4=O)C3)nc(N3CCOCC3)n2)cn1]3-[(3S)-3-{[2'-amino-2-(morpholin-4-yl)-4,5'-bipyrimidin-6-yl]amino}-3-(hydroxymethyl)pyrrolidin-1-yl]piperidin-2-one | 492.2 | ¹H NMR (400 MHz, METHANOL-d₄) δ 8.81 (s, 2H), 6.24 (s, 1H), 4.10-4.01 (m, 3H), 3.99-3.88 (m, 1H), 3.74-3.61 (m, 9H), 3.49-3.41 (m, 3H), 3.28-3.27 (m, 1H), 2.41-2.31 (m, 3H), 2.30-1.85 (m, 3H). |
| 89 | 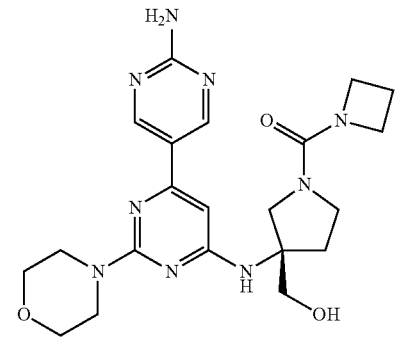 [SMILES: Nc1ncc(-c2cc(N[C@@]3(CO)CCN(C(=O)N4CCC4)C3)nc(N3CCOCC3)n2)cn1][(3S)-3-{[2'-amino-2-(morpholin-4-yl)-4,5'-bipyrimidin-6-yl]amino}-3-(hydroxymethyl)pyrrolidin-1-yl](azetidin-1-yl)methanone | 456.0 | ¹H NMR (400 MHz, METHANOL-d₄) δ 8.80 (s, 2H), 6.22 (s, 1H), 4.05-4.02 (m, 5H), 4.00-3.97 (m, 2H), 3.87-3.75 (m, 8H), 3.60-3.51 (m, 1H), 3.49-3.46 (m, 2H), 2.31-2.16 (m, 4H). |

TABLE 1-continued

| Example Number | Structure and Compound Name | LRMS m/z [M + H]+ | 1H NMR |
|---|---|---|---|
| 90 | 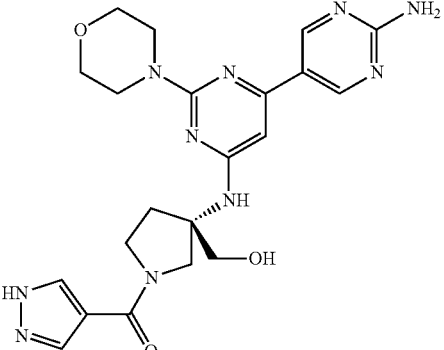<br>[(3S)-3-{[2'-amino-2-(morpholin-4-yl)-4,5'-bipyrimidin-6-yl]amino}-3-(hydroxymethyl)pyrrolidin-1-yl](1H-pyrazol-4-yl)methanone | 467.0 | 1H NMR (400 MHz, DMSO-d6) δ 8.72-8.71 (m, 2H), 8.22-7.80 (m, 3H), 7.08-7.00 (m, 3H), 6.25-6.21 (m, 1H), 4.98 (br s, 1H), 4.20-4.18 (m, 1H), 3.91-3.88 (m, 1H), 3.82-3.55 (m, 12H), 2.25-2.15 (m, 2H) |
| 91 | 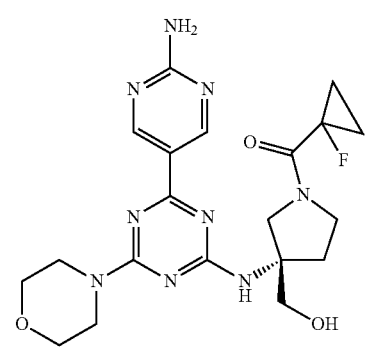 [SMILES: Nc1ncc(-c2nc(N[C@@]3(CO)CCN(C(=O)C4(F)CC4)C3)nc(N3CCOCC3)n2)cn1]<br>[(3S)-3-{[4-(2-aminopyrimidin-5-yl)-6-(morpholin-4-yl)-1,3,5-triazin-2-yl]amino}-3-(hydroxymethyl)pyrrolidin-1-yl](1-fluorocyclopropyl)methanone | 460.0 | 1H NMR (400 MHz, DMSO-d6) δ 9.01-8.99 (m, 2H), 7.45-7.24 (m, 3H), 5.06-5.02 (m, 1H), 4.30-4.27 (m, 1H), 3.95-3.48 (m, 13H), 2.39-2.06 (m, 2H), 1.27-1.08 (m, 4H) |
| 92 | 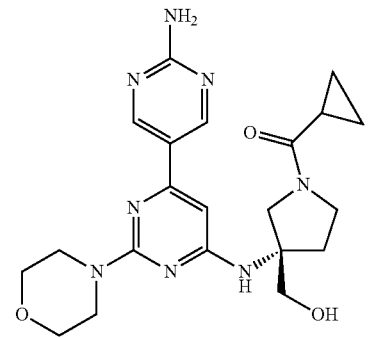 [SMILES: Nc1ncc(-c2cc(N[C@@]3(CO)CCN(C(=O)C4CC4)C3)nc(N3CCOCC3)n2)cn1]<br>[(3S)-3-{[2'-amino-2-(morpholin-4-yl)-4,5'-bipyrimidin-6-yl]amino}-3-(hydroxymethyl)pyrrolidin-1-yl](cyclopropyl)methanone | 441.2 | 1H NMR (400 MHz, DMSO) δ 8.72 (s, 2H), 7.09-7.03 (m, 3H), 6.24 (s, 1H), 5.04-4.98 (m, 1H), 3.79-3.75 (m, 3H), 3.75-3.60 (m, 9H), 3.59-3.42 (m, 2H), 2.50-2.01 (m, 2H), 1.29-1.24 (m, 1H), 0.71-0.69 (m, 4H). |

TABLE 1-continued

| Example Number | Structure and Compound Name | LRMS m/z [M + H]+ | 1H NMR |
|---|---|---|---|
| 93 | 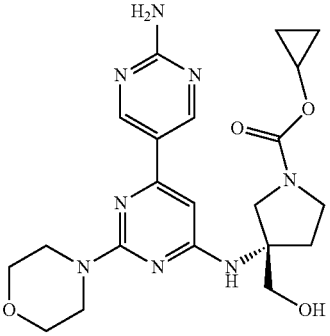 [SMILES: Nc1ncc(-c2cc(N[C@@]3(CO)CCN(C(=O)OC4CC4)C3)nc(N3CCOCC3)n2)cn1]<br>cyclopropyl (3S)-3-{[2'-amino-2-(morpholin-4-yl)-4,5'-bipyrimidin-6-yl]amino}-3-(hydroxymethyl)pyrrolidine-1-carboxylate | 457.3 | 1H NMR (400 MHz, DMSO-d6) δ 8.71 (s, 2H), 7.02-7.01 (m, 3H), 6.22-6.21 (m, 1H), 4.99-4.85 (br s, 1H), 3.95-3.94 (m, 1H), 3.74-3.65 (m, 11H), 3.43-3.41 (m, 3H), 2.32-2.30 (m, 1H), 2.21-2.07 (m, 1H), 0.62-0.55 (m, 4H). |
| 94 | 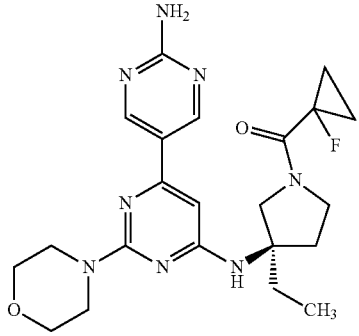 [SMILES: CC[C@@]1(Nc2cc(-c3cnc(N)nc3)nc(N3CCOCC3)n2)CCN(C(=O)C2(F)CC2)C1]<br>[(3R)-3-{[2'-amino-2-(morpholin-4-yl)-4,5'-bipyrimidin-6-yl]amino}-3-ethylpyrrolidin-1-yl](1-fluorocyclopropyl)methanone | 457.0 | 1H NMR (400 MHz, CDCl3) δ 8.86 (s, 2H), 6.01 (d, J = 5.2 Hz, 1H), 5.22 (br s, 2H), 4.50-4.43 (m, 1H), 3.97-3.88 (m, 1H), 3.87-3.73 (m, 9H), 3.72-3.65 (m, 1H), 3.55-3.48 (m, 1H), 2.36-2.14 (m, 2H), 2.08-1.87 (m, 2H), 1.46-1.32 (m, 2H) 1.25-1.15 (m, 2H), 0.95-0.89 (m, 3H). |
| 95 | 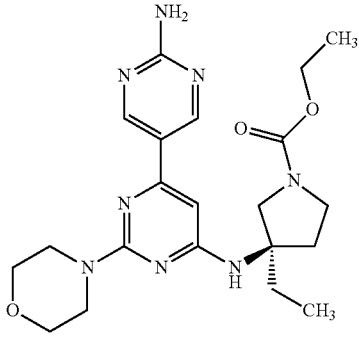 [SMILES: CCOC(=O)N1CC[C@@](CC)(Nc2cc(-c3cnc(N)nc3)nc(N3CCOCC3)n2)C1]<br>ethyl (3R)-3-{[2]-amino-2-(morpholin-4-yl)-4,5]-bipyrimidin-6-yl]amino}-3-ethylpyrrolidine-1-carboxylate | 443.0 | 1H NMR (400 MHz, CDCl3) δ 8.85 (s, 2H), 6.00 (s, 1H), 5.26 (br s, 2H), 4.51 (br s, 1H), 4.20-4.08 (m, 2H), 3.87-3.72 (m, 9H), 3.58-3.35 (m, 3H), 2.61-2.35 (m, 1H), 2.26-1.85 (m, 3H), 1.27-1.17 (m, 3H), 0.89 (t, J = 6.8 Hz, 3H). |

TABLE 1-continued

| Example Number | Structure and Compound Name | LRMS m/z [M + H]+ | 1H NMR |
|---|---|---|---|
| 96 | 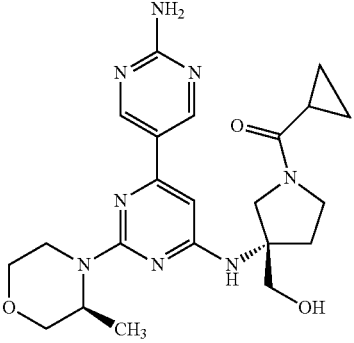 [SMILES: C[C@H]1COCCN1c1nc(N[C@@]2(CO)CCN(C(=O)C3CC3)C2)cc(-c2cnc(N)nc2)n1]<br>[(3S)-3-({2'-amino-2-[(3S)-3-methylmorpholin-4-yl]-4,5'-bipyrimidin-6-yl}amino)-3-(hydroxymethyl)pyrrolidin-1-yl](cyclopropyl)methanone | 477.3 | 1H NMR (400 MHz, METHANOL-$d_4$) δ 8.82 (s, 2H), 6.25 (d, J = 4.4 Hz, 1H), 4.69-4.67 (m, 1H), 4.34-4.31 (m, 2H), 4.05-3.58 (m, 9H), 3.34-3.21 (m, 1H), 2.52-2.22 (m, 2H), 1.83-1.75 (m, 1H), 1.30 (t, J = 6.4 Hz, 3H), 0.92-0.82 (m, 4H). |
| 97 | 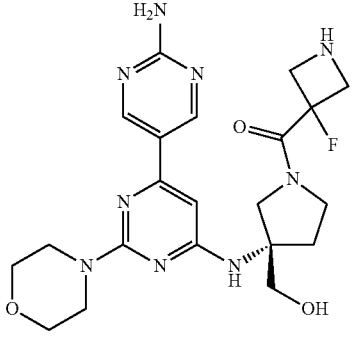 [SMILES: Nc1ncc(-c2cc(N[C@@]3(CO)CCN(C(=O)C4(F)CNC4)C3)nc(N3CCOCC3)n2)cn1]<br>[(3S)-3-{[2'-amino-2-(morpholin-4-yl)-4,5'-bipyrimidin-6-yl]amino}-3-(hydroxymethyl)pyrrolidin-1-yl](3-fluoroazetidin-3-yl)methanone | 474.0 | 1H NMR (400 MHz, METHANOL-$d_4$) δ 8.80 (s, 2H), 6.22 (s, 1H), 4.32-3.72 (m, 5H), 3.70-3.65 (m, 12H), 3.62-3.52 (m, 1H), 2.30-2.06 (m, 2H). |
| 98 | 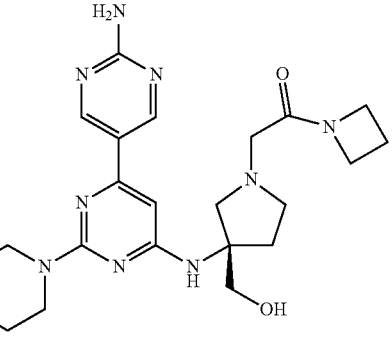<br>2-[(3S)-3-{[2'-amino-2-(morpholin-4-yl)-4,5'-bipyrimidin-6-yl]amino}-3-(hydroxymethyl)pyrrolidin-1-yl]-1-(azetidin-1-yl)ethanone | 470.2 | 1H NMR (400 MHz, METHANOL-$d_4$) δ 8.80 (s, 2H), 6.24 (s, 1H), 4.32-4.26 (m, 2H), 4.07-3.87 (m, 4H), 3.79-3.70 (m, 8H), 3.25-3.10 (m, 2H), 3.02-2.90 (m, 2H), 2.80-2.70 (m, 2H), 2.35-2.25 (m, 2H), 2.18-2.10 (m, 2H). |

TABLE 1-continued

| Example Number | Structure and Compound Name | LRMS m/z [M + H]+ | 1H NMR |
|---|---|---|---|
| 99 | 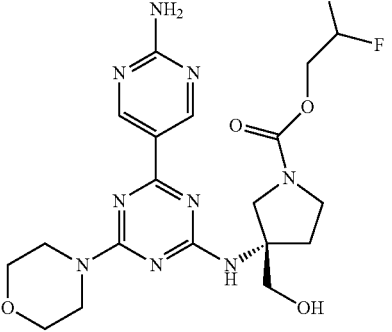<br>2,2-difluoroethyl (3S)-3-{[4-(2-aminopyrimidin-5-yl)-6-(morpholin-4-yl)-1,3,5-triazin-2-yl]amino}-3-(hydroxymethyl)pyrrolidine-1-carboxylate | 482.2 | 1H NMR (400 MHz, DMSO-d6) δ 9.01 (s, 2H), 7.42-7.25 (m, 3H), 6.36-6.09 (m, 1H), 5.05-4.99 (m, 1H), 4.31-4.23 (m, 2H), 3.83-3.40 (m, 14H), 2.33-2.29 (m, 1H), 2.14-2.11 (m, 1H) |
| 100 | 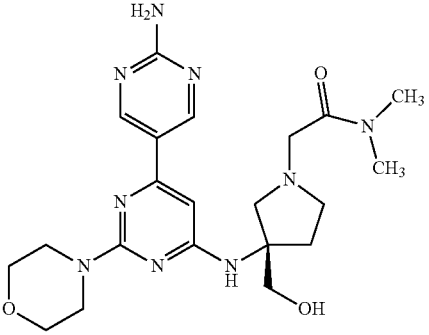 [SMILES: CN(C)C(=O)CN1CC[C@](CO)(Nc2cc(-c3cnc(N)nc3)nc(N3CCOCC3)n2)C1]<br>2-[(3S)-3-{[2'-amino-2-(morpholin-4-yl)-4,5'-bipyrimidin-6-yl]amino}-3-(hydroxymethyl)pyrrolidin-1-yl]-N,N-dimethylacetamide | 458 | 1H NMR (400 MHz, METHANOL-d4) δ 8.81 (s, 2H), 6.25 (s, 1H), 4.24 (s, 2H) 4.09-3.95 (m, 2H) 3.92-3.85 (m, 1H) 3.79-3.68 (m, 9H) 3.60-3.45 (m, 2H) 3.02-2.95 (m, 6H) 2.55-2.43 (m, 1H) 2.42-2.30 (m, 1H). |
| 101 | 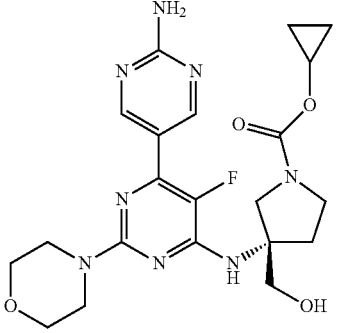<br>cyclopropyl (3S)-3-{[2'-amino-5-fluoro-2-(morpholin-4-yl)-4,5'-bipyrimidin-6-yl]amino}-3-(hydroxymethyl)pyrrolidine-1-carboxylate | 475.3 | 1H NMR (400 MHz, DMSO-d6) δ 8.76 (s, 2H), 7.13 (s, 2H), 6.99 (s, 1H), 4.99 (m, 1H), 3.95-3.80 (m, 1H), 3.78-3.34 (m, 14H), 2.36-2.33 (m, 1H), 2.16-2.14 (m, 1H), 0.63-0.55 (m, 4H). |

TABLE 1-continued

| Example Number | Structure and Compound Name | LRMS m/z [M + H]+ | 1H NMR |
|---|---|---|---|
| 102 | 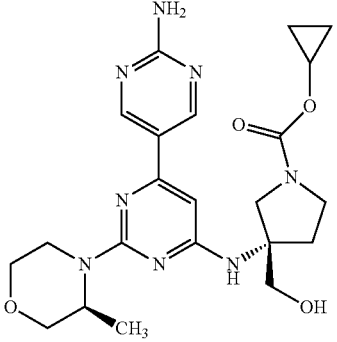 [SMILES: C[C@H]1COCCN1c1nc(N[C@@]2(CO)CCN(C(=O)OC3CC3)C2)cc(-c2cnc(N)nc2)n1]<br>cyclopropyl (3S)-3-({2'-amino-2-[(3S)-3-methylmorpholin-4-yl]-4,5'-bipyrimidin-6-yl}amino)-3-(hydroxymethyl)pyrrolidine-1-carboxylate | 471.3 | 1H NMR (400 MHz, METHANOL-d4) δ 8.80 (s, 2H), 6.21 (s, 1H), 4.61-4.60 (m, 1H), 4.33-4.30 (m, 1H), 4.01-3.31 (m, 11H), 3.25-3.22 (m, 1H), 2.33-2.20 (m, 2H), 1.30-1.27 (m, 3H), 0.68-0.62 (m, 4H). |
| 103 | 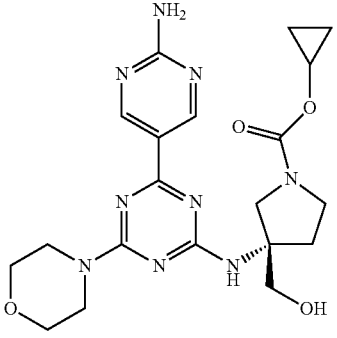 [SMILES: Nc1ncc(-c2nc(N[C@@]3(CO)CCN(C(=O)OC4CC4)C3)nc(N3CCOCC3)n2)cn1]<br>cyclopropyl (3S)-3-{[4-{2-aminopyrimidin-5-yl)-6-(morpholin-4-yl)-1,3,5-triazin-2-yl]amino}-3-(hydroxymethyl)pyrrolidine-1-carboxylate | 480.0 [M + 23]+ | 1H NMR (400 MHz, DMSO-d6) δ 9.00 (s, 2H), 7.36-7.24 (m, 3H), 5.01-4.95 (m, 1H), 3.94-3.17 (m, 15H), 2 33-2.28 (m, 1H), 2.10-2.09 (m, 1H), 0.61-0.55 (m, 4H). |
| 104 | 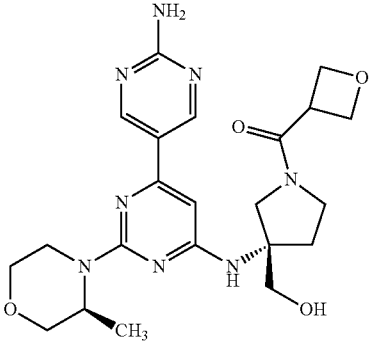 [SMILES: C[C@H]1COCCN1c1nc(N[C@@]2(CO)CCN(C(=O)C3COC3)C2)cc(-c2cnc(N)nc2)n1]<br>[(3S)-3-({2'-amino-2-[(3S)-3-methylmorpholin-4-yl]-4,5'-bipyrimidin-6-yl}amino)-3-(hydroxymethyl)pyrrolidin-1-yl](oxetan-3-yl)methanone | 471.0 | 1H NMR (400 MHz, METHANOL-d4) δ 8.81 (s, 2H), 6.23 (s, 1H), 4.86-4.70 (m, 5H), 4.40-4.31 (m, 1H), 4.25-3.75 (m, 6H), 3.74-3.55 (m, 5H), 3.26-3.21 (m, 1H), 2.43-2.19 (m, 2H), 1.33 (t, J = 7.4 Hz, 3H). |

TABLE 1-continued

| Example Number | Structure and Compound Name | LRMS m/z [M + H]⁺ | ¹H NMR |
|---|---|---|---|
| 105 | 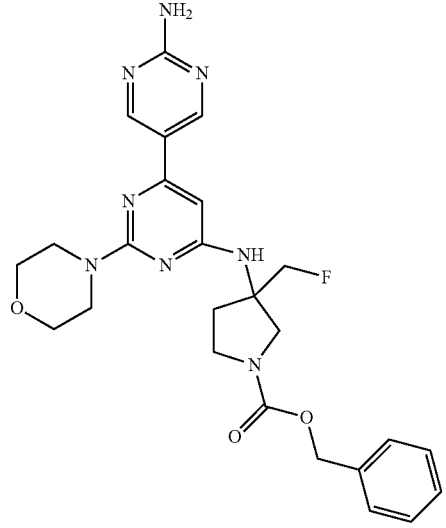 [SMILES: Nc1ncc(-c2cc(NC3(CF)CCN(C(=O)OCc4ccccc4)C3)nc(N3CCOCC3)n2)cn1]benzyl 3-{[2'-amino-2-(morpholin-4-yl)-4,5'-bipyrimidin-6-yl]amino}-3-(fluoromethyl)pyrrolidine-1-carboxylate | 508.9 | $^1$H NMR (700 MHz, DMSO-d$_6$) δ 8.74 (dd, J = 6.4, 3.7 Hz, 2H), 7.24-7.40 (m, 6H), 7.01 (br s, 2H), 6.23 (br s, 1H), 5.06 (br s, 2H) 4.67-4.91 (m, 2H), 3.76-3.95 (m, 1H), 3.56-3.71 (m, 8H), 3.33-3.56 (m, 1H), 2.28-2.40 (m, 1H), 2.14 (br s, 1H). |
| 106 | 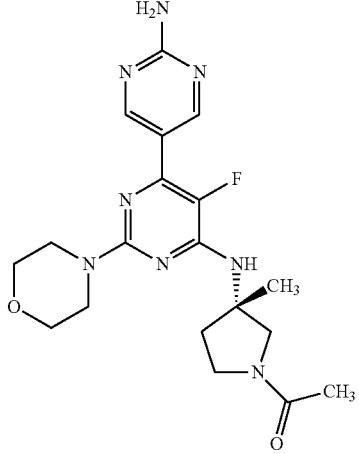 [SMILES: CC(=O)N1CC[C@](C)(Nc2nc(N3CCOCC3)nc(-c3cnc(N)nc3)c2F)C1]1-[(3S)-3-{[2'-amino-5-fluoro-2-(morpholin-4-yl)-4,5'-bipyrimidin-6-yl]amino}-3-methylpyrrolidin-1-yl]ethanone | 432.9 | $^1$H NMR (400 MHz, METHANOL-d$_4$) δ 8.88 (s, 2H), 4.01 (d, J = 11.0 Hz, 1H), 3.80-3.70 (m, 11H), 3.61-3.48 (m, 3H), 2.58-2.47 (m, 1H), 2.14-2.02 (m, 1H), 1.63 (s, 3H). |

TABLE 1-continued

| Example Number | Structure and Compound Name | LRMS m/z [M + H]+ | 1H NMR |
|---|---|---|---|
| 107 | 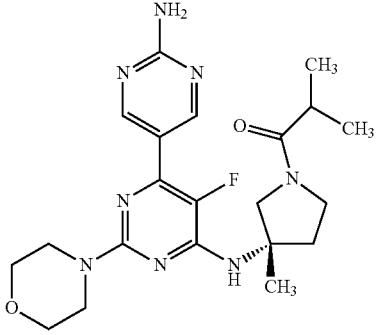 [SMILES: CC(C)C(=O)N1CC[C@](C)(Nc2nc(N3CCOCC3)nc(-c3cnc(N)nc3)c2F)C1]

1-[(3S)-3-{[2'-amino-5-fluoro-2-(morpholin-4-yl)-4,5'-bipyrimidin-6-yl]amino}-3-methylpyrrolidin-1-yl]-2-methylpropan-1-one | 445.1 | 1H NMR (400 MHz, CDCl3) δ 8.94 (d, J = 2.5 Hz, 2H), 5.27 (d, J = 3.3 Hz, 2H), 4.94 (dd, J = 2.8, 18.3 Hz, 1H), 4.15-3.90 (m, 1H), 3.83-3.53 (m, 11H), 2.79-2.32 (m, 2H), 2.13-1.95 (m, 1H), 1.64 (d, J = 5.8 Hz, 3H), 1.18-1.07 (m, 6H). |
| 108 | 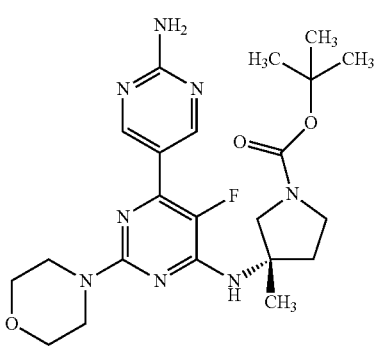 [SMILES: CC(C)(C)OC(=O)N1CC[C@](C)(Nc2nc(N3CCOCC3)nc(-c3cnc(N)nc3)c2F)C1]

tert-butyl (3S)-3-{[2'-amino-5-fluoro-2-(morpholin-4-yl)-4,5'-bipyrimidin-6-yl]amino}-3-methylpyrrolidine-1-carboxylate | 475.1 | 1H NMR (400 MHz, CDCl3) δ 8.94 (s, 2H), 5.32 (s, 2H), 4.98 (br s, 1H), 3.85-3.68 (m, 9H), 3.56-3.43 (m, 3H), 2.57-2.39 (m, 1H), 1.98 (td, J = 12.8, 7.5 Hz, 1H), 1.60 (s, 3H), 1.47 (d, J = 3.3 Hz, 9H). |
| 109 | 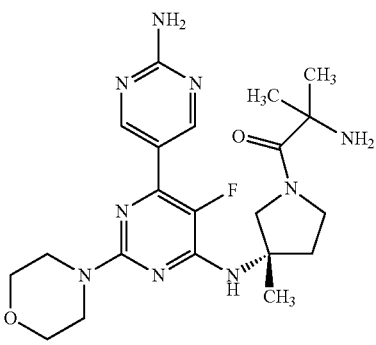 [SMILES: CC(C)(N)C(=O)N1CC[C@](C)(Nc2nc(N3CCOCC3)nc(-c3cnc(N)nc3)c2F)C1]

2-amino-1-[(3S)-3-{[2'-amino-5-fluoro-2-(morpholin-4-yl)-4,5'-bipyrimidin-6-yl]amino}-3-methylpyrrolidin-1-yl]-2-methylpropan-1-one | 460.0 | 1H NMR (400 MHz, METHANOL-d4) δ 8.89 (s, 2H), 4.76-4.29 (m, 1H), 3.94-3.57 (m, 11H), 2.74-2.38 (m, 1H), 2.24-1.98 (m, 1H), 1.71-1.44 (m, 9H) |

TABLE 1-continued

| Example Number | Structure and Compound Name | LRMS m/z [M + H]+ | 1H NMR |
|---|---|---|---|
| 110 | 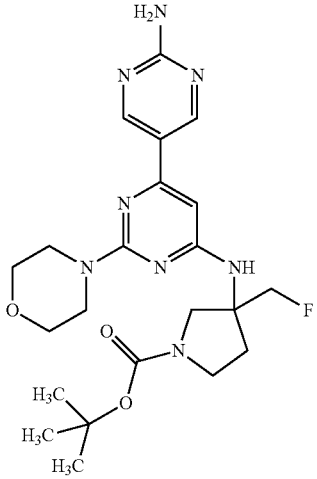 [SMILES: CC(C)(C)OC(=O)N1CCC(CF)(Nc2cc(-c3cnc(N)nc3)nc(N3CCOCC3)n2)C1]<br>tert-butyl 3-{[2'-amino-2-(morpholin-4-yl)-4,5'-bipyrimidin-6-yl]amino}-3-(fluoromethyl)pyrrolidine-1-carboxylate | 474.95 | 1H NMR (700 MHz, DMSO-d6) δ 8.74 (s, 2H), 7.32-7.23 (m, 1H), 6.98 (br s, 2H), 6.23 (br s, 1H), 4.90-4.61 (m, 2H), 3.78-3.69 (m, 1H), 3.64 (br s, 3H), 3.52 (s, 1H), 3.43-3.30 (m, 2H), 2.31-2.20 (m, 1H), 2.10 (d, J = 5.9 Hz, 1H), 1.63-1.29 (m, 12H). |
| 111 | 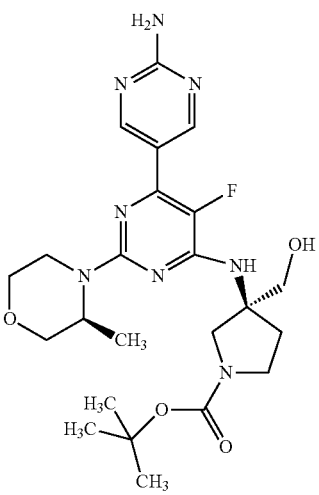 [SMILES: C[C@H]1COCCN1c1nc(N[C@@]2(CO)CCN(C(=O)OC(C)(C)C)C2)c(F)c(-c2cnc(N)nc2)n1]<br>tert-butyl (3S)-3-({2'-amino-5-fluoro-2-[(3S)-3-methylmorpholin-4-yl]-4,5'-bipyrimidin-6-yl}amino)-3-(hydroxymethyl)pyrrolidine--carboxylate | 527.0 [M + 23]+ | 1H NMR (400 MHz, CDCl3) δ 8.93 (s, 2H), 5.35 (s, 2H), 5.11 (s, 1H) 4.55-4.49 (m, 1H) 4.20-3.90 (m, 3H) 3.85-3.80 (m, 1H) 3.80-3.65 (m, 4H) 3.60-3.45 (m, 3H) 3.30-3.20 (m, 1H) 2.30-2.20 (m, 2H) 1.70 (br s, 1H), 1.60 (s, 9H), 1.28 (d, J = 6.8 Hz, 3H). |

TABLE 1-continued
| Example Number | Structure and Compound Name | LRMS m/z [M + H]+ | 1H NMR |
|---|---|---|---|
| 112 | 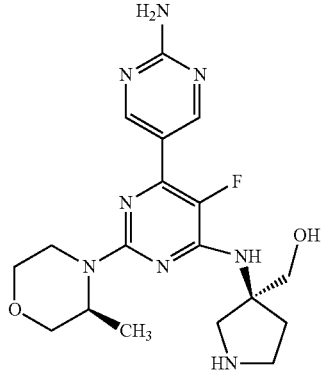 [SMILES: C[C@H]1COCCN1c1nc(N[C@@]2(CO)CCNC2)c(F)c(-c2cnc(N)nc2)n1]<br>[(3S)-3-({2'-amino-5-fluoro-2-[(3S)-3-methylmorpholin-4-yl]-4,5'-bipyrimidin-6-yl}amino)pyrrolidin-3-yl]methanol | 405.0 | 1H NMR (400 MHz, CD3OD) δ 9.05 (s, 2H), 4.57-4.45 (m, 1H), 4.25-4.15 (m, 1H), 4.08-3.90 (m, 4H), 3.80-3.35 (m, 7H), 2.59-2.56 (m, 1H), 2.47-2.44 (m, 1H), 1.32 (d, J = 6.8 Hz, 3H) |
| 113 | 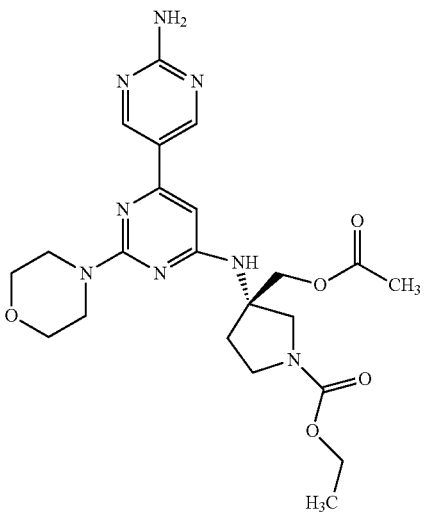 [SMILES: CCOC(=O)N1CC[C@](COC(C)=O)(Nc2cc(-c3cnc(N)nc3)nc(N3CCOCC3)n2)C1]<br>ethyl (3S)-3-[(acetyloxy)methyl]-3-{[2'-amino-2-(morpholin-4-yl)-4,5'-bipyrimidin-6-yl]amino}pyrrolidine-1-carboxylate | 488.1 | 1H NMR (400 MHz, CD3OD) δ 9.12 (s, 2H), 4.57-4.38 (m, 2H), 4.29-4.13 (m, 2H), 4.00-3.80 (m, 5H), 3.78-3.60 (m, 5H), 3.57-3.50 (m, 2H), 2.50-2.39 (m, 1H), 2.30-2.15 (m, 1H), 2.05 (s, 3H), 1.28-1.24 (m, 3H). |

TABLE 1-continued

| Example Number | Structure and Compound Name | LRMS m/z [M + H]+ | 1H NMR |
|---|---|---|---|
| 114 | 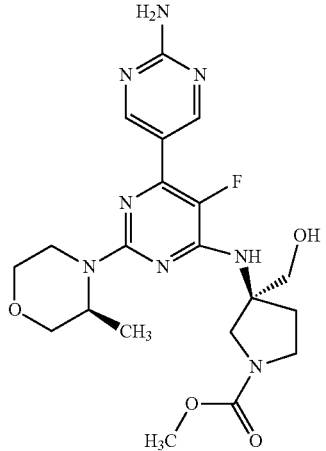 [SMILES: COC(=O)N1CC[C@](CO)(Nc2nc(N3CCOC[C@@H]3C)nc(-c3cnc(N)nc3)c2F)C1]methyl (3S)-3-({2'-amino-5-fluoro-2-[(3S)-3-methylmorpholin-4-yl]-4,5'-bipyrimidin-6-yl}amino)-3-(hydroxymethyl)pyrrolidine-1-carboxylate | 463.1 | 1H NMR (400 MHz, CDCl3) δ 8.91 (s, 2H), 5.39 (s, 2H), 5.11 (s, 1H), 4.57-4.45 (m, 1H), 4.25-3.90 (m, 3H), 3.80-3.50 (m, 11H), 3.32-3.18 (m, 1H), 2.40-2.20 (m, 2H), 1.69 (br s, 1H), 1.28 (d, J = 6.4 Hz, 3H). |
| 115 | 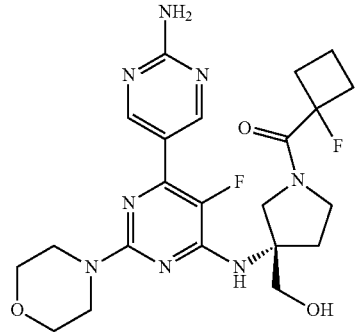 [SMILES: Nc1ncc(-c2nc(N3CCOCC3)nc(N[C@@]3(CO)CCN(C(=O)C4(F)CCC4)C3)c2F)cn1][(3S)-3-{[2'-amino-5-fluoro-2-(morpholin-4-yl)-4,5'-bipyrimidin-6-yl]amino}-3-(hydroxymethyl)pyrrolidin-1-yl](1-fluorocyclobutyl)methanone | 491.2 | 1H NMR (400 MHz, DMSO) δ 8.77 (s, 2H), 7.14 (s, 2H), 7.07-7.02 (m, 1H), 5.05-5.03 (m, 1H), 4.05-3.95 (m, 1H), 3.81-3.77 (m, 2H), 3.67-3.59 (m, 10H), 3.50-3.45 (m, 1H), 2.68-2.52 (m, 2H), 2.47-2.46 (m, 1H), 2.34-2.30 (m, 2H), 2.30-2.28 (m, 1H), 1.84-1.83 (m, 1H), 1.52-1.47 (m, 1H). |
| 116 | 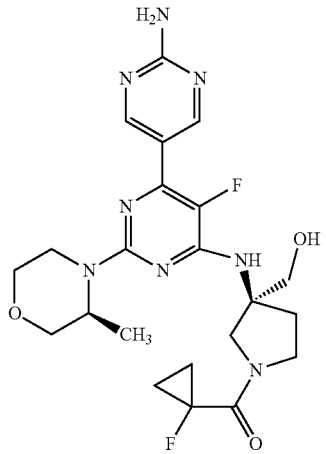 [SMILES: C[C@H]1COCCN1c1nc(N[C@@]2(CO)CCN(C(=O)C3(F)CC3)C2)c(F)c(-c2cnc(N)nc2)n1][(3S)-3-({2'-amino-5-fluoro-2-[(3S)-3-methylmorpholin-4-yl]-4,5'-bipyrimidin-6-yl}amino)-3-(hydroxymethyl)pyrrolidin-1-yl](1-fluorocyclopropyl)methanone | 491.1 | 1H NMR (400 MHz, CDCl3) δ 8.91 (s, 2H), 5.39 (s, 2H), 5.11 (s, 1H), 4.57-4.45 (m, 1H), 4.25-3.90 (m, 3H), 3.80-3.50 (m, 11H), 3.32-3.18 (m, 1H), 2.40-2.20 (m, 2H), 1.69 (br s, 1H), 1.28 (d, J = 6.4 Hz, 3H). |

TABLE 1-continued

| Example Number | Structure and Compound Name | LRMS m/z [M + H]+ | 1H NMR |
|---|---|---|---|
| 117 | 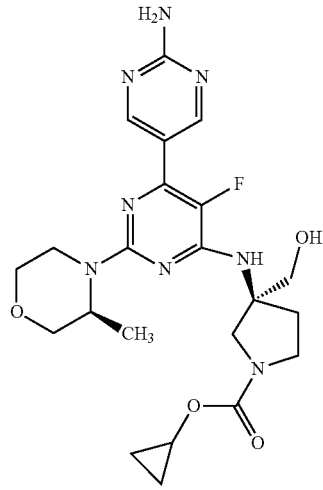 [SMILES: C[C@H]1COCCN1c1nc(N[C@@]2(CO)CCN(C(=O)OC3CC3)C2)c(F)c(-c2cnc(N)nc2)n1]<br>cyclopropyl (3S)-3-({2'-amino-5-fluoro-2-[(3S)-3-methylmorpholin-4-yl]-4,5'-bipyrimidin-6-yl}amino)-3-(hydroxymethyl)pyrrolidine-1-carboxylate | 489.1 | 1H NMR (400 MHz, CDCl$_3$) δ 8.92 (s, 2H), 5.32 (s, 2H), 5.09 (br s, 1H), 4.46 (br s, 1H), 4.18-3.42 (m, 13H), 3.28-3.16 (m, 1H), 2.27 (d, J = 5.8 Hz, 2H), 1.27 (d, J = 6.3 Hz, 3H), 0.69 (m, 4H). |
| 118 | 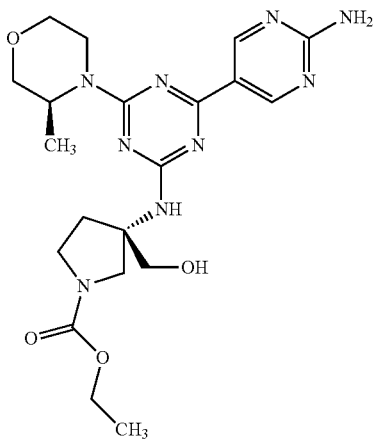 [SMILES: CCOC(=O)N1CC[C@](CO)(Nc2nc(-c3cnc(N)nc3)nc(N3CCOC[C@@H]3C)n2)C1]<br>ethyl (3S)-3-({4-(2-aminopyrimidin-5-yl)-6-[(3S)-3-methylmorpholin-4-yl]-1,3,5-triazin-2-yl}amino)-3-(hydroxymethyl)pyrrolidine-1-carboxylate | 460.0 | 1H NMR (400 MHz, CDCl$_3$) δ 9.09 (s, 2H), 5.41 (m, 3H), 4.75-4.51 (m, 3H), 4.12-3.51 (m, 12H), 3.31-3.24 (m, 1H), 2.23-2.17 (m, 2H), 1.33 (d, J = 6.8 Hz, 3H), 1.26-1.24 (m, 3H). |

TABLE 1-continued

| Example Number | Structure and Compound Name | LRMS m/z [M + H]+ | 1H NMR |
|---|---|---|---|
| 119 | 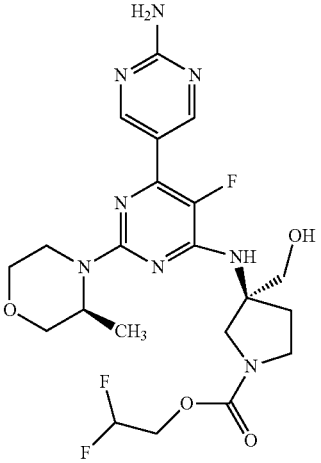 [SMILES: C[C@H]1COCCN1c1nc(N[C@@]2(CO)CCN(C(=O)OCC(F)F)C2)c(F)c(-c2cnc(N)nc2)n1]<br>2,2-difluoroethyl (3S)-3-({2'-amino-5-fluoro-2-[(3S)-3-methylmorpholin-4-yl]-4,5'-bipyrimidin-6-yl}amino)-3-(hydroxymethyl)pyrrolidine-1-carboxylate | 513.1 | 1H NMR (400 MHz, CDCl3) δ 8.91 (s, 2H), 6.11-5.80 (m, 1H), 5.33 (s, 2H), 5.10 (d, J = 6.8 Hz, 1H), 4.46 (br s, 1H), 4.34-4.22 (m, 2H), 4.16-3.95 (m, 3H), 3.92-3.48 (m, 9H), 3.22 (t, J = 12.5 Hz, 1H), 2.38-2.26 (m, 2H), 1.27 (dd, J = 6.7, 4.4 Hz, 3H). |
| 120 | 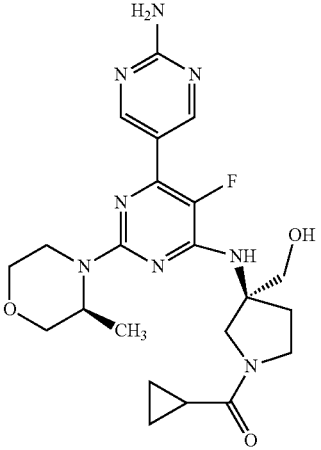 [SMILES: C[C@H]1COCCN1c1nc(N[C@@]2(CO)CCN(C(=O)C3CC3)C2)c(F)c(-c2cnc(N)nc2)n1]<br>[(3S)-3-({2'-amino-5-fluoro-2-[(3S)-3-methylmorpholin-4-yl]-4,5'-bipyrimidin-6-yl}amino)-3-(hydroxymethyl)pyrrolidin-1-yl](cyclopropyl)methanone | 473.0 | 1H NMR (400 MHz, CDCl3) δ 8.92 (s, 2H), 5.33 (s, 2H), 5.17-5.11 (m, 1H), 4.48-4.47 (m, 1H), 4.25-3.50 (m, 12H), 3.30-3.15 (m, 1H), 2.62-2.50 (m, 1H), 2.50-2.39 (m, 1H), 2.30-2.15 (m, 1H), 1.30-1.20 (m, 3H), 1.03-0.95 (m, 2H), 0.82-0.77 (m, 2H). |

TABLE 1-continued
| Example Number | Structure and Compound Name | LRMS m/z [M + H]+ | 1H NMR |
|---|---|---|---|
| 121 | 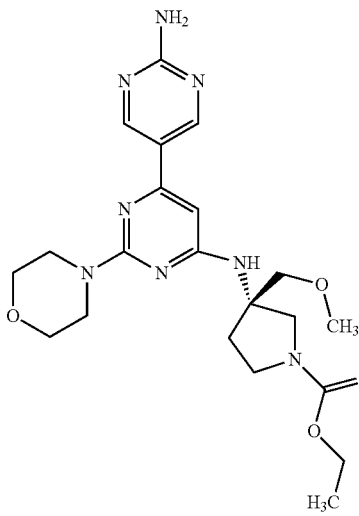<br>ethyl (3S)-3-{[2'-amino-2-(morpholin-4-yl)-4,5'-bipyrimidin-6-yl]amino}-3-(methoxymethyl)pyrrolidine-1-carboxylate | 459.0 | 1H NMR (400 MHz, CDCl3) δ 8.84 (s, 2H), 6.02 (s, 1H), 5.27 (s, 1H), 4.90-4.80 (m, 1H), 4.15-4.10 (m, 2H), 3.89-3.83 (m, 1H), 3.82-3.50 (m, 12H), 3.37 (s, 3H), 2.53-2.50 (m, 1H), 2.18-2.13 (m, 1H), 1.30-1.20 (m, 3H). |
| 122 | 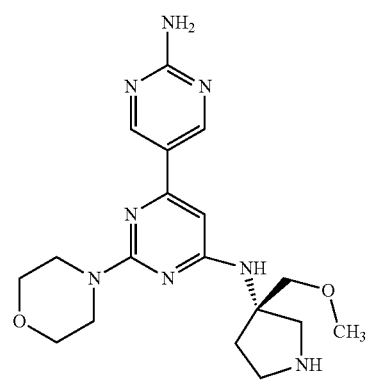 [SMILES: COC[C@]1(Nc2cc(-c3cnc(N)nc3)nc(N3CCOCC3)n2)CCNC1]<br>N-6~-[(3S)-3-(methoxymethyl)pyrrolidin-3-yl]-2-(morpholin-4-yl)-4,5'-bipyrimidine-2',6-diamine | 386.9 | 1H NMR (400 MHz, D2O) δ 8.70-8.66 (m, 2H), 6.33-6.31 (m, 1H), 4.06-3.99 (m, 2H), 3.89-3.83 (m, 9H), 3.82-3.57 (m, 3H), 3.40 (s, 3H), 2.53-2.50 (m, 1H), 2.45-2.40 (m, 1H). |

TABLE 1-continued

| Example Number | Structure and Compound Name | LRMS m/z [M + H]+ | 1H NMR |
|---|---|---|---|
| 123 | 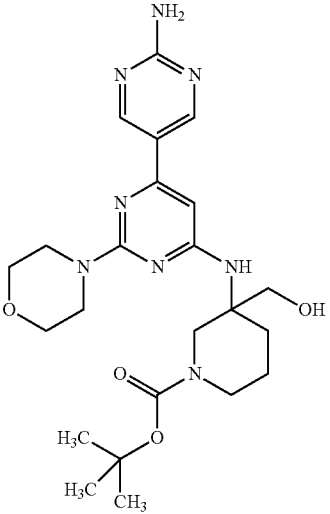 [SMILES: CC(C)(C)OC(=O)N1CCCC(CO)(Nc2cc(-c3cnc(N)nc3)nc(N3CCOCC3)n2)C1]

tert-butyl 3-{[2'-amino-2-(morpholin-4-yl)-4,5'-bipyrimidin-6-yl]amino}-3-(hydroxymethyl)piperidine-1-carboxylate | 487.3 | 1H NMR (400 MHz, DMSO-$d_6$, 80° C.) δ 8.73 (s, 2H), 6.61 (br s, 2H), 6.32 (s, 1H), 5.94 (br s, 1H), 4.53 (br s, 1H), 4.27-4.14 (m, 1H), 3.78 (s, 2H), 3.68 (s, 8H), 3.63-3.56 (m, 1H), 3.27 (d, J = 13.2 Hz, 1H), 2.11-2.00 (m, 1H), 1.84-1.59 (m, 3H), 1.55-1.44 (m, 1H), 1.30 (s, 9H). |
| 124 | 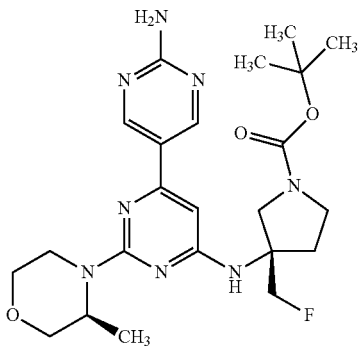 [SMILES: C[C@H]1COCCN1c1nc(N[C@@]2(CF)CCN(C(=O)OC(C)(C)C)C2)cc(-c2cnc(N)nc2)n1]

tert-butyl (3S)-3-({2'-amino-2-[(3S)-3-methylmorpholin-4-yl]-4,5'-bipyrimidin-6-yl}amino)-3-(fluoromethyl)pyrrolidine-1-carboxylate | 489.1 | 1H NMR (400 MHz, METHANOL-$d_4$) δ 8.81 (s, 2H), 6.22 (s, 1H), 4.65 (br s, 1H), 4.34 (d, J = 15.3 Hz, 1H), 4.02-3.87 (m, 2H), 3.86-3.67 (m, 3H), 3.62 (d, J = 11.8 Hz, 1H), 3.59-3.38 (m, 4H), 2.42-2.18 (m, 3H), 1.49-1.40 (m, 9H), 1.29 (d, J = 6.5 Hz, 3H). |
| 125 | 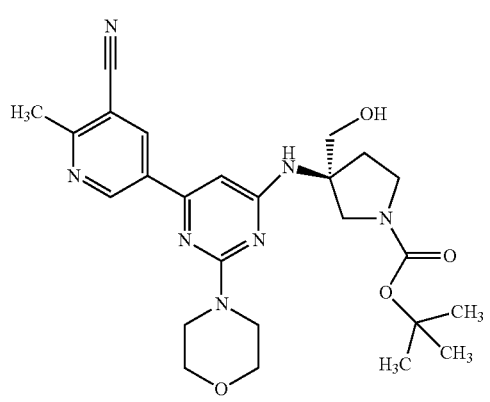 [SMILES: Cc1ncc(-c2cc(N[C@@]3(CO)CCN(C(=O)OC(C)(C)C)C3)nc(N3CCOCC3)n2)cc1C#N]

tert-butyl (3S)-3-{[6-(5-cyano-6-methylpyridin-3-yl)-2-(morpholin-4-yl)pyrimidin-4-yl]amino}-3-(hydroxymethyl)pyrrolidine-1-carboxylate | 496.0 | 1H NMR (400 MHz, CDCl$_3$) δ 9.12 (d, J = 2.3 Hz, 1H), 8.49 (d, J = 2.0 Hz, 1H), 6.17 (s, 1H), 4.90 (br s, 1H), 4.35-4.13 (s, 1H), 3.99-3.60 (m, 12H), 3.57-3.43 (m, 2H), 2.83 (s, 3H), 2.40-2.10 (m, 2H), 1.46 (s, 9H). |

TABLE 1-continued

| Example Number | Structure and Compound Name | LRMS m/z [M + H]+ | 1H NMR |
|---|---|---|---|
| 126 | tert-butyl (3S)-3-(hydroxymethyl)-3-{[2'-methyl-2-(morpholin-4-yl)-4,5'-bipyrimidin-6-yl]amino}pyrrolidine-1-carboxylate | 472.0 | 1H NMR (400 MHz, CDCl3) δ 9.11 (s, 2H), 6.15 (s, 1H), 4.89 (br s, 1H), 4.31 (br s, 1H), 4.00-3.84 (m, 2H), 3.78 (s, 8H), 3.71-3.59 (m, 2H), 3.49 (d, J = 6.8 Hz, 2H), 2.79 (s, 3H), 2.33 (br s, 1H), 2.20 (d, J = 7.3 Hz, 1H), 1.46 (br s, 9H). |
| 127 | tert-butyl (3S)-3-{[6-(5-fluoro-6-methylpyridin-3-yl)-2-(morpholin-4-yl)pyrimidin-4-yl]amino}-3-(hydroxymethyl)pyrrolidine-1-carboxylate | 489.1 | 1H NMR(400 MHz, CDCl3) δ 8.77 (s, 1H), 7.93 (d, J = 10.0 Hz, 1H), 6.17 (s, 1H), 4.86 (s, 1H), 4.65-4.40 (m, 1H), 3.99-3.60 (m, 12H), 3.57-3.43 (m, 2H), 2.58 (s, 3H), 2.40-2.12 (m, 2H), 1.46 (s, 9H). |
| 128 | ethyl (3S)-3-{[6-(5-cyano-6-methylpyridin-3-yl)-2-(morpholin-4-yl)pyrimidin-4-yl]amino}-3-(hydroxymethyl)pyrrolidine-1-carboxylate | 468.1 | 1H NMR (400 MHz, CDCl3) δ 9.12 (d, J = 2.3 Hz, 1H), 8.49 (d, J = 2.0 Hz, 1H), 6.21-6.13 (m, 1H), 4.91 (br s, 1H), 4.28-3.65 (m, 14H), 3.62-3.48 (m, 2H), 2.83 (s, 3H), 2.36 (br s, 1H), 2.22 (d, J = 6.8 Hz, 1H), 1.26 (t, J = 7.0 Hz, 3H). |

TABLE 1-continued

| Example Number | Structure and Compound Name | LRMS m/z [M + H]⁺ | ¹H NMR |
|---|---|---|---|
| 129 | 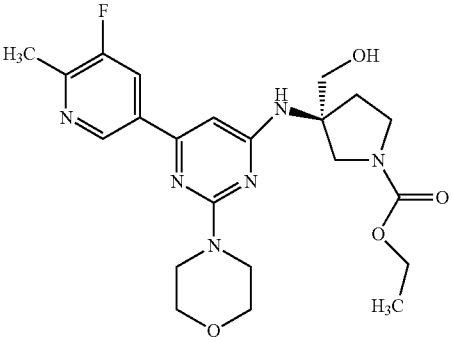 [SMILES: CCOC(=O)N1CC[C@](CO)(Nc2cc(-c3cnc(C)c(F)c3)nc(N3CCOCC3)n2)C1]<br>ethyl (3S)-3-{[6-(5-fluoro-6-methylpyridin-3-yl)-2-(morpholin-4-yl)pyrimidin-4-yl]amino}-3-(hydroxymethyl)pyrrolidine-1-carboxylate | 460.9 | ¹H NMR (400 MHz, CDCl₃) δ 8.77 (s, 1H), 7.93 (d, J = 10.3 Hz, 1H), 6.17 (s, 1H), 4.83 (s, 1H), 4.39 (br s, 1H), 4.15 (d, J = 5.5 Hz, 2H), 3.90 (br s, 2H), 3.65-3.84 (m, 10H), 3.54 (d, J = 8.0 Hz, 2H), 2.58 (d, J = 2.8 Hz, 3H), 2.35 (br s, 1H), 2.21 (s, 1H), 1.26 (br s, 3H). |
| 130 | 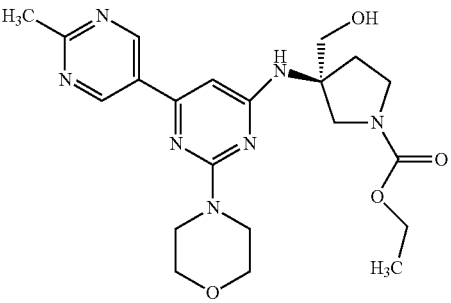 [SMILES: CCOC(=O)N1CC[C@](CO)(Nc2cc(-c3cnc(C)nc3)nc(N3CCOCC3)n2)C1]<br>ethyl (3S)-3-(hydroxymethyl)-3-{[2'-methyl-2-(morpholin-4-yl)-4,5'-bipyrimidin-6-yl]amino}pyrrolidine-1-carboxylate | 443.8 | ¹H NMR (400 MHz, CDCl₃) δ 9.11 (s, 2H), 6.15 (s, 1H), 4.86 (s, 1H), 4.40 (br s, 1H), 4.15 (d, J = 6.0 Hz, 2H), 4.00-3.84 (m, 2H), 3.84-3.64 (m, 10H), 3.64-3.45 (m, 2H), 2.80 (s, 3H), 2.36 (br s, 1H), 2.29-2.08 (m, 1H), 1.26 (br s, 3H). |
| 131 | 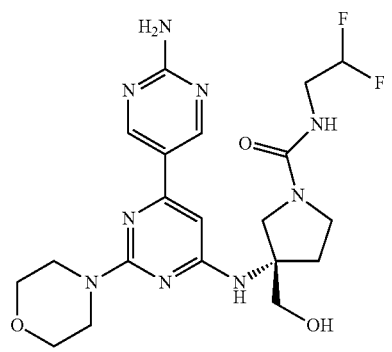 [SMILES: Nc1ncc(-c2cc(N[C@@]3(CO)CCN(C(=O)NCC(F)F)C3)nc(N3CCOCC3)n2)cn1]<br>(3S)-3-{[2'-amino-2-(morpholin-4-yl)-4,5'-bipyrimidin-6-yl]amino}-N-(2,2-difluoroethyl)-3-(hydroxymethyl)pyrrolidine-1-carboxamide | 480.2 | ¹H NMR (400 MHz, METHANOL-d₄) δ 8.82 (s, 2H), 6.25 (s, 1H), 6.03-5.68 (m, 1H), 4.04 (d, J = 11.3 Hz, 1H), 3.90 (dd, J = 6.8, 11.0 Hz, 2H), 3.77 (s, 8H), 3.62 (d, J = 10.8 Hz, 1H), 3.58-3.43 (m, 4H), 2.43 (td, J = 12.4, 6.3 Hz, 1H), 2.30-2.18 (m, 1H). |

TABLE 1-continued

| Example Number | Structure and Compound Name | LRMS m/z [M + H]+ | 1H NMR |
|---|---|---|---|
| 132 | 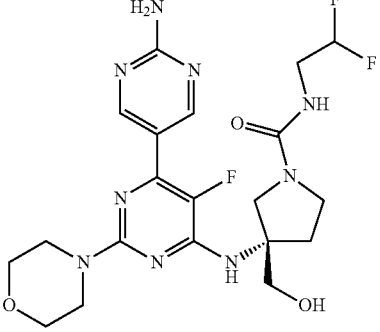<br>(3S)-3-{[2'-amino-5-fluoro-2-(morpholin-4-yl)-4(5'-bipyrimidin-6-yl]amino}-N-(2,2-difluoroethyl)-3-(hydroxymethyl)pyrrolidine-1-carboxamide | 498.0 | 1H NMR (400 MHz, METHANOL-d4) δ 8.89 (s, 2H), 5.90-5.70 (m, 1H), 4.05 (d, J = 11.3 Hz, 1H), 3 98-3.84 (m, 2H), 3.80-3.63 (m, 9H), 3.62-3.37 (m, 4H), 2.56-2.46 (m, 1H), 2.28 (d, J = 8.0 Hz, 1H). |
| 133 | 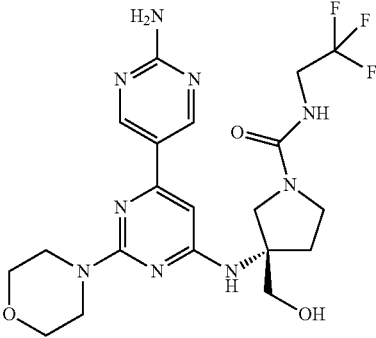 [SMILES: Nc1ncc(-c2cc(N[C@@]3(CO)CCN(C(=O)NCC(F)(F)F)C3)nc(N3CCOCC3)n2)cn1]<br>(3S)-3-{[2'-amino-2-(morpholin-4-yl)-4,5'-bipyrimidin-6-yl]amino}-3-(hydroxymethyl)-N-(2,2,2-trifluoroethyl)pyrrolidine-1-carboxamide | 498.0 | 1H NMR (400 MHz, METHANOL-d4) δ 8.82 (s, 2H), 6.25 (s, 1H), 4.04 (d, J = 11.3 Hz, 1H), 3.96-3.71 (m, 12H), 3.67-3.47 (m, 3H), 2.49-2.38 (m, 1H), 2.26 (d, J = 6.5 Hz, 1H). |
| 134 | 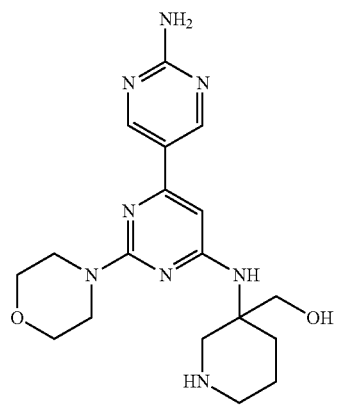 [SMILES: Nc1ncc(-c2cc(NC3(CO)CCCNC3)nc(N3CCOCC3)n2)cn1]<br>(3-{[2'-amino-2-(morpholin-4-yl)-4,5'-bipyrimidin-6-yl]amino}piperidin-3-yl)methanol | 387.3 | 1H NMR (400 MHz, DMSO-d6, 80° C.) δ 9.38 (br s, 1H), 8.72 (s, 2H), 8.63 (br s, 1H), 7.43 (br s, 1H), 6.48 (s, 1H), 3.94 (d, J = 12.6 Hz, 1H), 3.85 (d, J = 11.0 Hz, 1H), 3.76-3.65 (m, 9H), 3.22-3.11 (m, 1H), 3.10-2.99 (m, 1H), 2.94-2.80 (m, 1H), 2.35-2.23 (m, 1H), 1.98-1.81 (m, 1H), 1.78-1.64 (m, 2H). |

TABLE 1-continued

| Example Number | Structure and Compound Name | LRMS m/z [M + H]+ | 1H NMR |
|---|---|---|---|
| 135 | (3S)-3-{[2'-amino-5-fluoro-2-(morpholin-4-yl)-4,5'-bipyrimidin-6-yl]amino}-3-(hydroxymethyl)-N-(2,2,2-trifluoroethyl)pyrrolidine-1-carboxamide | 516.2 | 1H NMR (400 MHz, METHANOL-$d_4$) δ 8.87 (s, 2H), 4.03 (d, J = 11.5 Hz, 1H), 3.93 (d, J = 11.0 Hz, 1H), 3.89-3.79 (m, 3H), 3.77-3.62 (m, 9H), 3.59-3.42 (m, 2H), 2.54-2.44 (m, 1H), 2.30 (d, J = 5.0 Hz, 1H). |
| 136 | (1-fluorocyclopropyl)[(3S)-3-(hydroxymethyl)-3-{[2'-methyl-2-(morpholin-4-yl)-4,5'-bipyrimidin-6-yl]amino}pyrrolidin-1-yl]methanone | 458.0 | 1H NMR (400 MHz, DMSO) δ 9.13 (s, 2H), 7.34-7.31 (m, 1H), 6.42 (d, J = 4.8 Hz, 1H), 5.06-5.00 (m, 1H), 4.23-3.49 (m, 14H), 2.69 (s, 3H), 2.49-2.12 (m, 2H), 1.27-1.09 (m, 4H). |
| 137 | [(3S)-3-{[2'-amino-5-fluoro-2-(morpholin-4-yl)-4,5'-bipyrimidin-6-yl]amino}pyrrolidin-3-yl]methanol | 391.0 | 1H NMR (400 MHz, $D_2O$) δ 2.38-2.32 (m, 1H), 2.52-2.49 (m, 1H), 3.40-3.53 (m, 3H), 3.65-3.70 (m, 4H), 3.73-3.79 (m, 4H), 3.96 (d, J = 13. Hz, 1H), 4.04 (d, J = 11.8 Hz, 2H) 8.72 (s, 2H). |

TABLE 1-continued

| Example Number | Structure and Compound Name | LRMS m/z [M + H]+ | 1H NMR |
|---|---|---|---|
| 138 | 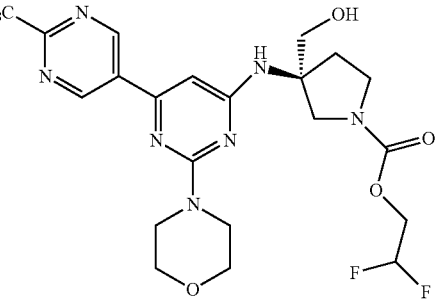

2,2-difluoroethyl (3S)-3-(hydroxymethyl)-3-{[2'-methyl-2-(morpholin-4-yl)-4,5'-bipyrimidin-6-yl]amino}pyrrolidine-1-carboxylate | 479.9 | 1H NMR (400 MHz, METHANOL-$d_4$) δ 9.20 (s, 2H), 6.42 (s, 1H), 6.18-5.93 (m, 1H), 4.37-4.24 (m, 2H), 4.05-3.88 (m, 3H), 3.79 (d, J = 6.8 Hz, 8H), 3.68-3.52 (m, 3H), 2.76 (s, 3H), 2.43-2.33 (m, 1H), 2.32-2.23 (m, 1H). |
| 139 | 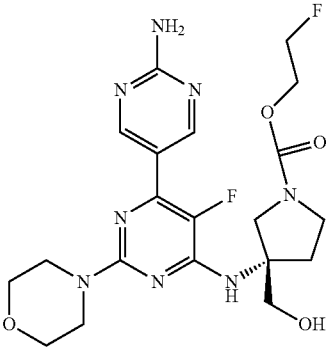 [SMILES: Nc1ncc(-c2nc(N3CCOCC3)nc(N[C@@]3(CO)CCN(C(=O)OCCF)C3)c2F)cn1]

2-fluoroethyl (3S)-3-{[2'-amino-5-fluoro-2-(morpholin-4-yl)-4,5'-bipyrimidin-6-yl]amino}-3-(hydroxymethyl)pyrrolidine-1-carboxylate | 481.2 | 1H NMR (400 MHz, 80° C., DMSO-$d_6$) δ 8.77 (s, 2H), 6.74 (s, 2H), 6.56 (s, 1H), 4.76 (br s, 1H), 4.66-4.62 (m, 1H), 4.53-4.50 (m, 1H), 4.30-4.26 (m, 1H), 4.22-4.18 (m, 1H), 3.89 (d, J = 11.5 Hz, 1H), 3.81-3.72 (m, 2H), 3.70-3.57 (m, 9H), 3.52-3.37 (m, 2H), 2.47-2.38 (m, 1H), 2.22-2.13 (m, 1H). |
| 140 | 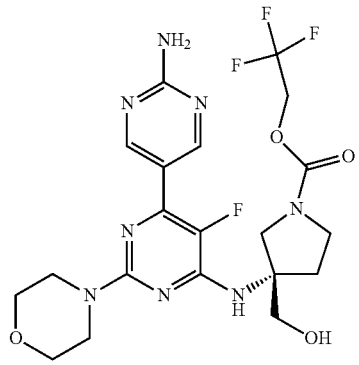 [SMILES: Nc1ncc(-c2nc(N3CCOCC3)nc(N[C@@]3(CO)CCN(C(=O)OCC(F)(F)F)C3)c2F)cn1]

2,2,2-trifluoroethyl(3S)-3-{[2'-amino-5-fluoro-2-(morpholin-4-yl)-4,5'-bipyrimidin-6-yl]amino}-3-(hydroxymethyl)pyrrolidine-1-carboxylate | 517.2 | 1H NMR (400 MHz, 80° C., DMSO-$d_6$) δ 8.77 (s, 2H), 6.74 (s, 2H), 6.61 (s, 1H), 4.84-4.74 (m, 1H), 4 63 (q, J = 9.1 Hz, 2H), 3.95 (d, J = 11.5 Hz, 1H), 3.81-3.74 (m, 2H), 3.69-3.59 (m, 9H), 3.56-3.40 (m, 2H), 2.47-4.41 (m, 1H), 2.26-2.16 (m 1H). |

TABLE 1-continued

| Example Number | Structure and Compound Name | LRMS m/z [M + H]+ | 1H NMR |
|---|---|---|---|
| 141 | 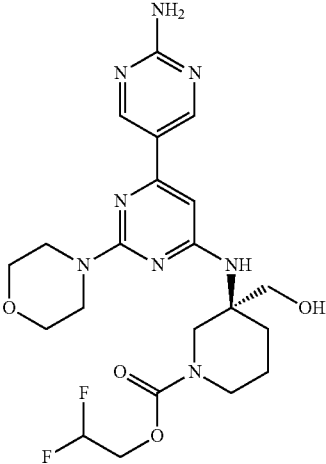 [SMILES: Nc1ncc(-c2cc(N[C@@]3(CO)CCCN(C(=O)OCC(F)F)C3)nc(N3CCOCC3)n2)cn1]<br>2,2-difluoroethyl (3S)-3-{[2'-amino-2-(morpholin-4-yl)-4,5'-bipyrimidin-6-yl]amino}-3-(hydroxymethyl)piperidine-1-carboxylate | 495.3 | 1H NMR (400 MHz, DMSO-$d_6$) δ 8.73 (s, 2H), 6.62 (br s, 2H), 6.32 (s, 1H), 5.99 (s, 1H), 4.33-4.04 (m, 2H), 3.87-3.72 (m, 2H), 3.68 (s, 9H), 3.63-3.49 (m, 3H), 3.26 (d, J = 8.9 Hz, 1H), 2.14-2.01 (m, 1H), 1.87-1.75 (m, 1H), 1.68 (dt, J = 8.9, 4.5 Hz, 1H), 1.60-1.49 (m, 1H) |
| 142 | 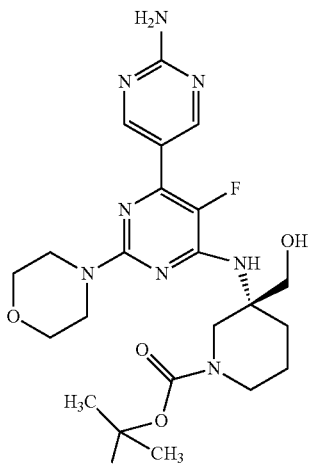<br>tert-butyl (3R)-3-{[2'-amino-5-fluoro-2-(morpholin-4-yl)-4,5'-bipyrimidin-6-yl]amino}-3-(hydroxymethyl)piperidine-1-carboxylate | 505.3 | 1H NMR (CDCl$_3$, 400 MHz) δ 8.92 (s, 2H), 5.33 (br s, 2H), 4.89-4.68 (m, 1H), 4.39-4.17 (m, 1H), 3.91-3.82 (m, 1H), 3.81-3.72 (m, 5H), 3.68-3.66 (m, 4H), 2.97-2.93 (m, 3H), 1.64 (br s, 9H), 1.60-1.53 (m, 3H). |

TABLE 1-continued

| Example Number | Structure and Compound Name | LRMS m/z [M + H]+ | 1H NMR |
|---|---|---|---|
| 143 | 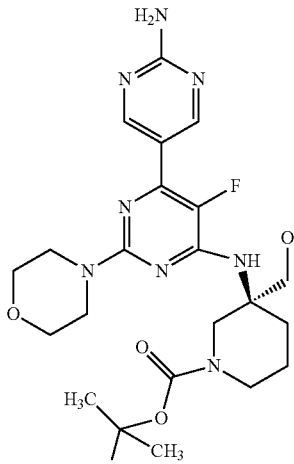<br>tert-butyl (3S)-3-{[2'-amino-5-fluoro-2-(morpholin-4-yl)-4,5'-bipyrimidin-6-yl]amino}-3-(hydroxymethyl)piperidine-1-carboxylate | 505.3 | 1H NMR (CDCl3, 400 MHz) δ 8.91 (s, 2H), 5.35 (br s, 2H), 4.90-4.78 (m, 1H), 4.35-4.20 (m, 1H), 3.90-3.84 (m, 1H), 3.77-3.76 (m, 5H), 3.66-3.65 (m, 4H), 3.06-2.80 (m, 3H), 1.66 (br s, 9H), 1.61-1.50 (m, 3H). |
| 144 | 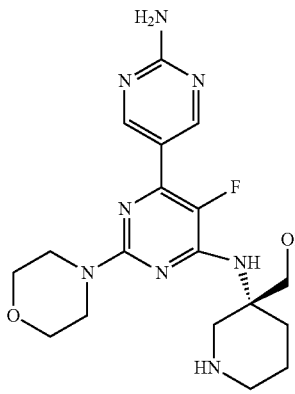<br>[(3R)-3-{[2'-amino-5-fluoro-2-(morpholin-4-yl)-4,5'-bipyrimidin-6-yl]amino}piperidin-3-yl]methanol | 405.2 | 1H NMR (400 MHz, METHANOL-d4) δ 9.21-8.93 (m, 2H), 4.54-4.35 (m, 1H), 3.90-3.82 (m, 10H), 3.46-3.34 (m, 1H), 3.25-3.01 (m, 2H), 2.58-2.39 (m, 1H), 2.20-1.78 (m, 3H). |
| 145 | 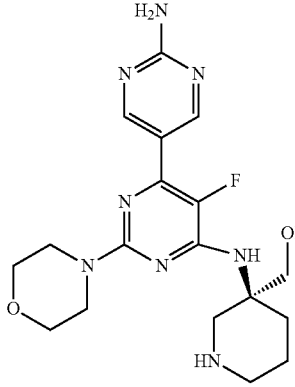<br>[(3S)-3-{[2'-amino-6-fluoro-2-(morpholin-4-yl)-4,5'-bipyrimidin-6-yl]amino}piperidin-3-yl]methanol | 405.2 | 1H NMR (400 MHz, METHANOL-d4) δ 9.17-8.94 (m, 2H), 4.49-4.37 (m, 1H), 3.96-3.70 (m, 10H), 3.39-3.35 (m, 1H) 3.24-3.14 (m, 1H) 3.12-3.00 (m, 1H) 2.53-2.41 (m, 1H) 2.14-1.83 (m, 3H) |

TABLE 1-continued
| Example Number | Structure and Compound Name | LRMS m/z [M + H]+ | 1H NMR |
|---|---|---|---|
| 146 | 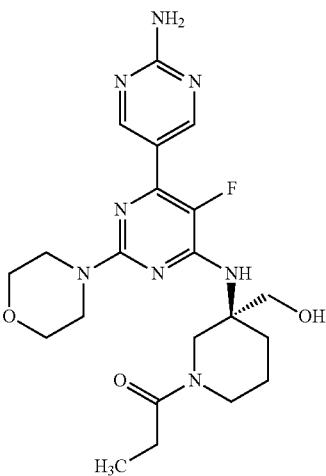 [SMILES: CCC(=O)N1CCC[C@](CO)(Nc2nc(N3CCOCC3)nc(-c3cnc(N)nc3)c2F)C1]<br>1-[(3S)-3-{[2'-amino-5-fluoro-2-(morpholin-4-yl)-4,5'-bipyrimidin-6-yl]amino}-3-(hydroxymethyl)piperidin-1-yl]propan-1-one | 461.0 | 1H NMR (400 MHz, DMSO) δ 8.77-8.75 (m, 2H), 7.14-7.11 (m, 2H), 6.12-5.74 (m, 1H), 4.90-4.81 (m, 1H), 4.34-4.22 (m, 1H), 3.89-3.81 (m, 1H), 3.65-3.60 (m, 10H), 3.22-3.18 (m, 2H), 2.49-2.16 (m, 3H), 1.59-1.54 (m, 3H), 1.02-0.87 (m, 3H). |
| 147 | 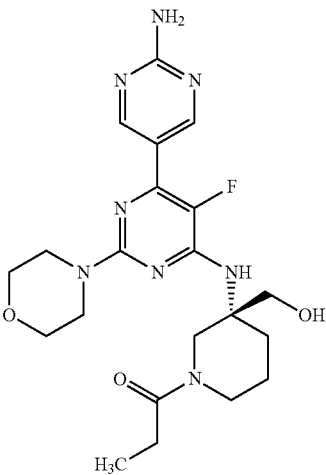 [SMILES: CCC(=O)N1CCC[C@@](CO)(Nc2nc(N3CCOCC3)nc(-c3cnc(N)nc3)c2F)C1]<br>1-[(3R)-3-{[2'-amino-5-fluoro-2-(morpholin-4-yl)-4,5'-bipyrimidin-6-yl]amino}-3-(hydroxymethyl)piperidin-1-yl]propan-1-one | 483.0 [M + 23] | 1H NMR (400 MHz, DMSO) δ 8.77-8.75 (m, 2H), 7.14-7.11 (m, 2H), 6.12-5.74 (m, 1H), 4.90-4.81 (m, 1H), 4.34-4.22 (m, 1H), 3.89-3.81 (m, 1H), 3.65-3.55 (m, 10H), 3.22-3.18 (m, 2H), 2.49-2.16 (m, 3H), 1.59-1.54 (m, 3H), 1.02-0.87 (m, 3H). |

TABLE 1-continued

| Example Number | Structure and Compound Name | LRMS m/z [M + H]+ | 1H NMR |
|---|---|---|---|
| 148 | 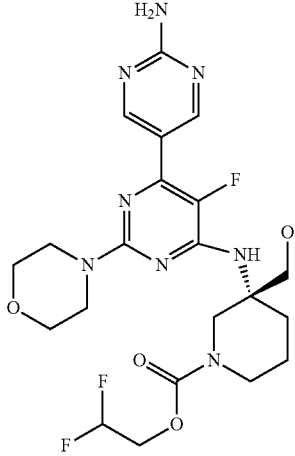<br>2,2-difluoroethyl (3R)-3-{[2'-amino-5-fluoro-2-(morpholin-4-yl)-4,5'-bipyrimidin-6-yl]amino}-3-(hydroxymethyl)piperidine-1-carboxylate | 513.0 | 1H NMR (400 MHz, DMSO-$d_6$) δ 8.77 (s, 2H), 7.14 (br s, 2H), 6.40-6.05 (m, 1H), 5.98-5.74 (m, 1H), 4.84 (br s, 1H), 4.39-4.01 (m, 3H), 3.92-3.43 (m, 12H), 3.22 (br s, 1H), 2.14 (br s, 1H), 1.85-1.44 (m, 3H). |
| 149 | 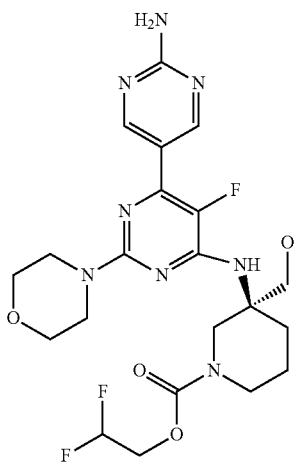<br>2,2-difluoroethyl (3S)-3-{[2'-amino-5-fluoro-2-morpholin-4-yl)-4,5'-bipyrimidin-6-yl]amino}-3-(hydroxymethyl)piperidine-1-carboxylate | 513.2 | 1H NMR (400 MHz, DMSO-$d_6$) δ 8.77 (s, 2H), 7.14 (s, 2H), 5.90 (br s, 1H), 4.84 (br s, 1H), 4.30 (d, J = 14.8 Hz, 1H), 4.13 (br s, 1H), 3.84 (br s, 1H), 3.73 (br s, 1H), 3.67 (d, J = 4.3 Hz, 4H), 3.60 (br s, 4H), 3.48 (d, J = 14.3 Hz, 1H), 3.28-3.16 (m, 1H), 1.54 (br s, 2H). |

TABLE 1-continued

| Example Number | Structure and Compound Name | LRMS m/z [M + H]⁺ | ¹H NMR |
|---|---|---|---|
| 150 | 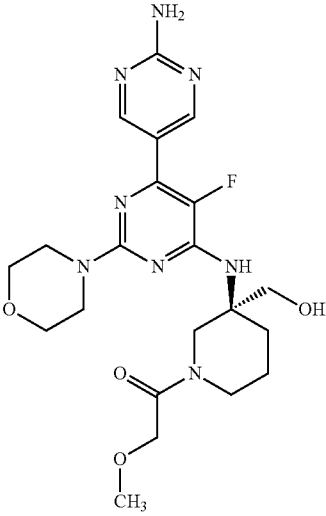 [SMILES: COCC(=O)N1CCC[C@](CO)(Nc2nc(N3CCOCC3)nc(-c3cnc(N)nc3)c2F)C1]<br>1-[(3S)-3-{[2'-amino-5-fluoro-2-(morpholin-4-yl)-4,5'-bipyrimidin-6-yl]amino}-3-(hydroxymethyl)piperidin-1-yl]-2-methoxyethanone | 477.0 | ¹H NMR (400 MHz, CHLOROFORM-d) δ 8.85 (br s, 2H), 6.14 (br s, 1H), 5.56-5.34 (m, 2H), 4.52-4.30 (m, 1H), 4.24-4.15 (m, 2H), 4.02 (d, J = 11.80 Hz, 1H), 3.97-3.86 (m, 1H), 3.86-3.69 (m, 5H), 3.69-3.53 (m, 4H), 3.49 (s, 2 H), 3.43 (s, 1H), 3.11 (d, J = 13.5 Hz, 1H), 2.98-2.69 (m, 2H), 1.66 (br s, 1H), 1.64-1.50 (m, 2H), 1.50-1.34 (m, 1H). |
| 151 | 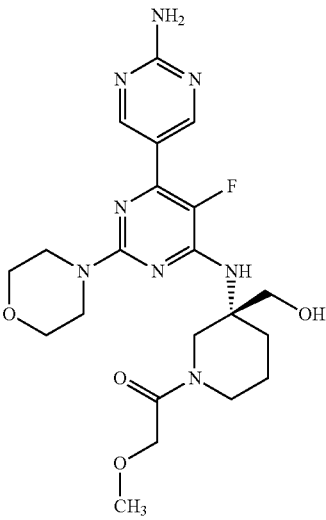 [SMILES: COCC(=O)N1CCC[C@@](CO)(Nc2nc(N3CCOCC3)nc(-c3cnc(N)nc3)c2F)C1]<br>1-[(3R)-3-{[2'-amino-5-fluoro-2-(morpholin-4-yl)-4,5'-bipyrimidin-6-yl]amino}-3-(hydroxymethyl)piperidin-1-yl]-2-methoxyethanone | 477.2 | ¹H NMR (400 MHz, CHLOROFORM-d) δ 8.94-8.82 (m, 2H), 6.15 (br s, 1H), 5.38 (s, 2H), 4.53 (br s, 1H), 4.49-4.27 (m, 1H), 4.27-4.12 (m, 2H), 4.03 (d, J = 12.0 Hz, 1H), 3.84-3.68 (m, 5H), 3.68-3.56 (m, 4H), 3.49 (s, 2H), 3.44 (s, 1H), 3.17-2.98 (m, 1H), 2.98-2.72 (m, 2H), 1.66-1.36 (m, H). |

TABLE 1-continued

| Example Number | Structure and Compound Name | LRMS m/z [M + H]⁺ | ¹H NMR |
|---|---|---|---|
| 152 | 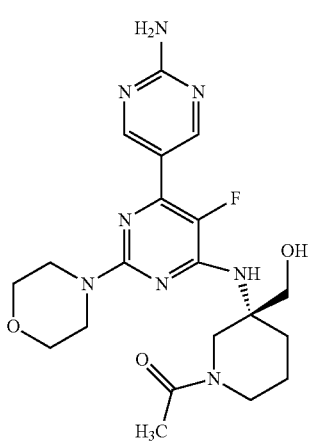 [SMILES: CC(=O)N1CCC[C@@](CO)(Nc2nc(N3CCOCC3)nc(-c3cnc(N)nc3)c2F)C1]<br>1-[(3R)-3-{[2'-amino-5-fluoro-2-(morpholin-4-yl)-4,5'-bipyrimidin-6-yl]amino}-3-(hydroxymethyl)piperidin-1-yl]ethanone | 447.2 | ¹H NMR (400 MHz, METHANOL-d₄) δ 8.88-8.86 (m, 2H), 5.75-5.74 (m, 1H), 4.61-4.42 (m, 1H), 4.08-3.99 (m, 1H), 3.92-3.86 (m, 1H), 3.77-3.66 (m, 8H), 3.57-3.46 (m, 1H), 3.67-3.35 (m, 1H), 3.18-2.51 (m, 1H), 2.26-2.17 (m, 1H), 1.94-1.87 (m, 1H), 2.16-1.95 (m, 3H), 1.84-1.59 (m, 3H). |
| 153 | 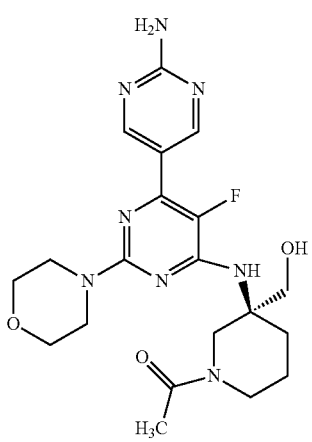 [SMILES: CC(=O)N1CCC[C@](CO)(Nc2nc(N3CCOCC3)nc(-c3cnc(N)nc3)c2F)C1]<br>1-[(3S)-3-{[2'-amino-5-fluoro-2-(morpholin-4-yl)-4,5'-bipyrimidin-6-yl]amino}-3-(hydroxymethyl)piperidin-1-yl]ethanone | 447.3 | ¹HNMR (400 MHz, METHANOL-d₄) δ 8.90-8.83 (m, 2H), 5.75-5.71 (m, 1H), 4.58-4.39 (m, 1H), 4.07-3.99 (m, 1H), 3.92-3.86 (m, 1H), 3.77-3.67 (m, 8H), 3.56-3.45 (m, 1H), 3.67-3.36 (m, 1H), 3.18-3.08 (m, 1H), 2.62-2.53 (m, 1H), 2.30-1.86 (m, 1H), 2.16-1.95 (m, 3H), 1.86-1.50 (m, 3H). |

TABLE 1-continued

| Example Number | Structure and Compound Name | LRMS m/z [M + H]+ | 1H NMR |
|---|---|---|---|
| 154 | 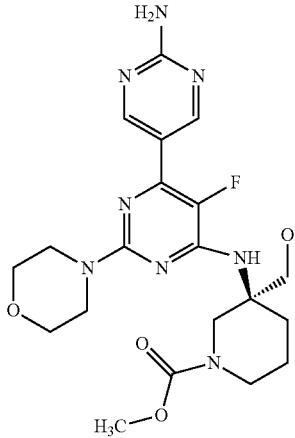<br>methyl (3S)-3-{[2'-amino-5-fluoro-2-(morpholin-4-yl)-4,5'-bipyrimidin-6-yl]amino}-3-(hydroxymethyl)piperidine-1-carboxylate | 485.1 [M + 23] | 1H NMR (400 MHz, CHLOROFORM-d) δ 8.92 (s, 2H), 5.34 (s, 2H), 4.20 (d, J = 13.8 Hz, 1H), 3.88 (br s, 2H), 3.84-3.74 (m, 5H), 3.74-3.44 (m, 8H), 3.15 (d, J = 13.8 Hz, 1H), 3.07 (br s, 1H), 2.62 (br s, 1H). |
| 155 | 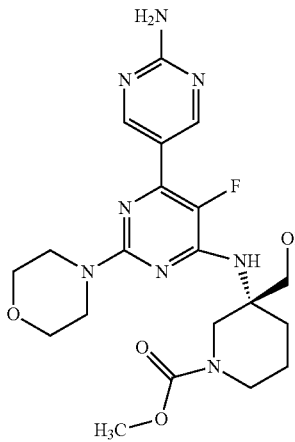<br>methyl (3R)-3-{[2'-amino-5-fluoro-2-(morpholin-4-yl)-4,5'-bipyrimidin-6-yl]amino}-3-(hydroxymethyl)piperidine-1-carboxylate | 463.1 | 1H NMR (400 MHz, CHLOROFORM-d) δ 8.90 (s, 2H), 5.35 (s, 2H), 5.15-4.35 (m, 1H), 4.20 (d, J = 13.6 Hz, 1H), 4.06-3.85 (m, 2H), 3.83-3.50 (m, 13H), 3.15 (d, J = 13.8 Hz, 1H), 3.07 (br s, 1H), 2.81-2.39 (m, 1H). |

TABLE 1-continued

| Example Number | Structure and Compound Name | LRMS m/z [M + H]+ | 1H NMR |
|---|---|---|---|
| 156 | 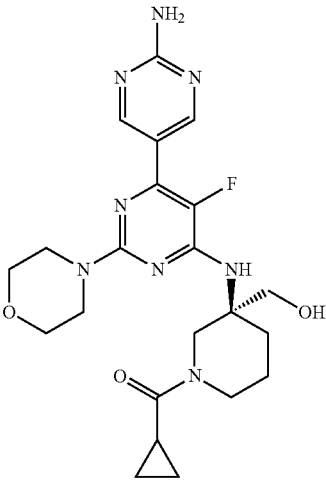 [SMILES: Nc1ncc(-c2nc(N3CCOCC3)nc(N[C@@]3(CO)CCCN(C(=O)C4CC4)C3)c2F)cn1]<br>[(3S)-3-{[2'-amino-5-fluoro-2-(morpholin-4-yl)-4,5'-bipyrimidin-6-yl]amino}-3-(hydroxymethyl)piperidin-1-yl](cyclopropyl)methanone | 473.0 | 1H NMR (400 MHz, DMSO-$d_6$) δ 8.76 (d, J = 7.8 Hz, 2H), 7.14 (s, 2H), 6.06-5.85 (m, 1H), 4.90-4.82 (m, 1H), 4.66-4.39 (m, 1H), 4.10-3.71 (m, 3H), 3.71-3.53 (m, 8H), 3.27-2.73 (m, 2H), 2.19-2.03 (m, 1H), 1.78 (br s, 1H), 1.78-1.37 (m, 3H), 0.86-0.55 (m, 3H), 0.54-0.28 (m, 1H). |
| 157 | 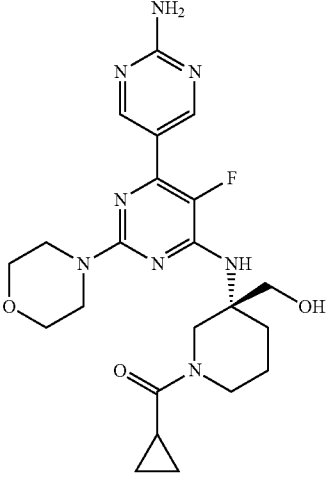 [SMILES: Nc1ncc(-c2nc(N3CCOCC3)nc(N[C@]3(CO)CCCN(C(=O)C4CC4)C3)c2F)cn1]<br>[(3R)-3-{[2'-amino-5-fluoro-2-(morpholin-4-yl)-4,5'-bipyrimidin-6-yl]amino}-3-(hydroxymethyl)piperidin-1-yl](cyclopropyl)methanone | 472.9 | 1H NMR (400 MHz, DMSO-$d_6$) δ 8.76 (d, J = 7.8 Hz, 2H), 7.14 (s, 2H), 6.06-5.85 (m., 1H), 4.90-4.82 (m, 1H), 4.66-4.39 (m, 1H), 4.10-3.71 (m, 3H), 3.71-3.48 (m., 8H), 3.20-2.90 (m, 2H), 2.19-2.03 (m, 1H), 1.79 (br s, 1H), 1.71-1.33 (m, 3H), 0.94-0.56 (m, 3H), 0.54-0.28 (m, 1H). |

TABLE 1-continued

| Example Number | Structure and Compound Name | LRMS m/z [M + H]+ | 1H NMR |
|---|---|---|---|
| 158 | 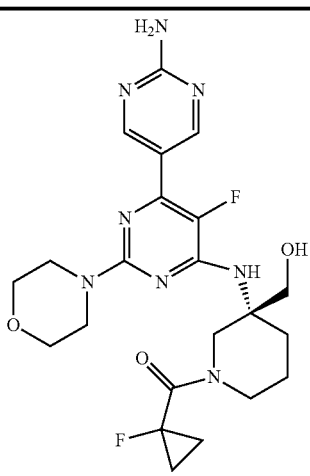<br>[(3R)-3-{[2'-amino-5-fluoro-2-(morpholin-4-yl)-4,5'-bipyrimidin-6-yl]amino}-3-(hydroxymethyl)piperidin-1-yl](1-fluorocyclopropyl)methanone | 491.0 | 1H NMR (400 MHz, DMSO-$d_6$) δ 8.76 (s, 2H), 7.14 (s, 2H), 5.89 (br s, 1H), 4.88 (br s, 1H), 4.64-4.22 (m, 1H), 3.97-3.81 (m, 2H), 3.79-3.41 (m, 11H), 3.23-2.57 (m, 1H), 1.73-1.52 m, 3H), 1.39-0.96 (m, 4H). |
| 159 | 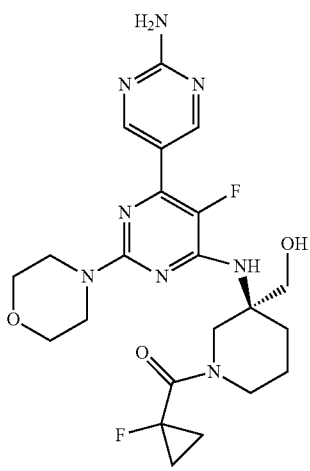 [SMILES: Nc1ncc(-c2nc(N3CCOCC3)nc(N[C@@]3(CO)CCCN(C(=O)C4(F)CC4)C3)c2F)cn1]<br>[(3S)-3-{[2'-amino-5-fluoro-2-(morpholin-4-yl)-4,5'-bipyrimidin-6-yl]amino}-3-(hydroxymethyl)piperidin-1-yl](1-fluorocyclopropyl)methanone | 491.0 | 1H NMR (400 MHz, DMSO-$d_6$) δ 8.76 (s, 2H), 7.14 (s, 2H), 5.90 (br s, 1H), 5.00 (br s, 1H), 4.88 (br s, 1H), 4.64-4.24 (m, 1H), 3.93-3.86 (m, 2H), 3.81-3.47 (m, 11H), 3.16-2.93 (m, 1H), 1.82-1.52 (m, 3H), 1.36-0.82 (m, 4H). |

*Compounds are single enantiomers; however, absolute stereochemistry was not determined.

Enzyme Production for Biochemical Assay:
p110α-iSH2 p85α Complex (Full Length p110α and p85α iSH2)("PI3KA Act")

Genes encoding for full length p110α and p85α nSH-iSH2=niSH2 (p85α amino acids 322-600) subunits of PI3Kα complex were subcloned from existing constructs into pFASTBAC Dual vector (Life Technologies, Carlsbad, Calif.) using standard cloning procedures. Gene encoding p110α subunit was subcloned into polyhedrine promoter while gene encoding p85α niSH2 domains was subcloned into p10 promoter. Additionally, Human Rhinovirus 3C Protease ("HRV 3C") site was introduced between nSH2 and iSH2, replacing amino acids 431-438 of p85a with LEV-LFQGP HRV 3C recognition sequence, using standard QuickChange mutagenesis protocol (Agilent Technologies, CA). Recombinant baculovirus was generated using Bac-to-Bac protocol (Life Technologies, Carlsbad, Calif.). Large scale expression was conducted in Sf21 (Life Technologies, Carlsbad, Calif.) cells at a multiplicity of infection ("MOI")=1 for 48 hours. Cells were lyzed in 50 mM Tris pH 8.0, 250 mM NaCl, 5% glycerol, 0.25 mM TCEP, and 20 mM imidazole. The p110α-niSH2 p85α complex was purified from clarified supernatant using Immobilized Metalo Affinity Chromatography ("IMAC"). The protein was eluted from the column using 50 mM Tris pH 8.0, 200 mM NaCl, 0.25 mM TCEP, and 200 mM imidazole. Following elution p110α-niSH2 p85α complex was dialyzed against 4 liters of 50 mM Tris pH 8.0, 200 mM NaCl, 0.25 mM TCEP, and 40 mM imidazole in the presence of PreScission Protease (1:70 molar ratio of Protease to Protein) and TEV protease (1:40 molar ratio protease to protein) for 16 hours at 4° C. The protein was further purified using reverse IMAC to remove cleaved histidine tag and contaminants captured during initial IMAC purification. The mixture of p110α-iSH2 p85α complex and cleaved nSH2 was recovered in reverse IMAC 40 mM imidazole flow through and 60 mM imidazole wash fractions. Those fractions were pulled together and loaded on Superdex 200 26/60 SEC column equilibrated in 25 mM Tris, pH 8.0, 100 mM NaCl, 2% glycerol, and 2 mM TCEP. Following SEC, chromatography peak fractions containing p110α-iSH2 p85α complex were pulled and concentrated to 4.3 mg/mL. Purity and integrity of the complex was confirmed using LCMS, analytical SEC and SDS-PAGE (sodium dodecyl sulfate polyacrylamide gel electrophoresis) analysis.

Biochemical Assay

The biochemical assays of kinase activity of full-length PI3Kα (full-length p110α/p85α) or truncated PI3Kα (p110α/iSH2 p85α) were conducted using a fluorescence polarization format similar to the procedure of Yuan J., et al., (2011) "PF-04691502, a Potent and Selective Oral Inhibitor of PI3K and mTOR Kinases with Antitumor Activity", *Mol Cancer Ther.* 10, 2189-2199. The enzymatic reactions were conducted in 50 μL volumes in 96-well plates. The reactions contained human recombinant PI3Kα (2 nM full-length p110α/p85α or 0.5 nM p110α/iSH2 p85) and 30 μM phosphatidylinositol 4,5-bisphosphate ("PIP2") (Avanti Polar Lipids, Inc., Alabaster, Ala.) and were sonicated for 1 minute prior to adding PI3Kα enzyme (PI3KA_Act or PI3KA_FL), DMSO or test compound (12-point 3-fold serial dilution, 3 μM top dose, 2% DMSO final concentration), 5 mM MgCl$_2$, 50 mM HEPES pH 7.4, 150 mM NaCl, 1 mM DTT, and 0.05% 3-[(3-cholamidopropyl)dimethylammonio]-1-propanesulfonate ("CHAPS"). The reactions were initiated by the addition of ATP (41 μM, ~Km-level, for full-length p110α/p85 or 1 mM ATP for p110α/iSH2 p85), following a 15-min preincubation. The reactions were incubated for 30 min at room temperature, stopped with EDTA pH 8 (10 mM final concentration). In a detection plate, 15 μL of detector/probe mixture, containing 480 nM GST-Grp1PH domain protein (University of Dundee, Dundee, UK) and 12 nM carboxytetramethylrhodamine ("TAMRA")-tagged fluorescent phosphatidylinositol (3,4,5)-triphosphate ("PIP3") (Echelon Biosciences, Inc., Salt Lake City, Utah) in assay buffer, was mixed with 15 μL of kinase reaction mixture. The plate was shaken for 30 minutes and fluorescence polarization values were measured on an LJL Analyst HT plate reader (Molecular Devices, Sunnyvale, Calif.). The inhibitors were shown to be ATP-competitive from kinetic and crystallographic studies. The inhibition constants (Ki) were calculated by fitting fluorescence polarization values, corresponding to initial reaction rates, to the Morrison equation (Morrison, J. F. (1969) Kinetics of the reversible inhibition of enzyme catalyzed reactions by tight-binding inhibitors. *Biochim. Biophys. Acta* 185, 269-286) for tight-binding competitive inhibitors using non-linear regression method (GraphPad Prism, GraphPad Software, San Diego, Calif.).

The results of the biological assay for the compounds tested are listed in Table 2.

TABLE 2

| Example Number | PI3KA_Act Ki (nM) |
| --- | --- |
| 1 | 0.020 |
| 2 | <0.018 |
| 3 | 2.61 |
| 4 | 0.030 |
| 5 | <0.018 |
| 6 | 0.881 |
| 7 | 0.058 |
| 8 | <0.018 |
| 9 | 0.492 |
| 10 | 1.617 |
| 11 | 0.103 |
| 12 | 1.288 |
| 13 | 0.229 |
| 14 | 1.072 |
| 15 | 0.979 |
| 16 | 0.858 |
| 17 | 2.237 |
| 18 | 0.078 |
| 19 | 0.158 |
| 20 | 0.129 |
| 21 | 0.605 |
| 22 | 0.029 |
| 23 | 1.591 |
| 24 | <0.018 |
| 25 | 0.049 |
| 26 | <0.018 |
| 27 | 0.717 |
| 28 | 0.201 |
| 29 | 5.885 |
| 30 | 2.418 |
| 31 | 2.135 |
| 32 | 0.771 |
| 33 | 0.300 |
| 34 | 0.019 |
| 35 | 0.135 |
| 36 | <0.018 |
| 37 | 0.725 |
| 38 | <0.018 |
| 39 | 0.105 |
| 40 | 0.095 |
| 41 | 0.128 |
| 42 | 0.651 |
| 43 | 1.972 |
| 44 | 0.032 |
| 45 | 0.022 |
| 46 | <0.018 |
| 47 | 0.025 |
| 48 | 0.714 |
| 49 | 0.083 |
| 50 | 0.137 |
| 51 | 0.619 |
| 52 | 0.084 |
| 53 | 0.541 |
| 54 | 2.675 |
| 55 | 0.371 |
| 56 | <0.018 |
| 57 | 0.116 |
| 58 | 0.200 |
| 59 | 0.180 |
| 60 | 12.672 |
| 61 | 0.054 |
| 62 | 0.158 |
| 63 | 0.062 |

TABLE 2-continued

| Example Number | PI3KA_Act Ki (nM) |
|---|---|
| 64 | <0.018 |
| 65 | <0.018 |
| 66 | 0.026 |
| 67 | 1.525 |
| 68 | 0.058 |
| 69 | 0.150 |
| 70 | 0.031 |
| 71 | 9.470 |
| 72 | <0.018 |
| 73 | 0.746 |
| 74 | 0.153 |
| 75 | 0.116 |
| 76 | 1.821 |
| 77 | <0.018 |
| 78 | 0.267 |
| 79 | 0.021 |
| 80 | 1.940 |
| 81 | 0.310 |
| 82 | 0.027 |
| 83 | 0.215 |
| 84 | 0.445 |
| 85 | 0.067 |
| 86 | 0.026 |
| 87 | 0.085 |
| 88 | 0.682 |
| 89 | <0.018 |
| 90 | <0.018 |
| 91 | 0.048 |
| 92 | <0.018 |
| 93 | <0.018 |
| 94 | 0.631 |
| 95 | 0.412 |
| 96 | 0.034 |
| 97 | <0.018 |
| 98 | 0.071 |
| 99 | 0.027 |
| 100 | 1.479 |
| 101 | 0.068 |
| 102 | <0.018 |
| 103 | 0.107 |
| 104 | 0.674 |
| 105 | 0.489 |
| 106 | 0.120 |
| 107 | 0.230 |
| 108 | 0.036 |
| 109 | 0.093 |
| 110 | 0.072 |
| 111 | <0.018 |
| 112 | 1.014 |
| 113 | 3.226 |
| 114 | <0.018 |
| 115 | 0.036 |
| 116 | N/D |
| 117 | <0.018 |
| 118 | <0.018 |
| 119 | <0.018 |
| 120 | <0.018 |
| 121 | 0.150 |
| 122 | 21.469 |
| 123 | 1.696 |
| 124 | 0.046 |
| 125 | 118.140 |
| 126 | 1.921 |
| 127 | 18.984 |
| 128 | 109.661 |
| 129 | 8.293 |
| 130 | 0.830 |
| 131 | 0.205 |
| 132 | 0.097 |
| 133 | 0.795 |
| 134 | N/D |
| 135 | 0.463 |
| 136 | 0.739 |
| 137 | 48.727 |
| 138 | 0.557 |
| 139 | <0.018 |
| 140 | <0.018 |
| 141 | 0.043 |
| 142 | 7.309 |
| 143 | 0.607 |
| 144 | 13.877 |
| 145 | 2.527 |
| 146 | 0.237 |
| 147 | 1.895 |
| 148 | 2.963 |
| 149 | <0.018 |
| 150 | 0.800 |
| 151 | 1.823 |
| 152 | 1.645 |
| 153 | 0.849 |
| 154 | <0.018 |
| 155 | 3.074 |
| 156 | 0.454 |
| 157 | 1.868 |
| 158 | 0.627 |
| 159 | 0.102 |

What is claimed is:

1. A compound of formula (I)

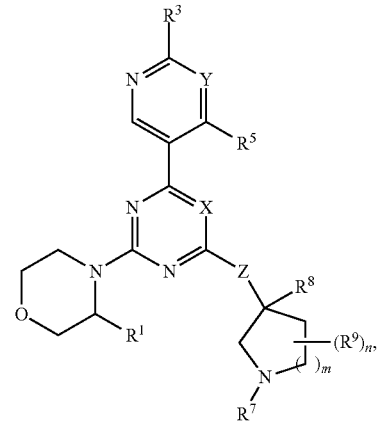

or a pharmaceutically acceptable salt thereof, wherein

X is N or CR$^2$;
R$^1$ is hydrogen or methyl;
R$^2$ is hydrogen, fluorine, or chlorine;
R$^3$ is methyl or NH$_2$;
Y is N or CR$^4$;
R$^4$ is hydrogen, cyano, or fluorine;
R$^5$ is hydrogen, methyl, or CF$_3$;
Z is NR$^6$ or O;
R$^6$ is hydrogen or C$_1$-C$_3$ alkyl;
R$^7$ is hydrogen,
  C$_1$-C$_4$ alkyl, optionally substituted by one, two, or three substituents selected from the group consisting of fluorine, hydroxy, and NH$_2$,
  —CH$_2$—(C$_3$-C$_4$ cycloalkyl),
  —C(O)—(C$_1$-C$_6$ alkyl), optionally substituted by one, two, or three substituents selected from the group consisting of fluorine, NH$_2$, hydroxy, methoxy, and phenyl, —C(O)—(C$_3$-C$_4$ cycloalkyl), optionally substituted by one or two substituents selected from the group consisting of fluorine and C$_1$-C$_4$ alkyl, —[(CH$_2$)]$_p$—C(O)-(4-5 membered heterocycloalkyl), optionally substituted by one or two substituents selected from the group consisting of fluorine and C$_1$-C$_4$ alkyl, —C(O)-(5-6 membered heteroaryl), optionally substituted by one or two substituents selected from the group consisting of fluorine and C$_1$-C$_4$ alkyl, —[(CH$_2$)]$_p$—C(O)—[N(R$^{10}$)(R$^{11}$)], —C(O)O—(C$_1$-C$_4$ alkyl), optionally substituted by one, two, or three substituents selected from the group consisting of fluorine, NH$_2$, hydroxy, methoxy, and phenyl, —C(O)O—(C$_3$-C$_4$ cycloalkyl), optionally substituted by one or two substituents selected from the group consisting of fluorine and C$_1$-C$_4$ alkyl, —S(O)$_2$—(C$_1$-C$_4$ alkyl), 4-6 membered heterocycloalkyl, optionally substituted by one or two substituents selected from the group consisting of oxo and C$_1$-C$_4$ alkyl, or 5-6 membered heteroaryl, optionally substituted by one or two substituents selected from the group consisting of oxo and C$_1$-C$_4$ alkyl;

R$^8$ is —CH$_2$OH or —CH$_2$—O—P(O)(OH)$_2$;

R$^9$ is fluorine or methyl;

R$^{10}$ is hydrogen or methyl;

R$^{11}$ is C$_1$-C$_4$ alkyl, optionally substituted by one, two, or three fluorine atoms, provided that R$^{10}$ and R$^{11}$ may form a 4-6 membered heterocycloalkyl ring, when p is 0;

m is 0, 1, or 2;

n is 0, 1, or 2; and p is 0 or 1.

2. The compound or salt of claim 1, wherein X is N.

3. The compound or salt of claim 1, wherein X is CR$^2$.

4. The compound of claim 1, wherein Y is N.

5. The compound of claim 1, wherein Y is CR$^4$.

6. The compound of claim 1, wherein Z is NR$^6$.

7. The compound of claim 1, wherein Z is O.

8. The compound or salt of claim 1, wherein R$^7$ is —C(O)—(C$_1$-C$_6$ alkyl), optionally substituted by one or two substituents selected from the group consisting of fluorine, NH$_2$, hydroxy, methoxy, and phenyl, or —C(O)—(C$_3$-C$_4$ cycloalkyl), optionally substituted by one or two fluorine atoms.

9. The compound or salt of claim 1, wherein R$^7$ is —C(O)O—(C$_1$-C$_4$ alkyl), optionally substituted by one, two, or three substituents selected from the group consisting of fluorine, hydroxy, and NH$_2$, or —C(O)O—(C$_3$-C$_4$ cycloalkyl), optionally substituted by fluorine or methyl.

10. The compound of claim 1, having formula (II)

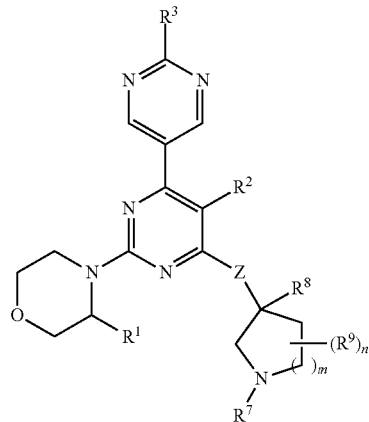

(II)

or a pharmaceutically acceptable salt thereof, wherein m is 1 or 2.

11. The compound of claim 1, having formula (III)

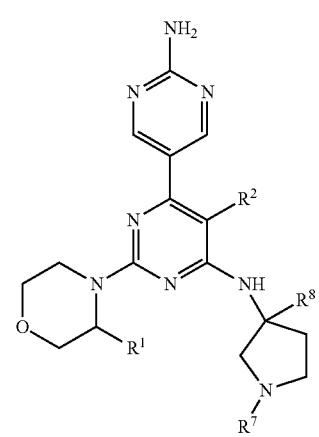

(III)

or a pharmaceutically acceptable salt thereof.

12. The compound or salt of claim 11, wherein R$^2$ is hydrogen.

13. The compound or salt of claim 11, wherein R$^2$ is fluorine.

14. The compound or salt of claim 11, wherein R$^1$ is hydrogen.

15. The compound or salt of claim 11, wherein R$^8$ is —CH$_2$OH.

16. The compound or salt of claim 11, wherein R$^8$ is —CH$_2$—O—P(O)(OH)$_2$.

17. A compound, which is

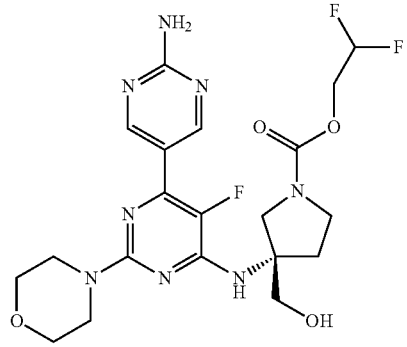 [SMILES: Nc1ncc(-c2nc(N3CCOCC3)nc(N[C@@]3(CO)CCN(C(=O)OCC(F)F)C3)c2F)cn1]

or a pharmaceutically acceptable salt thereof.

18. A compound, which is

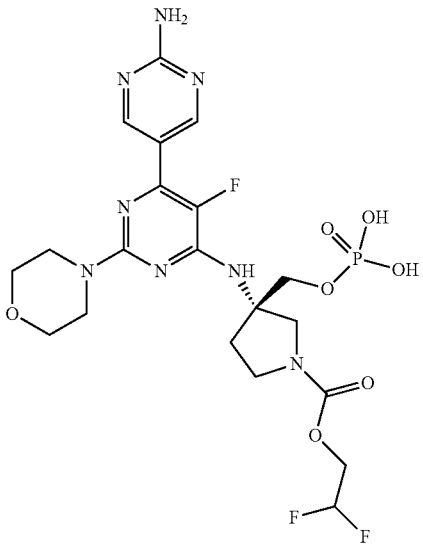 [SMILES: Nc1ncc(-c2nc(N3CCOCC3)nc(N[C@@]3(COP(=O)(O)O)CCN(C(=O)OCC(F)F)C3)c2F)cn1]

or a pharmaceutically acceptable salt thereof.

19. A pharmaceutical composition comprising a compound of claim 1, or a pharmaceutically acceptable salt thereof, and a pharmaceutically acceptable carrier or diluent.

20. A pharmaceutical composition comprising a compound, which is

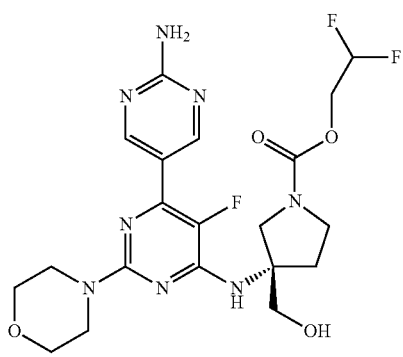 [SMILES: Nc1ncc(-c2nc(N3CCOCC3)nc(N[C@@]3(CO)CCN(C(=O)OCC(F)F)C3)c2F)cn1]

or a pharmaceutically acceptable salt thereof, and a pharmaceutically acceptable carrier or diluent.

21. A pharmaceutical composition comprising a compound, which is

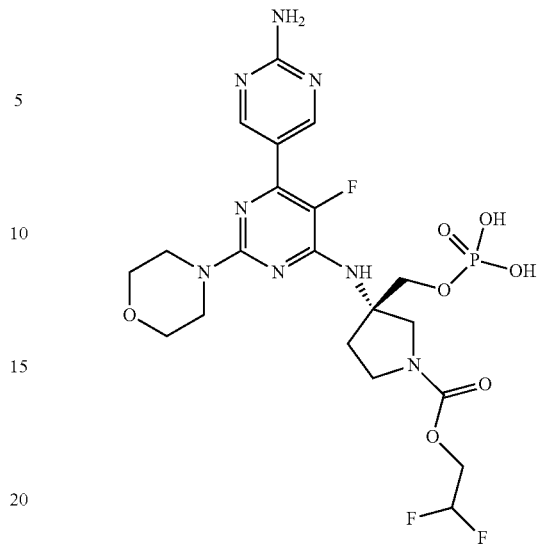

or a pharmaceutically acceptable salt thereof, and a pharmaceutically acceptable carrier or diluent.

22. A method of treating abnormal cell growth mediated by PI3Kα in a mammal having said abnormal cell growth, comprising administering to the mammal an amount of a compound of claim 1, or a pharmaceutically acceptable salt thereof, that is effective in treating said abnormal cell growth.

23. The method of claim 22, wherein the abnormal cell growth mediated by PI3Kα is cancer.

24. The method of claim 23, wherein the cancer is selected from the group consisting of lung cancer, cancer of the head or neck, colon cancer, breast cancer, stomach cancer, and ovarian cancer, or a combination of one or more of the foregoing cancers.

25. A method of treating abnormal cell growth mediated by PI3Kα in a mammal having said abnormal cell growth, comprising administering to the mammal an amount of a compound of claim 17, or a pharmaceutically acceptable salt thereof, that is effective in treating said abnormal cell growth.

26. The method of claim 25, wherein the abnormal cell growth mediated by PI3Kα is cancer.

27. The method of claim 26, wherein the cancer is selected from the group consisting of lung cancer, cancer of the head or neck, colon cancer, breast cancer, stomach cancer, and ovarian cancer, or a combination of one or more of the foregoing cancers.

28. A method of treating abnormal cell growth mediated by PI3Kα in a mammal having said abnormal cell growth, comprising administering to the mammal an amount of a compound of claim 18, or a pharmaceutically acceptable salt thereof, that is effective in treating said abnormal cell growth.

29. The method of claim 28, wherein the abnormal cell growth mediated by PI3Kα is cancer.

30. The method of claim 29, wherein the cancer is selected from the group consisting of lung cancer, cancer of the head or neck, colon cancer, breast cancer, stomach cancer, and ovarian cancer, or a combination of one or more of the foregoing cancers.

* * * * *